(12) United States Patent
Pangalos et al.

(10) Patent No.: US 7,217,555 B1
(45) Date of Patent: May 15, 2007

(54) CLONING AND CHARACTERISATION OF NOVEL MAMMALIAN PEPTIDASE

(75) Inventors: Menelas Pangalos, London (GB); Jean-Marc E. F. M. Neefs, Lier (BE); Danielle C. G. Peeters, Herk-de-Stad (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 09/743,647

(22) PCT Filed: Jul. 14, 1999

(86) PCT No.: PCT/GB99/02241

§ 371 (c)(1),
(2), (4) Date: Jan. 12, 2001

(87) PCT Pub. No.: WO00/04157

PCT Pub. Date: Jan. 27, 2000

(30) Foreign Application Priority Data

Jul. 14, 1998 (GB) .................................. 9815284.6

(51) Int. Cl.
*C12N 9/64* (2006.01)
*C12N 15/57* (2006.01)
*C12N 15/74* (2006.01)
*C12N 15/79* (2006.01)

(52) U.S. Cl. .................. 435/226; 435/69.1; 435/252.3; 435/320.1; 536/23.2

(58) Field of Classification Search ..................... None
See application file for complete search history.

(56) References Cited

FOREIGN PATENT DOCUMENTS

WO    WO 96/15258    *    5/1996

OTHER PUBLICATIONS

Carter, R.E., et al., 1996,: "Prostate-specific membrane antigen is a hydrolase with substrate and pharmacologic characteristics of a neuropeptidase", Proceedings of the National Academy of Sciences, USA, vol. 93, pp. 749-753.*
Shneider, B.L., et al. 1997, "Cloning and characterization of a novel peptidase from rat and human ileum", The Journal of Biological Chemistry, vol. 272, No. 49, pp. 31006-31015.*
Luthi-Carter, R. et al., 1998, "Isolation and characterization of a rat brain cDNA encoding glutamante carboxypeptidase II," Proceedings of the National Academy of Sciences, USA, vol. 95, pp. 3215-3220.*
Pangalos, H.N., et al., 1999, "Isolation and expression of novel human glutamate carboxyqeptidases with N-acetylated alpha-lInked acidic dipeptldase peptidase IV activity", The Journal of Biological Chemistry, vol. 274, No. 13, pp. 8470-8483.*
Seffernick, J.L., et al., 2001, "Melamine deaminase and atrazine chlorohydrolase: 98 percent identical but functionally different", Journal of Bacteriology, vol. 183, No. 8, pp. 2405-2410.*

* cited by examiner

*Primary Examiner*—Nashaat T. Nashed
*Assistant Examiner*—William W. Moore

(57) ABSTRACT

There is disclosed a cDNA molecule encoding human NAALAD-ases designated herein as L, II and IV and having the amino acid sequences illustrated in FIGS. 1, 3, 4 and 5. The NAALAD-ases themselves also form part of the invention. Further provided are expression vectors incorporating the cDNA molecules suitable for transforming a cell, tissue or organism.

2 Claims, 23 Drawing Sheets

Figure 7:
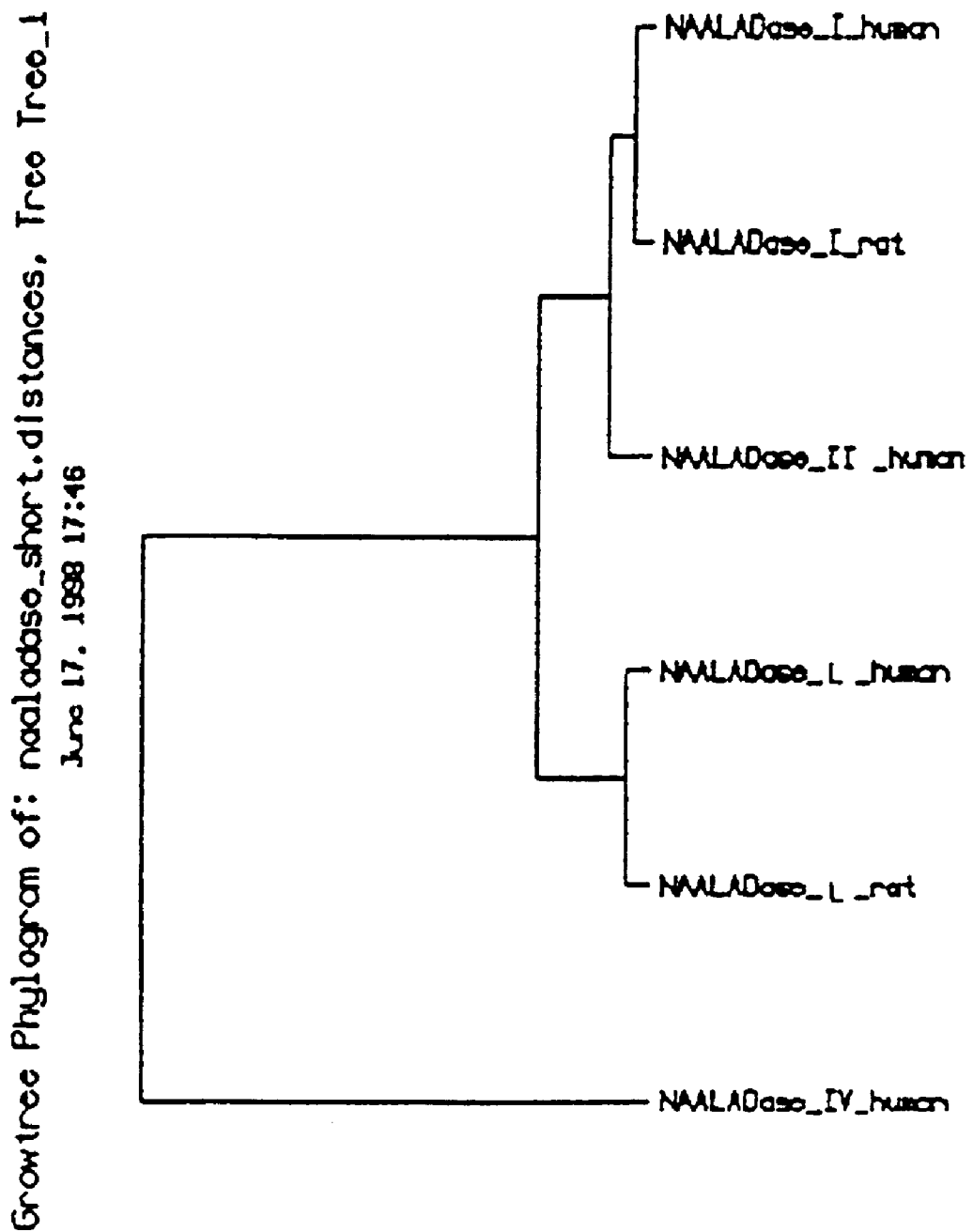

```
MQWTKVLGLGLGAAALLGLGIILGHFAIPKKANSLAPQDLDLEILETVMGQLDAHRIRENLRELSREPHLASSPRDEDLVQLLLQRWKDP    90 deletion 1 (bp 497-619)
                                                            ↓
ESGLDSAEAXTYEVLLSFPSQEQPNVVDIVGPTGGIIHSCHRTEENVTGEQGGPDVVQPYAAYAPSGTPQGLLVYANRGAEEDFKELQTQ   180

GIKLEGTIALTRYGGVGRGAKAVNAAKHGVAGVLVYTDPADINDGLSSPDETFPNSWYLPPSGVERGSYYEYFGDPLTPYLPAVPSSFRV   270 gtgagcgtctacaaccgcctggagctgaggaactcttccaacgtcctgggcatcatccg
                                                            tggggctgtggagcctggtgagccctcctcttgctgcctgcaccccaggcccctgctct
                                                            gctctggatgccgctgtcctcatccagccctgcccttgccaccacccagcccagctccc
              deletion 2 (bp 903-1007)                      cctgcccacctctccctctcctctggttctctgccccttttcctctggccag
                                                                     insertion at bp 1094   ▽
                         ↓                                                                  △
DLANVSGFPPIPTQPIGFQDARDLLCNLNGTLAPATWQGALGCHYRLGPGFRPDGDFPADSQVNVSVYNRLELRNSSNVLGIIRGAVEP-  359
                                                                                         G -----------------------------------------------------DRYVLYGNHRDSWVHGAVDPSSGTAVLLELSRVLGTLLKK  399
EPSSCCLHPRPLLCSGCRCPHPALPLPPPSPAPPAHLSLSSGSLPLFLWP GTWRPRRSIVFASWGAEEFGLIGSTEFTEEFFNKLQERTVAYINVDISVFANATLRVQGTPPVQSVVFSATKEIRSPGPGDLSIYDNWIR  489
```

FIG. 1.

FIG. 1. (CONTINUED)

```
CCTCCTGGAGCTCTCCCGTGTCCTGGGACCCTGTGAAGAAGGCACCCTGGCGTCTCGAGATCAATGTGTTGCGAGCTGGGGGC    1260
 L  L  E  L  S  R  V  L  G  T  L  L  K  K  G  T  W  R  P  R  R  S  I  V  F  A  S  W  G  A

TGAGGAGTTGGCTCATTGGCTCCACGGAATTCACAGAAGAGTTCTTCAACAGCTGCAGGAGCGACGGTGGCTACATCAACGTGA    1350
 E  E  F  G  L  I  G  S  T  E  F  T  E  E  F  F  N  K  L  Q  E  R  T  V  A  Y  I  N  V  D

CATCTCCGTGTTTGCCAACCTGACCCTTAGGGTGCAGGGGACGCCCCCTGTCCAGAGCGTCGTCTTCTCTGCAACCAAAGAGATCCGCTC    1440
 I  S  V  F  A  N  A  T  L  R  V  Q  G  T  P  P  V  Q  S  V  V  F  S  A  T  K  E  I  R  S

ACCAGGCCCTGGCGACCTGAGCATCTACGACAACTGGATCCGTACTTCAACCGCAGCAGCCCGGTGTACGGCCTGGTCCCCAGCTTGGG    1530
 P  G  P  G  D  L  S  I  Y  D  N  W  I  R  Y  F  N  S  S  P  V  Y  G  L  V  P  S  L  G

TTCTCTGGGTGCTGGCAGGACTATGCACCCCACCTACCACTACCCACTACCCCTTCACTCGTTCACCCTTGACACCTTTGACTATGTGGACAAGTTTTTTGACCCGGGCTTCAGCAGCCA    1620
 S  L  G  A  G  S  D  Y  A  P  F  V  H  F  L  G  I  S  S  M  D  I  A  Y  T  Y  D  R  S  K

GACTTCAGCCAGGATCTACCCCACCTACCACTACCCACTACCCCTTCACTCGTTCACCCTTGACACCTTTGACTATGTGGACAAGTTTTTTGACCCGGGCTTCAGCAGCCA    1710
 T  S  A  R  I  Y  P  T  Y  H  T  A  F  D  T  F  D  Y  V  D  K  F  L  D  P  G  F  S  S  H

TCAGGCTGTGGCCCGACAGCGGGGAGTGTGATTCTCCGGCTCAGTGACGACAGCTTCTTCCCCCTCAAAGTCAGTGACTACAGTGAGAC    1800
 Q  A  V  A  R  T  A  G  S  V  I  L  R  L  S  D  D  S  F  F  L  P  L  K  V  S  D  Y  S  E  T

ACTCCGCAGTTCCTGCAGGCAGCCCAGCAAGATCTGGGGCTGCTGGAGCAGCACAGCATCAGCTGGGCCTCTGTGACTGCAGT    1890
 L  R  S  F  L  Q  A  A  Q  Q  D  L  G  A  L  L  E  Q  H  S  I  S  L  G  P  L  V  T  A  V

GGAGAAGTTTGAGGCAGAGGCAGCAGCCCTTGGGCAACAGCTGACCAACACTGCAGAAGGGCAGCCCCTGACCCCTGCAGGTCCGGATGCT    1980
 E  K  F  E  A  E  A  A  A  L  G  Q  R  I  S  T  L  Q  K  G  S  P  D  D  P  L  Q  V  R  M  L

CAATGACCAGTTGATGCTCTTGGAACGACTTTCTTGAACCTGAACTTCCTGTCCAGGGCCTACTACAGCTGCTCTGGCACC    2070
 N  D  Q  L  M  L  L  E  R  T  F  L  N  P  R  A  F  P  E  E  R  Y  Y  S  H  V  L  W  A  P

TTCGCACGGGCTCCGTAGTCACATTCGGGCTATCAATGCCTGCTCCAGGGCCAGGACACAGCTTCTGGATCTGAAGCTTGGGCTGA    2160
 S  H  G  L  R  S  H  I  P  G  L  S  N  A  C  S  R  A  R  D  T  A  S  G  S  E  A  W  A  E

GGTCCAGAGACAGCTGAGCATTGTGGTGACACAGCCCTGAGGGTGCGGCAGCACCTGAGGCCTGACCTGACCCTGACCCCAGCCCTC    2250
 V  Q  R  Q  L  S  I  V  V  T  A  L  E  G  A  A  A  T  L  R  P  V  A  D  L  *

TTTCTTCAGCCCTCCCTTACTCCGGTGCTTTATATTTACAAAGTGCTTTGTGTTTTTTAAAGTCTTTT    2320
```

FIG. 2

```
human  MCMTKVLGLGLGAAALLGLGIILGHFAIPKKANSLAP------QDLDLEILETVHGQLDAHRIRENLRELSREPHLASSPRDEDLVQLLLQ  : 85
rat    MHWAKILGVGIGAAALLGLGIILGHFAIPHATEPLASSVSDSQDLDLAILDSVHGQLDASRIREMLRELSKEPHVATSARDEALVQLLLG  : 90 human  RMKDPESGLDSAEAXTIEVLLSFPSCEQPNVIDIVGPTEGIIHSCHRTEENVTGECGGPDVVQPYAAYAPSGTPCELVVYANRGAEEDFK  : 175
rat    RMKDSASGLDTAKTYENTVLLSFPSTEQPNSVEVVGPNGTMFHSFQPFEKNLTGECAEPNVLQPYAAYAFPGTFKGPLVYANRGSEDDFK  : 180 human  ELCTQGIKLEGTIALTRYGCVGRGAKAVTAAAKHGVAGVLVYTDFADINDGLSSPDETFPNSUYLPPSSGVERGSYYEYFGDPLTPYLPAVP  : 265
rat    KLEAEGINLKGTIALTRYGSVGRGAKAINAARHGWVGVLVYTDFGDINDGKSLPNETFPNSWGLPPSSGVERGSYYEYFGDPLTPYLPPHP  : 270 human  SSFRVDLANVSGFPIPTQPIGFQDARDLLCNLNGTLAPATWQGALGCHYRLGPGFRPDGDFPADSQVNVSVNRLELRNSSNVLGIIRG  : 355
rat    VSFRLDPHNISGFPIPTQPIGFEDAKNLLCNLNGTSAPDSWQGALGCEYKLGPGFEPNGNFPAGSEVKVSVNRLELRNSSNVLGIICG  : 360 human  AVEPDRTVLYGNHRDSWHGAVDPSSGTAVLLELSRVLGTLLKKGTWRPRRSIVFASWGAEEFGLIGSTEFTEEFNKLQERTVAYINVD  : 445
rat    AVEPDRYVIYGNHRDSWHGAVDPSSGTAVLLEISRVLGTLLKKGTWRPRRSIIFASWGAEEFGLIGSTEFTEEFLSKLQERTVTYINVD  : 450
```

FIG. 2 (CONTINUED)

```
human  ISVFANATLPVQGTPPVQSVVFSATKEIRSPGPGDLSIYDNWIRYFNRSSPVYGLVPSLGSLGAGSDYRPFVHFLGISSNDIAYTYDRSN  : 535
rat    ISVFSNATLPAQGTPPVQSVVFSATKEISAPGSSGLSIYDNWIRYTNRSSPVYGLVPSNGTLGAGSDYRSFIHFLGITSNDLAYTYDRSF  : 540 human  TSARIYPTYHTAFDTFDYNDKFLDPGFSSHQAVARTAGSVILRLSDSFFLPLKVSDYSETLRSFLQAAQQDLGALLECHSISLGPLVTAV  : 625
rat    TSARIYPTYHTAFDTFDYVEKFLDPGFSSHQAVARTAGSVLLRLSDSLFLPLNVSDYSETLQSFLQAAQENLGALLESHNISLGPLVTAV  : 630 human  EKFEAEAAALGCRTSTLQKGSPDPLQVRHLNDQLILLLEFTFLNPRAFPEERYYSHVLVAPSHGLRSHIPGLSNACSRARDTASGSEAWAE  : 715
rat    EKFKAAAALNCHILTLQKSSPDPLQVRIVNDQLILLLEPAFLNPRAFPEERYYSHVLNAPNTASVATFPGLANIYARAQEINSGAEAWAE  : 720 human  VQRQLSIVWTALEGAAAATLRPVADL--  : 740
rat    VERQLSIAVMALEGAAAATLQPVTDL--  : 745
```

FIG. 3.

MQWTKVLGLGLGAAALLGLGIILGHFAIPKKANSLAPQDLDLEILETVMGQLDAHRIRENLRELSREPHLASSPRDEDLVQLLLQRWKDP 90 deletion 1 (bp 497-619)
→
ESGLDSAEAXTYEVLLSFPSQEQPNVDIVGPTGGIIHSCHRTEENVTGEQGGPDVVQPYAAYAPSGTPQGLLVYANRGAEEDFKELQTQ 180

GIRLEGTIALTRYGGVGRGAKAVNAAKHGVAGVLVYTDPADINDGLSSPDETFPNSWYLPPSGVERGSYYEYFGDPLTPYLPAVPSSFRV 270

```
                                gtgagcgtctacaaccgcctggagctgaggaactcttccaacgtcctggcatcatccg
                                tggggctgtggagcctggtgagccctcctcttgctgcctgcaccccaggccctgctct
                                gctctggatgccgctgtcctcatccagccctgccctgccaccaccagccagcttccc
                                cctgcccacctccctcctcctctgttctctgccccttttcctctggccag
```
                                insertion at bp 1094  359
                                                                                G deletion 2 (bp 903-1007)
→
DLANVSGFPPIPTQPIGFQDARDLLCNLNGTLAPATWQGALGCHYRLGPGFRPDGDFPADSQVNVSVYNRLELRNSSNVLGIIRGAVEP-

---------------------------------DRYVLYGNHRDSWVHGAVDPSSGTAVLLELSRVLGTLLKK 399

EPSSCCLHPRPLLCSGCRCPHPALPLPPPSPAPPAHLSLSSGSLPLFLWP

GTWRPRRSIVFASWGAEEFGLIGSTEFTEEFFNKLQERTVAYINVDISVFANATLRVQGTPPVQSVVFSATKEIRSPGPGDLSIYDNWIR 489

FIG. 3 (CONTINUED)

deletion 3 (bp 1525-1615); deletion 4 (bp 1525-1615)

gtgaggaggagacaaggggcatccctgagaccaggacaggaggctgaagactgagccctggccttgtcacctgccgcag

YFNRSSPVYGLVPSLGSLGAGSDYAPFVHFLGISSMDIAYTYDRSKTSARIYPTYHTAFDTFDYVDKFLDPGFSSHQAVARTAGSVILRL    579
RLQQPSGCGPDSGECDSPAQ*
RARLQPGS PPTTQPLTPLTMWTSFWTRASAAIRLWPGQRGV*
△ insertion at bp 1697
EEGDKGHPETRTGEAED* gtatgcacagccctgacccctgaggtatgggggagccctgcaccccatgactgagccactgctgttcctcacag
△ insertion at bp 1870

SDSFFLPLKVSDYSETLRSFLQAAQQDLGALLEQHSISLGPLVTAVEKFEAEAAALGQRISTLQKGSPDPLQVRMLNDQLMLLERTFLNP   669
GMHSPDPEVWGALHPHD*

RAFPEERYYSHVLWAPSHGLRSHIPGLSNACSRARDTASGSEAWAEVQRQLSIVVTALEGAAATLRPVADL*   740

FIG. 4.

FIG. 4. (CONTINUED 1)

```
AAATTGCCCGGAGTTTTGGAAAAACTGATGAGTAAAGGCTGAGACCTAGAAGAACTAGAAGGCTGGATGCAGAAGAATTTG      1260
 I  A  R  S  F  G  K  L  M  S  K  G  W  R  P  R  R  T  I  I  F  A  S  W  D  A  E  E  F  G

GACTTCTGGGTTCACAGAATGGGCTGAGGAGAATGTCAAAATACTCCAGGAGAGCATTGCTTATATCAACTCGGATTCATCTATAG   1350
 L  L  G  S  T  E  W  A  E  E  N  V  K  I  L  Q  E  R  S  I  A  Y  I  N  S  D  S  S  I  E

AAGGCAATTATACTCTCAGAGTTGACTGTACTCCCCCTTCTTTACCAATTAGTGTATAAACTGACAAAGAGATCCCCAGCCCTGATGATG  1440
 G  Y  T  L  R  V  D  C  T  P  L  L  Y  Q  L  V  Y  K  L  T  K  E  I  P  S  P  D  D  G

GGTTTGAGAGTAAATCACTGTATGAAAGCTGGTTGGAAAAAGACCCTTCACCTGAAAATAAAATTTGCCTAGAATCAATAAGCTGGAT   1530
 F  E  S  K  S  L  Y  E  S  W  L  E  K  D  P  S  P  E  N  K  N  L  P  R  I  N  K  L  G  S

CTGGAAGTGACTTTGAGCTTATTTCAGAGACTTGGAATTGCTTCAGGCAGAGAGCCCGTTACACTAAGAATAAGAAAACAGATAAGTACA  1620
 G  S  D  F  E  A  Y  F  Q  R  L  G  I  A  S  G  R  A  R  Y  T  K  N  K  K  T  D  K  Y  S

GCAGCTACCCAGTGTACCACACAATTTATGAGACATTTGAATTGGTAGAGAAATTTTATGACCCCACATTTAAAAAACAACTTTCTGTGG   1710
 Y  P  V  V  Y  H  T  I  Y  E  T  F  E  L  V  E  K  F  Y  D  P  T  F  K  K  Q  L  S  V  A

CTCAATTACGAGGAGCACTGGTATGAGCTTGTGGATTCTAAAATCATTCCTTTTAATATTCAAGACTATGCAGAAGCTTTGAAAAACT   1800
 Q  L  R  G  A  L  V  Y  E  L  V  D  S  K  I  I  P  F  N  I  Q  D  Y  A  E  A  L  K  N  Y

ATGCAGCAAGTATCTATAATCTATCTAAGAAACATGATCAACAATTAACACAAGTGGTAGTCATTGACTCCTTATTTTCTGCTGTGA   1890
 A  A  S  I  Y  [N] L  S  K  K  H  D  Q  Q  L  T  D  H  G  V  S  F  D  S  L  F  S  A  V  K

AAAACTTCTCAGAGGCTGCTTCAGATTTTCATAAACGACTTATACAAGTTGATCTTAACAATCCCATTGCAGTGAGAATGATGAATGACC   1980
 [N] F  S  E  A  A  S  D  F  H  K  R  L  I  Q  V  D  L  N  N  P  I  A  V  R  M  M  N  D  Q

AACTGATGCTCCTGAAAGAGCATTCATCATCGATCCTCTTGGTTTACCAGGAAAGCTGTTCTATAGGCACATCATATTTGCTCCAAGTAGCC   2070
 L  M  L  E  R  A  F  I  D  P  L  G  L  P  G  K  L  F  Y  R  H  T  I  F  A  P  S  S  H

ACAACAAATATGCTGGAGAATCATTTCCTGGAATCTATGATGCTATCTTTGATATTGAAAATAAAGCCAACTCTCGTTTGGCTGAAAG    2160
 N  K  Y  A  G  E  S  F  P  G  I  Y  D  A  I  F  D  I  E  N  K  A  N  S  R  L  A  W  K  E

AAGTAAAGAAACATATTTCTATTGCAGCTTTTACAATTCAAGCAGCAGGAACTCTGAAAGAAGTATTATAGAAGGTCTCAAGTGCCT      2250
 V  K  K  H  I  S  I  A  A  F  T  I  Q  A  A  A  G  T  L  K  E  V  L  ·
```

FIG. 4. (CONTINUED 2)

```
AGCCATTAAAGGTGTTGCTAAAAGTCTGAGGATAAAATTCACCTTTCTGATAACTTATGAAGCCAGGGTGTTCTAAACTCTTTCATGTC        2340
ATGTTTTGATTATAGGCTTTGGTCTTTTCATCTGCAAAGCCTTTTTTTTTTGCTCTTTAAAAGTTAATAATTATATTAGCAAAGTGTT        2430
AATCTAATGAAGTAAAAACTCCTGTGGCAGAAAGTAAAAGAAAATTCCCTAAATTATAGCAAGGAACATGAATTCTCAGACATTGTG        2520
AGTGTGGGAATGTAAAATGTAAAATCACTTTTTGAAAACAGTTGGCAGTTCCTATAAAGTAAACATACACTTTTACTTTAGGACTCC        2610
AGAATTCCACTTCTCTAGTTATTTATTCAAGAGAAGGAAAAACAATGATCACAGCAATACTTGTATGCATGTTCAACTTAAAAGCGT        2700
AAAAACCCCAAATGTCCATCCACAGACGAATGTATAAACTGTGGTATCCATTACACAATAGACTACTTACTACTCAGCAATAAAATGAA      2790
GTAACTTTCAATAAATGCAATATATTGGCAGACATTGTTGAAGGAAAAAAGCCAGACAAACAACTACATAAAATATGTTTCTATTTAGA      2880
TGAAGTGGCAAACTAATCTGTAGTGTTAAAAATTAGATTAGTGATTGCCTGGGCCAAGTGGCAGGTTGGGGAGGATGGCTGCAAAGAAGT     2970
ATGAGGAAACTTTCTCCAATAGATGAGAATTTTCCGTATCTTGATCTGAGTGGCAAATTGTAAACTTAAAATATATATAAAATTTATTGA     3060
AAGAAAATTAAGCCTCAATAAACGTGATTATAAAAAAAAAAAAAAGG                                                3110
```

FIG. 5

```
CGGCCGCGGAGGGCCCAGCCCAGTCAGGGGTGTGGCCCGCCGCCACCGTGTAAGGCTAGGCCGGAGCTTAGTCCTGGGAGCCGCCTCCGTCG          90
CCGCCGTCAGAGCCTGCCCTATCAGATTATCTTAACAAGAAAAAAACCAACTGGAAAAAATGAAATTCCTTATCTTCGCATTTTTCGGTGG          180
                                            M  K  F  L  I  F  A  F  F  G  G
TGTTCACCTTTATCCCTGTCTGTCTCTGGGAAAGCTATATGCAAGAATGGCATCTCTAAGAGGACTTTTGAAGAAATATAAAGAGAAGAAATAGC       270
 V  H  L  L  S  L  C  S  G  K  A  I  C  K  N  G  I  S  K  R  T  F  E  E  I  K  E  E  I  A
CAGCTGTGGAGATGTTGCTAAAGCAATCATCAACCTAGCTGTTTATGTAAAGCCCAGAACAGATCCTATGAGCGATTGGCACTTCTGGT           360
 S  C  G  D  V  A  K  A  I  I  N  L  A  V  Y  G  K  A  Q  R  S  Y  E  R  L  A  L  L  V
TGATACTGTTGGACCCAGACTGAGTGCTCCAAGAACCTGGAGCCATCCAAATTATGTACCAAAACCTGCAGCAAGATGGGCTGGA             450
 D  T  V  G  P  P  R  L  S  G  S  K  N  L  E  K  K  A  I  Q  I  M  Y  Q  N  L  Q  Q  D  G  L  E
GAAAGTTCACCTGGAGCCTGTGCAGCAGCCATTGGACTCCTCCAGAGAGGCATTACGACGAAGTTCTGGTGGTGACCTCTTTCGATGAACTGCAGAG      540
 K  V  H  L  E  P  V  R  I  P  H  W  E  R  G  E  E  E  S  A  V  M  L  E  P  R  I  H  K  I  A
CATCCTGGGTCTTGCAGCAGCAGTTGAAGCAAGAGGGAAGATTGTGTTTATAACCAACCTTACATCAACTACTCAAGGACGGTGCAATACCGAACGCAGGGGC   630
 I  L  G  L  G  S  S  I  G  T  P  P  P  E  G  I  T  A  E  V  L  V  V  T  S  F  D  E  L  Q  R
AAGGGCCTCAGAAGCAAGAGGGAAGATTGTGTTTATAACCAACCTTACATCAACTACTCAAGGACGGTGCAATACCGAACGCAGGGGC             720
 R  A  S  E  A  R  G  K  I  V  V  Y  N  Q  P  Y  I  Y  S  R  T  V  Q  Y  R  T  Q  G  A
GGTGGAAGCTGCCAAGGTTGGGGCTTTGGCATTCTGATCCGCTCCGTCGCCTCTTCCATCTACAGTCCTCACAGGTATTCAGGA               810
 V  E  A  A  K  V  G  A  L  A  S  L  I  R  S  V  A  S  F  S  I  Y  S  P  H  T  G  I  Q  E
ATACCAGGATGGCGTGCCCAAGATTCCAACAGCCTGTATTACGGTGGAAGATGCAGAAATGATGTCAAGAATGGCTTCTCATGGGATCAA              900
 Y  Q  D  G  V  P  K  I  P  T  A  C  I  T  V  E  D  A  E  M  M  S  R  M  A  S  H  G  I  K
AATTGTCATTCAGCTAAAGATGGGGCCAAGACTTACCCCAGATACTGATTCCTTCAACACTGTAGCAGAGATCACTGGGAGCAAATATCC             990
 I  V  I  Q  L  K  M  G  A  K  T  Y  P  D  T  D  S  F  N  T  V  A  E  I  T  G  S  K  Y  P
AGAACAGGTTGTACTGGTCAGTGGACATCTGGACAGCTGGGATGTTGGGCAGGTGGGACAGGCTATGGATGACGGGGCAGCCTTTATATCATG           1080
 E  Q  V  V  L  V  S  G  H  L  D  S  W  D  V  G  Q  Q  G  A  M  D  D  G  G  A  F  I  S  W
GGAAGCACTCTCACTTATTAAAGATCTTGGGCTGCGTCCAAAGAGGACTCTCCGCCTGGTGCTCTGGACTGCAGAAGAACAAGGTGGAGT             1170
 E  A  L  S  L  I  K  D  L  G  L  R  P  K  R  T  L  R  L  V  L  W  T  A  E  E  Q  G  G  V
```

FIG. 5. (CONTINUED)

```
TGGTGCCTTCCAGTATTATCAGTACACAAGTAAATATTTCCAACTACAGTCTGGTGATGGAGTCTGACGCAGGAACCTTCTTACCCAC    1260
 G  A  F  Q  Y  Y  Q  L  H  K  V  N  I  S  N  Y  S  L  V  M  E  S  D  A  G  T  F  L  P  T

TGGGCTGCAATTCACTGGCAGTGAAAGGCCAGGGCCATCATGGAGGAGGTTATGAGCCTGCTGCAGCCCCTCAATATCACTCAGGTCCT    1350
 G  L  Q  F  T  G  S  E  K  A  R  A  I  M  E  E  V  M  S  L  L  Q  P  L  N  I  T  Q  V  L

GAGCCATGGAGAAGGACAGACATCAACTTTTGGATCCAAGCTGGAGTGCCTGGAGCCAGTCTACTTGATGACTTATACAAGTATTTCTT    1440
 S  H  G  E  G  T  D  I  N  F  W  I  Q  A  G  V  P  G  A  S  L  L  D  D  L  Y  K  Y  F  F

CTTCCATCACTCCCACGGAGACACCATGACTGTCATGGATCCAAAGCAGATGAATGTTGCTGCTGTTTGGGCTGTGTGTTCTTATGT    1530
 F  H  H  S  H  G  D  T  M  T  V  M  D  P  K  Q  M  N  V  A  A  A  V  W  A  V  V  S  Y  V

TGTTGCAGACATGGAAGAAATGCTGCCTAGGTCCTAGAAACAGTAAGAAACAGTTTTCATGCTTCTGGCCAGGAATCCTGGGTCTGC    1620
 V  A  D  M  E  E  M  L  P  R  S  *

AACTTTGGAAAACTCCTCTTCACATAACAATTTCATCCAATTCATCTTCAAAGCACAACTCTATTTCATGCTTTCTGTTATTATCTTTCT    1710

TGATACTTTCCAAATTCTCTGATTCTAGAAAAAGGAATCATTCTCCCCCTCCCACCACATAGAATCAACATATGGTAGGGATTACAG    1800

TGGGGGCATTTCTTTATATCACCTCTTAAAACACTCTTAAAGTAAACACTTAATAAATTTTTGGAAGATCTCTG    1884
```

```
NAALAD I     SGNDFEVFFQRLEIASGRARYTNUETNKFSGYPLYHVVYEIYELVEK----FYDPHYKYH-LTVIQVRGG------  582
NAALAD II    SGSDFEAYFQRLFIASGRARYTINKKTDKYSSYPVYHIIYETFELVEK----FYDPTYKKQ-LSVIQLRGA------  572
NAALAD L     AGSDYAPFVHFLSISSHDIAYTYDRSKTSARIYPTYRHAFDHFDYVDK---FLDPGFSSH-QAVRTAGS------   574
NAALAD IV    EGTDIN-FLIQAEVPGASLLDDLYKYFF----FHHSHGDLMTVHDPKQHNVAAAVLAVVSYVVEDMEEMLPRS---  472
APE 3 yeast  RSDYVGFINNGIPAGGIATGAERNNVNNGKVLDRCYHQLCDDVSNMSUDAFITNTKLIAHSVATYIDSFEGFPKRETQKH  515
P96152       YACSDHASEHKAGFSAAHPFESIFKDYN-----PKIHUSQDLLANSDPT--GNHAVTITKLGLAYVIEHAN------   391
AMPX vibpr   YACSDHASEHNAFYPAAHPFESKFNDYN-----PRIHUTQDLLANSDPT--GSHAKKHTQLGLAYTIEMGS------  394
APX strgr    VGVPVGGLETGAFYTKSAAQAQRUGGTAGGQAFDRCYESSCUELSNIQNDTALDRNSDALAHAIUTLSSGTGEPPT----   294
```

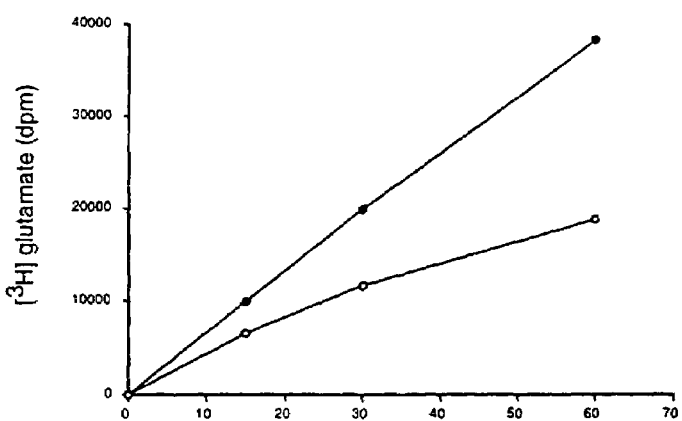
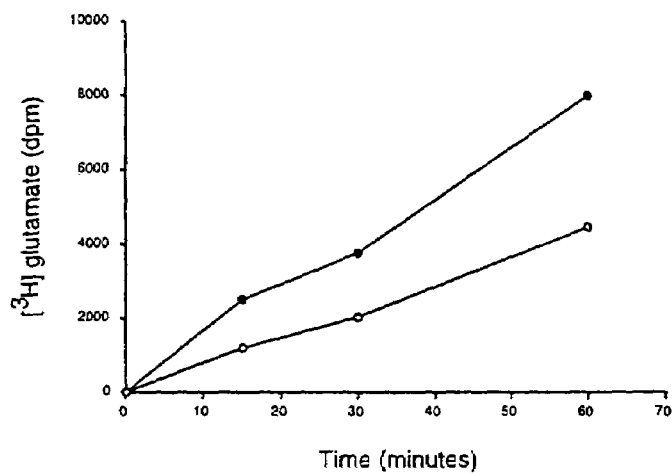
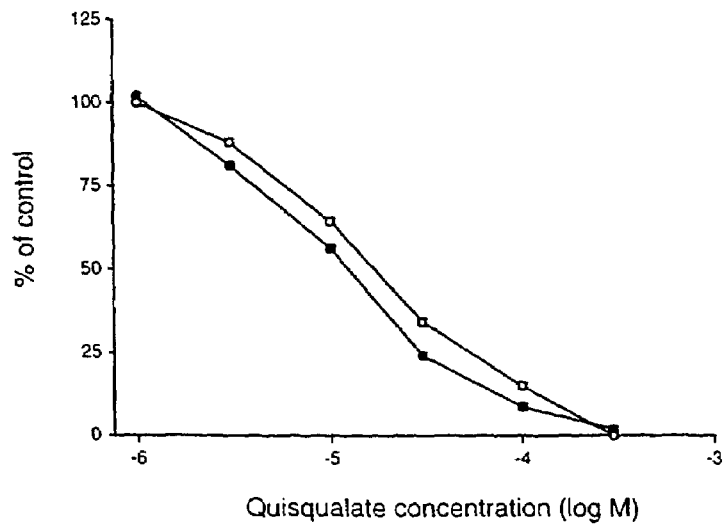
FIG. 9.

FIG. 10.
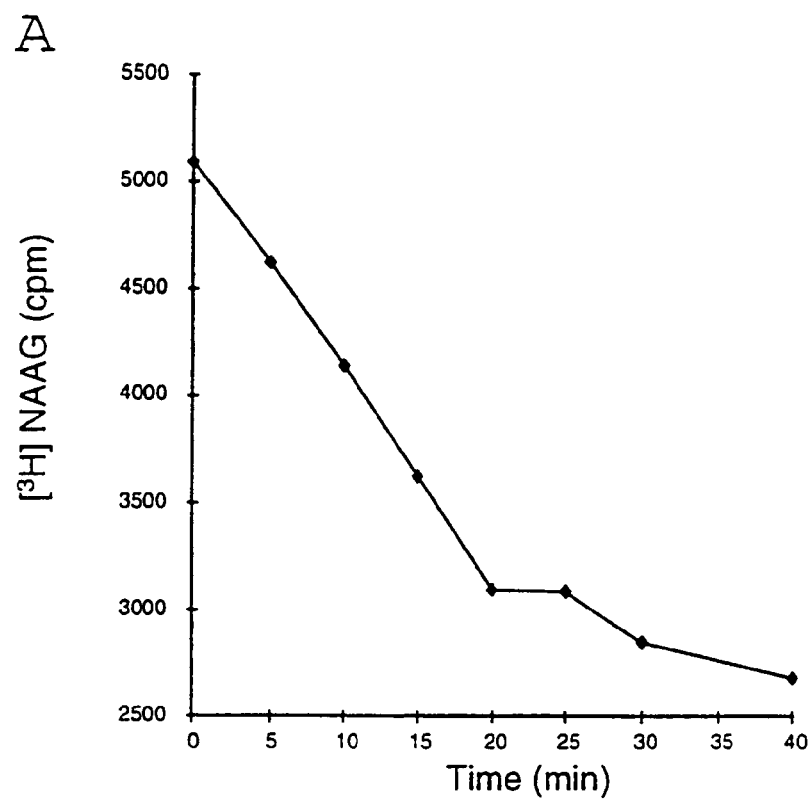
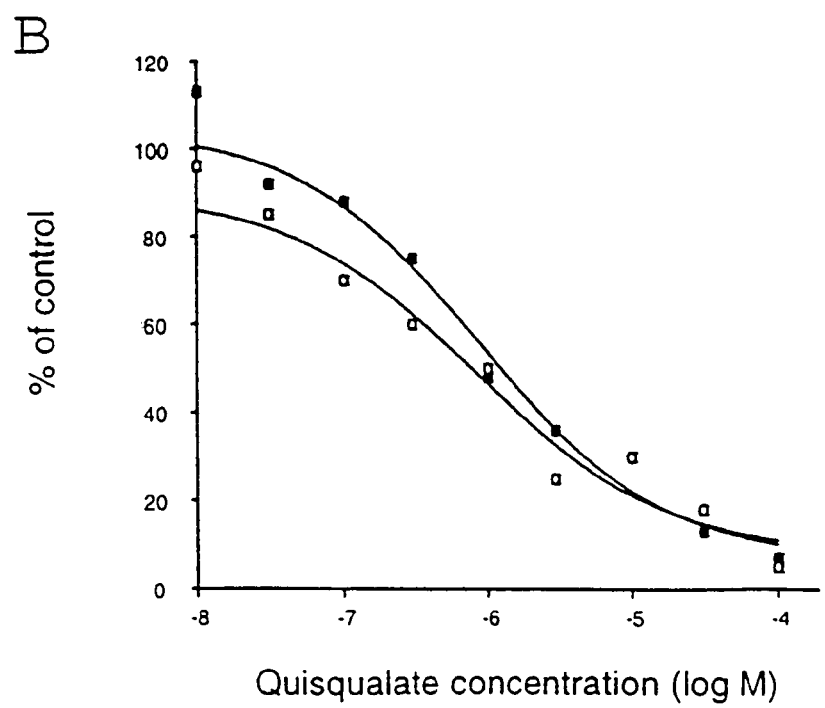

FIG. 11.
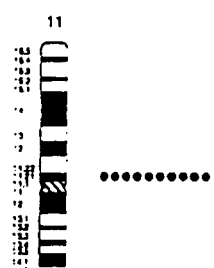
A
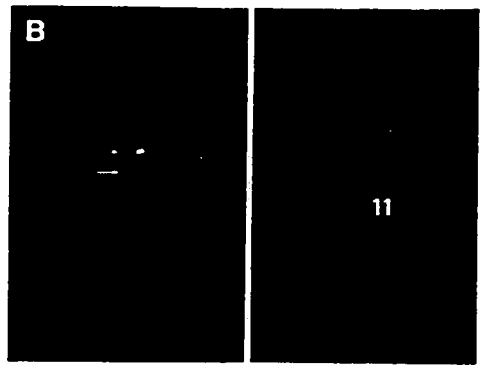
B
C
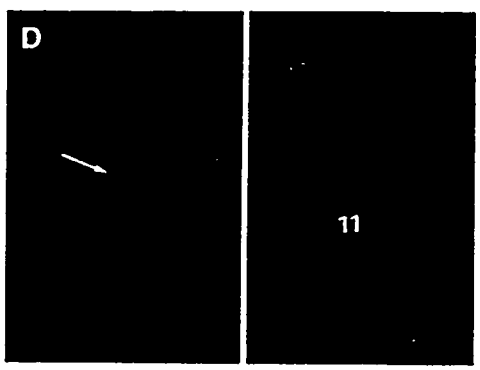
D
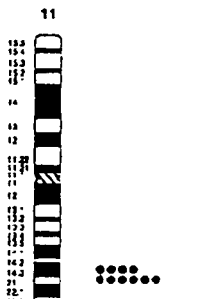
E
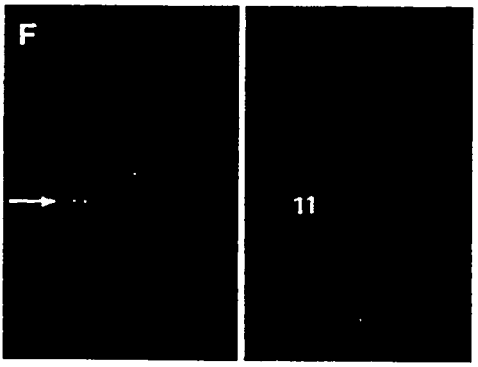
F
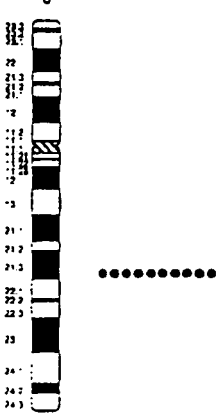
G
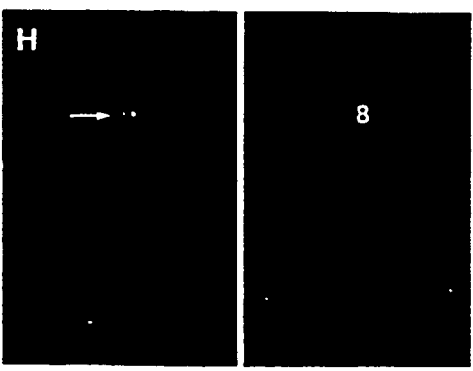
H FIG. 12
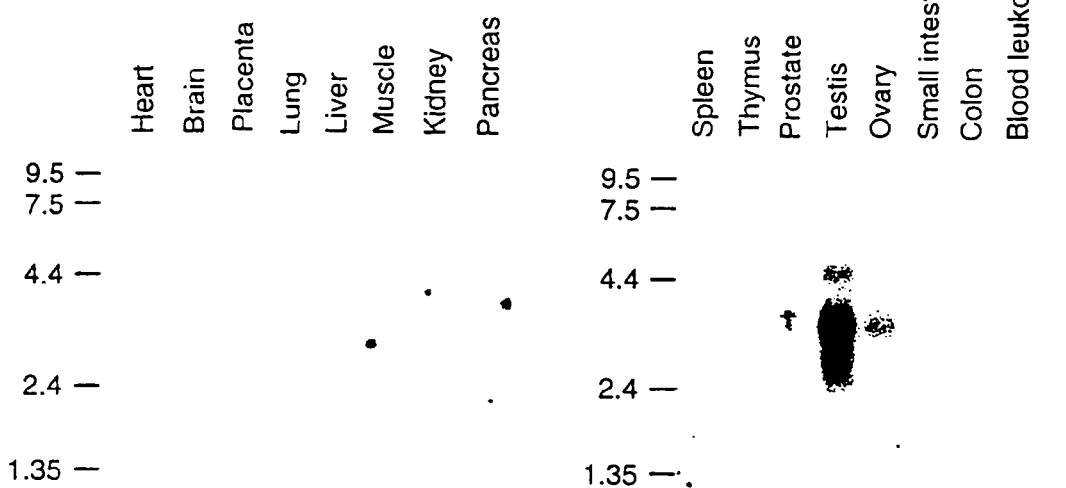
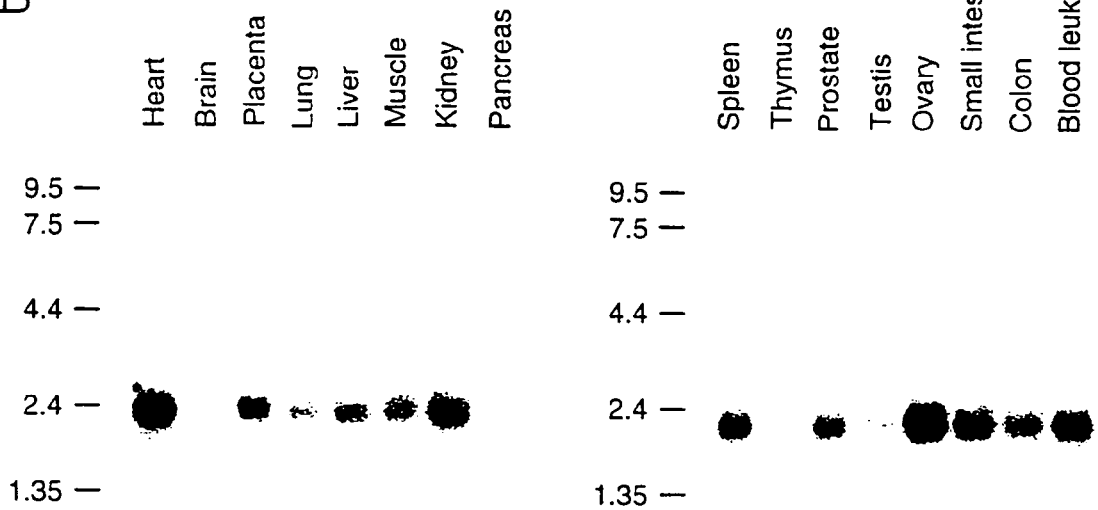

FIG. 13.
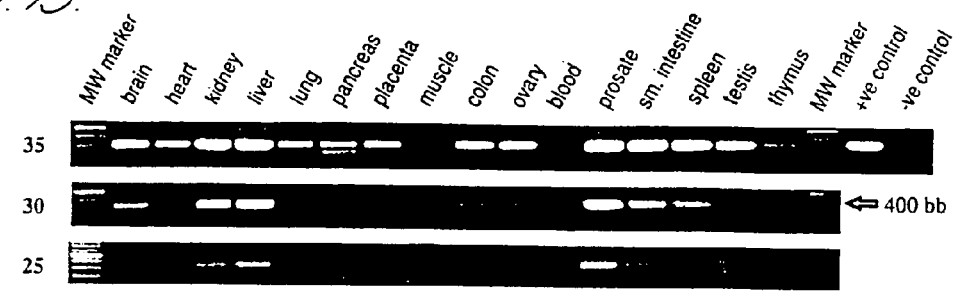
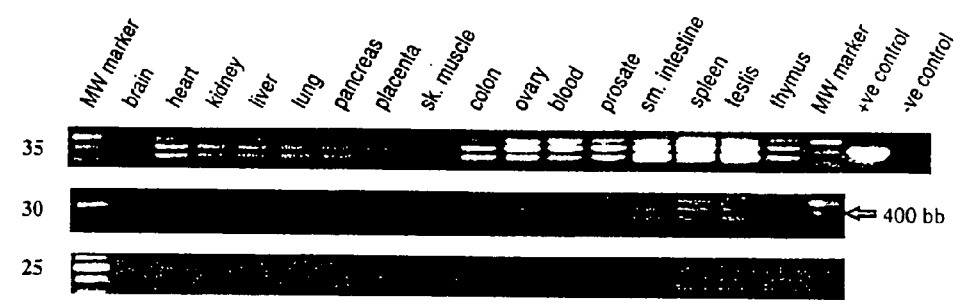
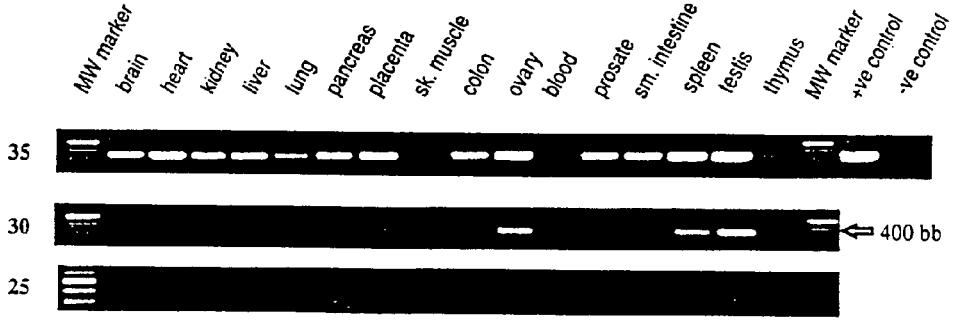
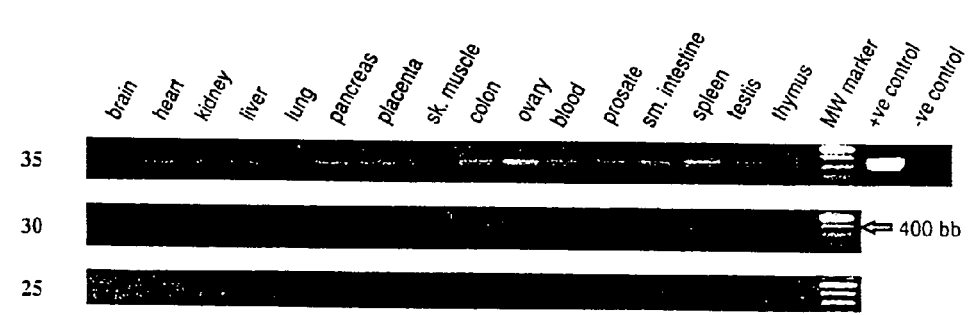
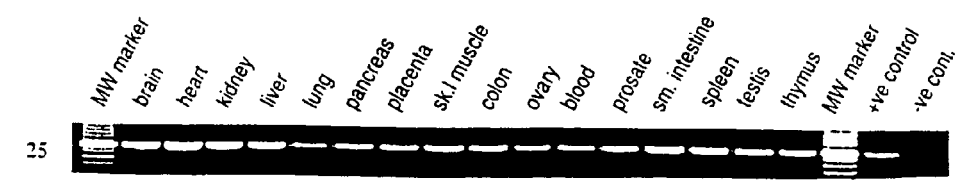

FIG. 14.
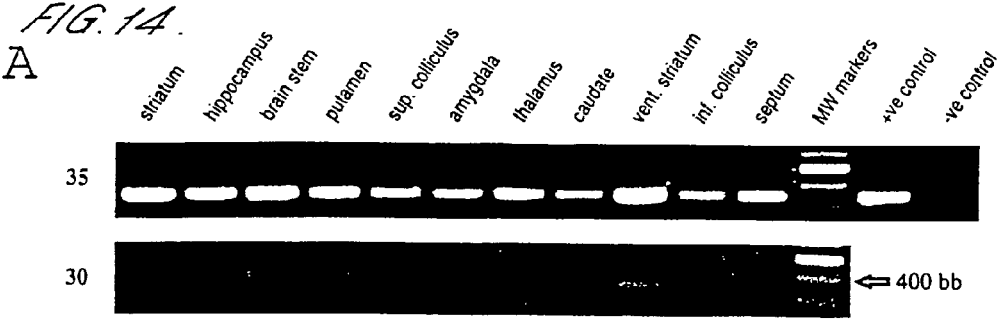
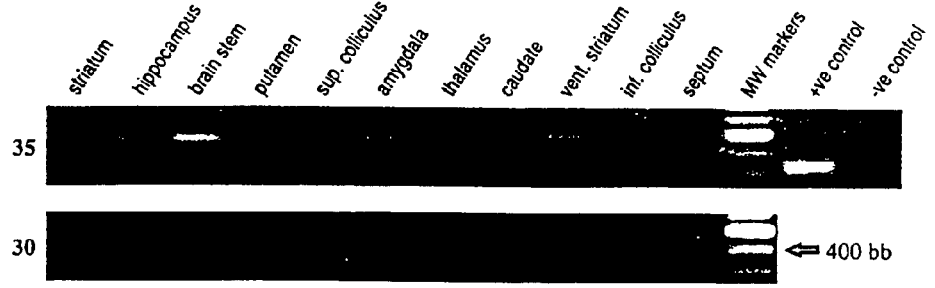
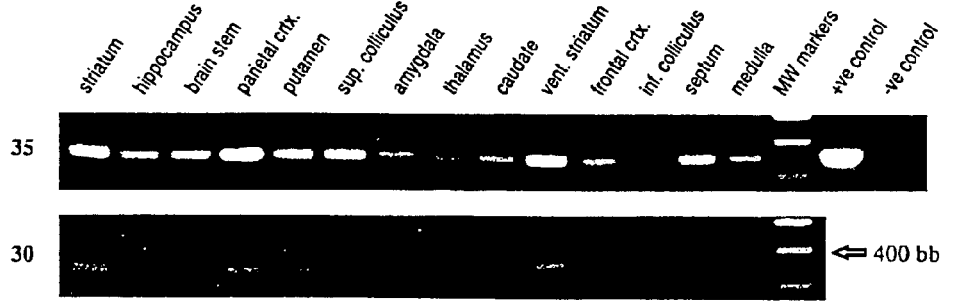
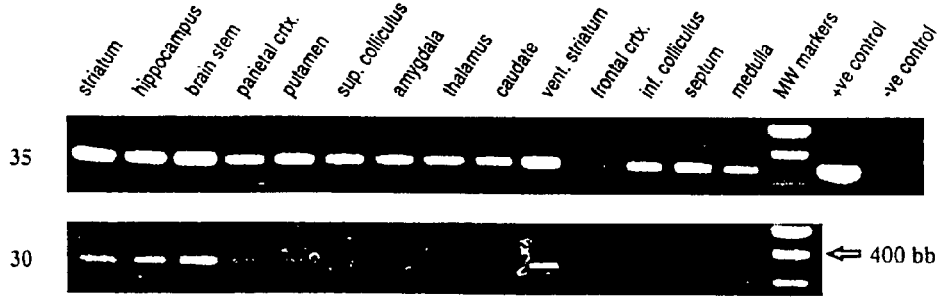
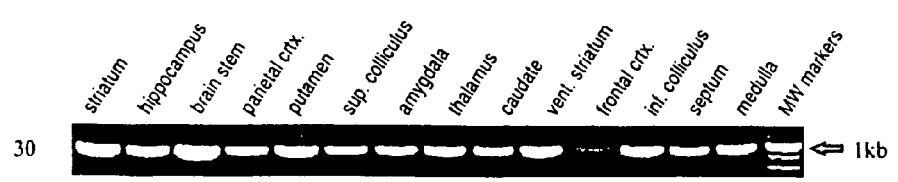

FIG. 15.
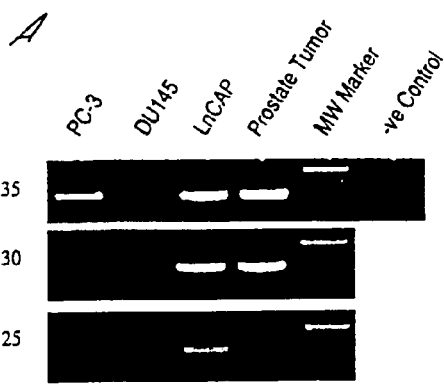
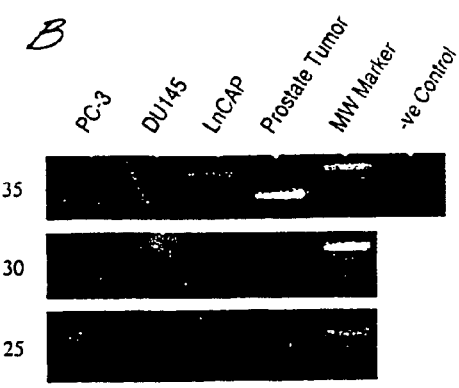
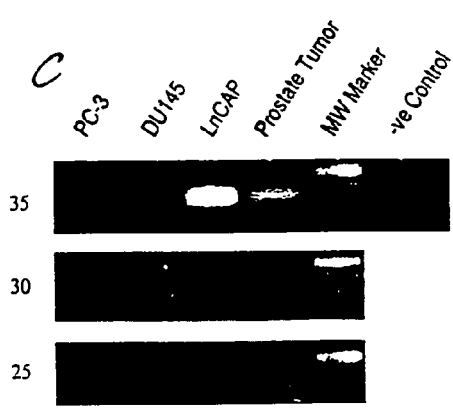
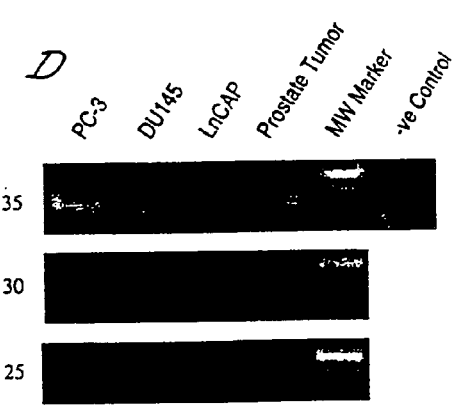
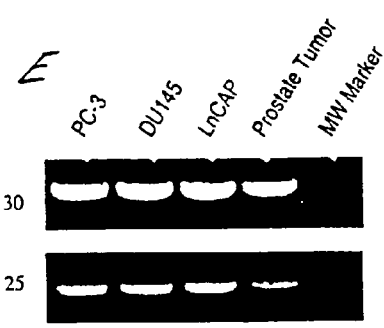

SEQUENCE LISTING

```
<160> NUMBER OF SEQ ID NOS: 69

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 1
cccggatccg agatgtggat tctccttcac gaaac                                 35

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 2
cccctcgagt taggctactt cactcaaagt ctctgc                                36

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence:  Synthetic
      primer
```

-continued

```
<400> SEQUENCE: 3
ccctcagagt ggagcagctg ttgttcatga aattgtgagg                    40

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cctcacaatt tcatgaacaa cagctgctcc actctgaggg                    40

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gttcttcaac aagctgcagg agcg                                     24

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cccctcgagc cggagtaaag ggagggctga ag                            32

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggcgacctga gcatctacga caac                                     24

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cccctcgagt ccctcagag gtcagccaca g                              31

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
```
gccagcaccc agagaaccca ag                                              22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gctgcggttg aagtaccgga tc                                              22

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccatcctaat acgactcact atagggc                                         27

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
actcactata gggctcgagc ggc                                             23

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tgtaaaacga cggccagt                                                   18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
caggaaacag ctatgacc                                                   18

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

-continued

```
ctgcagcttg ttgaactctt ctgtg                                          25
```

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

```
caaacacgat tgatctgcga ggac                                           24
```

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

```
cggatatccg caggatgcag tggacgaag                                      29
```

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

```
caaacacaat tgatctgcga ggacgc                                         26
```

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

```
gcgtcctcgc agatcaattg tgtttg                                         26
```

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

```
ctttgatgat agcgcacaga agtgg                                          25
```

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

```
ggaaagatgc cagcgcagga c                                              21
```

```
<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cgtcagagcc gccctatcag attatc                                          26

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gaggagtttt ccaaagttgc agaccc                                          26

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gggaaacaaa caaattcagc ggc                                             23

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gtcaaagtcc tggagtctct cactgaac                                        28

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gaccggagca agacttcagc cag                                             23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gtgttgatat gcgttggccc aag                                             23
```

```
<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cactaagaat aagaaaacag ataagtacag c                                31

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gatcaacttg tataagtcgt ttatgaaaat ctg                              33

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gcagaagaac aaggtggagt tggtg                                       25

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gctttggatc catgacagtc atgg                                        24

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tgaaggtcgg agtcaacgga tttggt                                      26

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
catgtgggcc atgaggtcca ccac                                        24
```

-continued

```
<210> SEQ ID NO 34
<211> LENGTH: 2320
<212> TYPE: DNA
<213> ORGANISM: Homo sapiens
<220> FEATURE:
<221> NAME/KEY: modified_base
<222> LOCATION: (315)
<223> OTHER INFORMATION: a, c, g, t, unknown or other
<220> FEATURE:
<221> NAME/KEY: CDS
<222> LOCATION: (17)..(2236)

<400> SEQUENCE: 34
gccaagagtc cgcagg atg cag tgg acg aag gtg ttg ggg ctg ggg ctg ggg      52
               Met Gln Trp Thr Lys Val Leu Gly Leu Gly Leu Gly
                 1               5                  10 gct gct gcc ctc ttg ggg ctg ggg atc atc ctc ggc cac ttt gcc atc      100
Ala Ala Ala Leu Leu Gly Leu Gly Ile Ile Leu Gly His Phe Ala Ile
         15                  20                  25 ccc aaa aaa gcc aac tca ctg gcc ccc cag gac ctg gac ctg gag atc      148
Pro Lys Lys Ala Asn Ser Leu Ala Pro Gln Asp Leu Asp Leu Glu Ile
 30                  35                  40 ctg gag acc gtc atg ggg cag ctg gat gcc cac agg atc cgg gag aac      196
Leu Glu Thr Val Met Gly Gln Leu Asp Ala His Arg Ile Arg Glu Asn
 45                  50                  55                  60 ctc aga gaa ctc tcc agg gag cca cac ctg gcc tcc agc cct cgg gat      244
Leu Arg Glu Leu Ser Arg Glu Pro His Leu Ala Ser Ser Pro Arg Asp
             65                  70                  75 gag gac ctg gtg cag ctg ctg ctg cag cgc tgg aag gac cca gag tca      292
Glu Asp Leu Val Gln Leu Leu Leu Gln Arg Trp Lys Asp Pro Glu Ser
         80                  85                  90 ggc ctg gac tcg gcc gag gcc tnc acg tac gaa gtg ctg ctg tcc ttc      340
Gly Leu Asp Ser Ala Glu Ala Xaa Thr Tyr Glu Val Leu Leu Ser Phe
         95                 100                 105 cct agc cag gag cag ccc aac gtc gtg gac atc gtg ggc ccc act ggg      388
Pro Ser Gln Glu Gln Pro Asn Val Val Asp Ile Val Gly Pro Thr Gly
    110                 115                 120 ggc atc atc cac tcc tgc cac cgg act gag gag aac gtg acc ggg gag      436
Gly Ile Ile His Ser Cys His Arg Thr Glu Glu Asn Val Thr Gly Glu
125                 130                 135                 140 caa ggg ggg cca gat gtg gta caa ccc tat gct gcc tat gct cct tct      484
Gln Gly Gly Pro Asp Val Val Gln Pro Tyr Ala Ala Tyr Ala Pro Ser
                145                 150                 155 gga acc cca cag ggc ctc ctc gtc tat gcc aac cgg ggc gcg gaa gaa      532
Gly Thr Pro Gln Gly Leu Leu Val Tyr Ala Asn Arg Gly Ala Glu Glu
            160                 165                 170 gac ttt aag gag cta cag act cag ggc atc aaa ctt gaa ggc acc att      580
Asp Phe Lys Glu Leu Gln Thr Gln Gly Ile Lys Leu Glu Gly Thr Ile
        175                 180                 185 gcc ctg act cga tat ggg ggt gta ggg cgt ggg gcc aag gct gtg aac      628
Ala Leu Thr Arg Tyr Gly Gly Val Gly Arg Gly Ala Lys Ala Val Asn
    190                 195                 200 gct gcc aag cac ggg gta gct ggg gtg ctg gtg tac aca gac cct gcc      676
Ala Ala Lys His Gly Val Ala Gly Val Leu Val Tyr Thr Asp Pro Ala
205                 210                 215                 220 gac atc aac gat ggg ctg agc tca ccc gac gaa acc ttt ccc aac tcc      724
Asp Ile Asn Asp Gly Leu Ser Ser Pro Asp Glu Thr Phe Pro Asn Ser
                225                 230                 235 tgg tac ctg ccc ccc tca gga gtg gag cga ggc tcc tac tac gag tat      772
Trp Tyr Leu Pro Pro Ser Gly Val Glu Arg Gly Ser Tyr Tyr Glu Tyr
            240                 245                 250 ttt ggg gac cct ctg act ccc tac ctt cca gcc gtc ccc tct tcc ttc      820
```

|   |   |
|---|---|
| Phe Gly Asp Pro Leu Thr Pro Tyr Leu Pro Ala Val Pro Ser Ser Phe<br>     255                 260                265 |   |
| cgc gtg gac ctt gcc aat gtc tcc gga ttt ccc cca att cct aca cag<br>Arg Val Asp Leu Ala Asn Val Ser Gly Phe Pro Pro Ile Pro Thr Gln<br>     270                 275                280 | 868 |
| ccc att ggc ttc cag gat gca aga gac ctg ctc tgt aac ctc aac gga<br>Pro Ile Gly Phe Gln Asp Ala Arg Asp Leu Leu Cys Asn Leu Asn Gly<br>285                290                295                300 | 916 |
| act ttg gcc cca gcc acc tgg cag gga gca ctg ggc tgc cac tac agg<br>Thr Leu Ala Pro Ala Thr Trp Gln Gly Ala Leu Gly Cys His Tyr Arg<br>                  305                310                315 | 964 |
| ttg ggt ccc ggc ttc cgg cct gac gga gac ttc cca gca gac agc cag<br>Leu Gly Pro Gly Phe Arg Pro Asp Gly Asp Phe Pro Ala Asp Ser Gln<br>          320                325                330 | 1012 |
| gtg aat gtg agc gtc tac aac cgc ctg gag ctg agg aac tct tcc aac<br>Val Asn Val Ser Val Tyr Asn Arg Leu Glu Leu Arg Asn Ser Ser Asn<br>     335                 340                345 | 1060 |
| gtc ctg ggc atc atc cgt ggg gct gtg gag cct gat cgc tac gtg ctg<br>Val Leu Gly Ile Ile Arg Gly Ala Val Glu Pro Asp Arg Tyr Val Leu<br>          350                355                360 | 1108 |
| tat ggg aac cac cga gac agc tgg gtg cac ggg gct gtg gac ccc agc<br>Tyr Gly Asn His Arg Asp Ser Trp Val His Gly Ala Val Asp Pro Ser<br>365                370                375                380 | 1156 |
| agt ggc acc gcc gtc ctc ctg gag ctc tcc cgt gtc ctg ggg acc ctg<br>Ser Gly Thr Ala Val Leu Leu Glu Leu Ser Arg Val Leu Gly Thr Leu<br>                  385                390                395 | 1204 |
| ctg aag aag ggc acc tgg cgt cct cgc aga tca atc gtg ttt gcg agc<br>Leu Lys Lys Gly Thr Trp Arg Pro Arg Arg Ser Ile Val Phe Ala Ser<br>          400                405                410 | 1252 |
| tgg ggg gct gag gag ttt ggg ctc att ggc tcc acg gaa ttc aca gaa<br>Trp Gly Ala Glu Glu Phe Gly Leu Ile Gly Ser Thr Glu Phe Thr Glu<br>                  415                420                425 | 1300 |
| gag ttc ttc aac aag ctg cag gag cgc acg gtg gcc tac atc aac gtg<br>Glu Phe Phe Asn Lys Leu Gln Glu Arg Thr Val Ala Tyr Ile Asn Val<br>          430                435                440 | 1348 |
| gac atc tcg gtg ttt gcc aac gct acc ctt agg gtg cag ggg acg ccc<br>Asp Ile Ser Val Phe Ala Asn Ala Thr Leu Arg Val Gln Gly Thr Pro<br>445                450                455                460 | 1396 |
| cct gtc cag agc gtc gtc ttc tct gca acc aaa gag atc cgc tca cca<br>Pro Val Gln Ser Val Val Phe Ser Ala Thr Lys Glu Ile Arg Ser Pro<br>                  465                470                475 | 1444 |
| ggc cct ggc gac ctg agc atc tac gac aac tgg atc cgg tac ttc aac<br>Gly Pro Gly Asp Leu Ser Ile Tyr Asp Asn Trp Ile Arg Tyr Phe Asn<br>                  480                485                490 | 1492 |
| cgc agc agc ccg gtg tac ggc ctg gtc ccc agc ttg ggt tct ctg ggt<br>Arg Ser Ser Pro Val Tyr Gly Leu Val Pro Ser Leu Gly Ser Leu Gly<br>          495                500                505 | 1540 |
| gct ggc agc gac tat gca ccc ttc gtt cac ttc ctg ggc atc tcc tcc<br>Ala Gly Ser Asp Tyr Ala Pro Phe Val His Phe Leu Gly Ile Ser Ser<br>                  510                515                520 | 1588 |
| atg gac att gcc tat acc tat gac cgg agc aag act tca gcc agg atc<br>Met Asp Ile Ala Tyr Thr Tyr Asp Arg Ser Lys Thr Ser Ala Arg Ile<br>525                530                535                540 | 1636 |
| tac ccc acc tac cac aca gcc ttt gac acc ttt gac tat gtg gac aag<br>Tyr Pro Thr Tyr His Thr Ala Phe Asp Thr Phe Asp Tyr Val Asp Lys<br>                  545                550                555 | 1684 |
| ttt ttg gac ccg ggc ttc agc agc cat cag gct gtg gcc cgg aca gcg<br>Phe Leu Asp Pro Gly Phe Ser Ser His Gln Ala Val Ala Arg Thr Ala<br>          560                565                570 | 1732 |

-continued

```
ggg agt gtg att ctc cgg ctc agt gac agc ttc ttc ctg ccc ctc aaa    1780
Gly Ser Val Ile Leu Arg Leu Ser Asp Ser Phe Phe Leu Pro Leu Lys
            575                 580                 585 gtc agt gac tac agt gag aca ctc cgc agc ttc ctg cag gca gcc cag    1828
Val Ser Asp Tyr Ser Glu Thr Leu Arg Ser Phe Leu Gln Ala Ala Gln
        590                 595                 600 caa gat ctt ggg gcc ctg ctg gag cag cac agc atc agc ctg ggg cct    1876
Gln Asp Leu Gly Ala Leu Leu Glu Gln His Ser Ile Ser Leu Gly Pro
605                 610                 615                 620 ctg gtg act gca gtg gag aag ttt gag gca gaa gct gca gcc ttg ggc    1924
Leu Val Thr Ala Val Glu Lys Phe Glu Ala Glu Ala Ala Ala Leu Gly
                625                 630                 635 caa cgc ata tca aca ctg cag aag ggc agc cct gac ccc ctg cag gtc    1972
Gln Arg Ile Ser Thr Leu Gln Lys Gly Ser Pro Asp Pro Leu Gln Val
            640                 645                 650 cgg atg ctc aat gac cag ttg atg ctc ttg gaa cgg acc ttt ctg aac    2020
Arg Met Leu Asn Asp Gln Leu Met Leu Leu Glu Arg Thr Phe Leu Asn
        655                 660                 665 cct aga gcc ttc cca gag gaa cgc tac tac agc cat gtg ctc tgg gca    2068
Pro Arg Ala Phe Pro Glu Glu Arg Tyr Tyr Ser His Val Leu Trp Ala
670                 675                 680 cct tcg cac ggg ctc cgt agt cac att ccg ggg cta tcc aat gcc tgc    2116
Pro Ser His Gly Leu Arg Ser His Ile Pro Gly Leu Ser Asn Ala Cys
685                 690                 695                 700 tcc agg gcc agg gac aca gct tct gga tct gaa gct tgg gct gag gtc    2164
Ser Arg Ala Arg Asp Thr Ala Ser Gly Ser Glu Ala Trp Ala Glu Val
                705                 710                 715 cag aga cag ctc agc att gtg gtg aca gcc ctg gag ggt gcg gca gcc    2212
Gln Arg Gln Leu Ser Ile Val Val Thr Ala Leu Glu Gly Ala Ala Ala
            720                 725                 730 acc ctg agg cct gtg gct gac ctc tgaccccagc cctctttctt cagccctccc   2266
Thr Leu Arg Pro Val Ala Asp Leu
        735                 740 tttactccgg tgctttatat ttacaaagtg ctttgtgttt tttaaaagtc tttt         2320
```

<210> SEQ ID NO 35
<211> LENGTH: 740
<212> TYPE: PRT
<213> ORGANISM: Homo sapiens
<220> FEATURE:
<221> NAME/KEY: MOD_RES
<222> LOCATION: (100)
<223> OTHER INFORMATION: variable amino acid

<400> SEQUENCE: 35

```
Met Gln Trp Thr Lys Val Leu Gly Leu Gly Leu Gly Ala Ala Ala Leu
 1               5                  10                  15

Leu Gly Leu Gly Ile Ile Leu Gly His Phe Ala Ile Pro Lys Lys Ala
            20                  25                  30

Asn Ser Leu Ala Pro Gln Asp Leu Asp Leu Glu Ile Leu Glu Thr Val
        35                  40                  45

Met Gly Gln Leu Asp Ala His Arg Ile Arg Glu Asn Leu Arg Glu Leu
    50                  55                  60

Ser Arg Glu Pro His Leu Ala Ser Ser Pro Arg Asp Glu Asp Leu Val
65                  70                  75                  80

Gln Leu Leu Leu Gln Arg Trp Lys Asp Pro Glu Ser Gly Leu Asp Ser
                85                  90                  95

Ala Glu Ala Xaa Thr Tyr Glu Val Leu Leu Ser Phe Pro Ser Gln Glu
            100                 105                 110
```

```
Gln Pro Asn Val Val Asp Ile Val Gly Pro Thr Gly Gly Ile Ile His
        115                 120                 125

Ser Cys His Arg Thr Glu Glu Asn Val Thr Gly Glu Gln Gly Gly Pro
        130                 135                 140

Asp Val Val Gln Pro Tyr Ala Ala Tyr Ala Pro Ser Gly Thr Pro Gln
145                 150                 155                 160

Gly Leu Leu Val Tyr Ala Asn Arg Gly Ala Glu Glu Asp Phe Lys Glu
                165                 170                 175

Leu Gln Thr Gln Gly Ile Lys Leu Glu Gly Thr Ile Ala Leu Thr Arg
            180                 185                 190

Tyr Gly Gly Val Gly Arg Gly Ala Lys Ala Val Asn Ala Ala Lys His
        195                 200                 205

Gly Val Ala Gly Val Leu Val Tyr Thr Asp Pro Ala Asp Ile Asn Asp
    210                 215                 220

Gly Leu Ser Ser Pro Asp Glu Thr Phe Pro Asn Ser Trp Tyr Leu Pro
225                 230                 235                 240

Pro Ser Gly Val Glu Arg Gly Ser Tyr Tyr Glu Tyr Phe Gly Asp Pro
                245                 250                 255

Leu Thr Pro Tyr Leu Pro Ala Val Pro Ser Ser Phe Arg Val Asp Leu
            260                 265                 270

Ala Asn Val Ser Gly Phe Pro Pro Ile Pro Thr Gln Pro Ile Gly Phe
        275                 280                 285

Gln Asp Ala Arg Asp Leu Leu Cys Asn Leu Asn Gly Thr Leu Ala Pro
    290                 295                 300

Ala Thr Trp Gln Gly Ala Leu Gly Cys His Tyr Arg Leu Gly Pro Gly
305                 310                 315                 320

Phe Arg Pro Asp Gly Asp Phe Pro Ala Asp Ser Gln Val Asn Val Ser
                325                 330                 335

Val Tyr Asn Arg Leu Glu Leu Arg Asn Ser Ser Asn Val Leu Gly Ile
            340                 345                 350

Ile Arg Gly Ala Val Glu Pro Asp Arg Tyr Val Leu Tyr Gly Asn His
        355                 360                 365

Arg Asp Ser Trp Val His Gly Ala Val Asp Pro Ser Ser Gly Thr Ala
    370                 375                 380

Val Leu Leu Glu Leu Ser Arg Val Leu Gly Thr Leu Leu Lys Lys Gly
385                 390                 395                 400

Thr Trp Arg Pro Arg Arg Ser Ile Val Phe Ala Ser Trp Gly Ala Glu
                405                 410                 415

Glu Phe Gly Leu Ile Gly Ser Thr Glu Phe Thr Glu Glu Phe Phe Asn
            420                 425                 430

Lys Leu Gln Glu Arg Thr Val Ala Tyr Ile Asn Val Asp Ile Ser Val
        435                 440                 445

Phe Ala Asn Ala Thr Leu Arg Val Gln Gly Thr Pro Pro Val Gln Ser
    450                 455                 460

Val Val Phe Ser Ala Thr Lys Glu Ile Arg Ser Pro Gly Pro Gly Asp
465                 470                 475                 480

Leu Ser Ile Tyr Asp Asn Trp Ile Arg Tyr Phe Asn Arg Ser Ser Pro
                485                 490                 495

Val Tyr Gly Leu Val Pro Ser Leu Gly Ser Leu Gly Ala Gly Ser Asp
            500                 505                 510

Tyr Ala Pro Phe Val His Phe Leu Gly Ile Ser Ser Met Asp Ile Ala
        515                 520                 525

Tyr Thr Tyr Asp Arg Ser Lys Thr Ser Ala Arg Ile Tyr Pro Thr Tyr
```

-continued

```
            530                 535                 540
His Thr Ala Phe Asp Thr Phe Asp Tyr Val Asp Lys Phe Leu Asp Pro
545                 550                 555                 560

Gly Phe Ser Ser His Gln Ala Val Ala Arg Thr Ala Gly Ser Val Ile
                565                 570                 575

Leu Arg Leu Ser Asp Ser Phe Phe Leu Pro Leu Lys Val Ser Asp Tyr
                580                 585                 590

Ser Glu Thr Leu Arg Ser Phe Leu Gln Ala Ala Gln Gln Asp Leu Gly
                595                 600                 605

Ala Leu Leu Glu Gln His Ser Ile Ser Leu Gly Pro Leu Val Thr Ala
                610                 615                 620

Val Glu Lys Phe Glu Ala Glu Ala Ala Leu Gly Gln Arg Ile Ser
625                 630                 635                 640

Thr Leu Gln Lys Gly Ser Pro Asp Pro Leu Gln Val Arg Met Leu Asn
                645                 650                 655

Asp Gln Leu Met Leu Leu Glu Arg Thr Phe Leu Asn Pro Arg Ala Phe
                660                 665                 670

Pro Glu Glu Arg Tyr Tyr Ser His Val Leu Trp Ala Pro Ser His Gly
                675                 680                 685

Leu Arg Ser His Ile Pro Gly Leu Ser Asn Ala Cys Ser Arg Ala Arg
                690                 695                 700

Asp Thr Ala Ser Gly Ser Glu Ala Trp Ala Glu Val Gln Arg Gln Leu
705                 710                 715                 720

Ser Ile Val Val Thr Ala Leu Glu Gly Ala Ala Thr Leu Arg Pro
                725                 730                 735

Val Ala Asp Leu
                740

<210> SEQ ID NO 36
<211> LENGTH: 745
<212> TYPE: PRT
<213> ORGANISM: Rattus rattus

<400> SEQUENCE: 36

Met His Trp Ala Lys Ile Leu Gly Val Gly Ile Gly Ala Ala Ala Leu
  1               5                  10                  15

Leu Gly Leu Gly Ile Ile Leu Gly His Phe Ala Ile Pro Lys Ala Thr
                20                  25                  30

Glu Pro Leu Ala Ser Ser Val Ser Asp Ser Gln Asp Leu Asp Leu Ala
            35                  40                  45

Ile Leu Asp Ser Val Met Gly Gln Leu Asp Ala Ser Arg Ile Arg Glu
 50                  55                  60

Asn Leu Arg Glu Leu Ser Lys Glu Pro His Val Ala Thr Ser Ala Arg
 65                  70                  75                  80

Asp Glu Ala Leu Val Gln Leu Leu Gly Arg Trp Lys Asp Ser Ala
                85                  90                  95

Ser Gly Leu Asp Thr Ala Lys Thr Tyr Glu Tyr Thr Val Leu Leu Ser
            100                 105                 110

Phe Pro Ser Thr Glu Gln Pro Asn Ser Val Glu Val Val Gly Pro Asn
            115                 120                 125

Gly Thr Val Phe His Ser Phe Gln Pro Phe Glu Lys Asn Leu Thr Gly
            130                 135                 140

Glu Gln Ala Glu Pro Asn Val Leu Gln Pro Tyr Ala Ala Tyr Ala Pro
145                 150                 155                 160
```

-continued

```
Pro Gly Thr Pro Lys Gly Pro Leu Val Tyr Ala Asn Arg Gly Ser Glu
            165                 170                 175

Asp Asp Phe Lys Lys Leu Glu Ala Glu Gly Ile Asn Leu Lys Gly Thr
        180                 185                 190

Ile Ala Leu Thr Arg Tyr Gly Ser Val Gly Arg Gly Ala Lys Ala Ile
            195                 200                 205

Asn Ala Ala Arg His Gly Val Val Gly Val Leu Val Tyr Thr Asp Pro
    210                 215                 220

Gly Asp Ile Asn Asp Gly Lys Ser Leu Pro Asn Glu Thr Phe Pro Asn
225                 230                 235                 240

Ser Trp Gly Leu Pro Pro Ser Gly Val Glu Arg Gly Ser Tyr Tyr Glu
                245                 250                 255

Tyr Phe Gly Asp Pro Leu Thr Pro Tyr Leu Pro Ala His Pro Val Ser
            260                 265                 270

Phe Arg Leu Asp Pro His Asn Ile Ser Gly Phe Pro Pro Ile Pro Thr
        275                 280                 285

Gln Pro Ile Gly Phe Glu Asp Ala Lys Asn Leu Leu Cys Asn Leu Asn
    290                 295                 300

Gly Thr Ser Ala Pro Asp Ser Trp Gln Gly Ala Leu Gly Cys Glu Tyr
305                 310                 315                 320

Lys Leu Gly Pro Gly Phe Glu Pro Asn Gly Asn Phe Pro Ala Gly Ser
                325                 330                 335

Glu Val Lys Val Ser Val Tyr Asn Arg Leu Glu Leu Arg Asn Ser Ser
            340                 345                 350

Asn Val Leu Gly Ile Ile Gln Gly Ala Val Glu Pro Asp Arg Tyr Val
        355                 360                 365

Ile Tyr Gly Asn His Arg Asp Ser Trp Val His Gly Ala Val Asp Pro
    370                 375                 380

Ser Ser Gly Thr Ala Val Leu Leu Glu Ile Ser Arg Val Leu Gly Thr
385                 390                 395                 400

Leu Leu Lys Lys Gly Thr Trp Arg Pro Arg Arg Ser Ile Ile Phe Ala
                405                 410                 415

Ser Trp Gly Ala Glu Glu Phe Gly Leu Ile Gly Ser Thr Glu Phe Thr
            420                 425                 430

Glu Glu Phe Leu Ser Lys Leu Gln Glu Arg Thr Val Thr Tyr Ile Asn
        435                 440                 445

Val Asp Ile Ser Val Phe Ser Asn Ala Thr Leu Arg Ala Gln Gly Thr
    450                 455                 460

Pro Pro Val Gln Ser Val Ile Phe Ser Ala Thr Lys Glu Ile Ser Ala
465                 470                 475                 480

Pro Gly Ser Ser Gly Leu Ser Ile Tyr Asp Asn Trp Ile Arg Tyr Thr
                485                 490                 495

Asn Arg Ser Ser Pro Val Tyr Gly Leu Val Pro Ser Met Gly Thr Leu
            500                 505                 510

Gly Ala Gly Ser Asp Tyr Ala Ser Phe Ile His Phe Leu Gly Ile Thr
        515                 520                 525

Ser Met Asp Leu Ala Tyr Thr Tyr Asp Arg Ser Lys Thr Ser Ala Arg
    530                 535                 540

Ile Tyr Pro Thr Tyr His Thr Ala Phe Asp Thr Phe Asp Tyr Val Glu
545                 550                 555                 560

Lys Phe Leu Asp Pro Gly Phe Ser Ser His Gln Ala Val Ala Arg Thr
                565                 570                 575

Ala Gly Ser Val Leu Leu Arg Leu Ser Asp Ser Leu Phe Leu Pro Leu
```

```
                    580                 585                 590
Asn Val Ser Asp Tyr Ser Glu Thr Leu Gln Ser Phe Leu Gln Ala Ala
            595                 600                 605

Gln Glu Asn Leu Gly Ala Leu Leu Glu Ser His Asn Ile Ser Leu Gly
        610                 615                 620

Pro Leu Val Thr Ala Val Glu Lys Phe Lys Ala Ala Ala Ala Ala Leu
625                 630                 635                 640

Asn Gln His Ile Leu Thr Leu Gln Lys Ser Ser Pro Asp Pro Leu Gln
                645                 650                 655

Val Arg Met Val Asn Asp Gln Leu Met Leu Leu Glu Arg Ala Phe Leu
            660                 665                 670

Asn Pro Arg Ala Phe Pro Glu Glu Arg Tyr Tyr Ser His Val Leu Trp
        675                 680                 685

Ala Pro Asn Thr Ala Ser Val Ala Thr Phe Pro Gly Leu Ala Asn Ala
690                 695                 700

Tyr Ala Arg Ala Gln Glu Ile Asn Ser Gly Ala Glu Ala Trp Ala Glu
705                 710                 715                 720

Val Glu Arg Gln Leu Ser Ile Ala Val Met Ala Leu Glu Gly Ala Ala
                725                 730                 735

Ala Thr Leu Gln Pro Val Thr Asp Leu
            740                 745

<210> SEQ ID NO 37
<211> LENGTH: 41
<212> TYPE: PRT
<213> ORGANISM: Homo sapiens

<400> SEQUENCE: 37

Gly Leu Leu Val Tyr Ala Asn Arg Gly Ala Glu Glu Asp Phe Lys Glu
1               5                   10                  15

Leu Gln Thr Gln Gly Ile Lys Leu Glu Gly Thr Ile Ala Leu Thr Arg
            20                  25                  30

Tyr Gly Gly Val Gly Arg Gly Ala Lys
        35                  40

<210> SEQ ID NO 38
<211> LENGTH: 35
<212> TYPE: PRT
<213> ORGANISM: Homo sapiens

<400> SEQUENCE: 38

Cys Asn Leu Asn Gly Thr Leu Ala Pro Ala Thr Trp Gln Gly Ala Leu
1               5                   10                  15

Gly Cys His Tyr Arg Leu Gly Pro Gly Phe Arg Pro Asp Gly Asp Phe
            20                  25                  30

Pro Ala Asp
        35

<210> SEQ ID NO 39
<211> LENGTH: 20
<212> TYPE: PRT
<213> ORGANISM: Homo sapiens

<400> SEQUENCE: 39

Arg Leu Gln Gln Pro Ser Gly Cys Gly Pro Asp Ser Gly Glu Cys Asp
1               5                   10                  15

Ser Pro Ala Gln
        20
```

```
<210> SEQ ID NO 40
<211> LENGTH: 41
<212> TYPE: PRT
<213> ORGANISM: Homo sapiens

<400> SEQUENCE: 40

Arg Ala Arg Leu Gln Pro Gly Ser Pro Pro Thr Thr Gln Pro Leu Thr
 1               5                  10                  15

Pro Leu Thr Met Trp Thr Ser Phe Trp Thr Arg Ala Ser Ala Ala Ile
            20                  25                  30

Arg Leu Trp Pro Gly Gln Arg Gly Val
        35                  40

<210> SEQ ID NO 41
<211> LENGTH: 229
<212> TYPE: DNA
<213> ORGANISM: Homo sapiens

<400> SEQUENCE: 41
gtgagcgtct acaaccgcct ggagctgagg aactcttcca acgtcctggg catcatccgt      60
ggggctgtgg agcctggtga gccctcctct tgctgcctgc accccaggcc cctgctctgc     120
tctggatgcc gctgtcctca tccagccctg cccttgccac cacccagccc agctccccct     180
gcccacctct ccctctcctc tggttctctg ccccttttcc tctggccag                 229

<210> SEQ ID NO 42
<211> LENGTH: 51
<212> TYPE: PRT
<213> ORGANISM: Homo sapiens

<400> SEQUENCE: 42

Gly Glu Pro Ser Ser Cys Cys Leu His Pro Arg Pro Leu Leu Cys Ser
 1               5                  10                  15

Gly Cys Arg Cys Pro His Pro Ala Leu Pro Leu Pro Pro Pro Ser Pro
            20                  25                  30

Ala Pro Pro Ala His Leu Ser Leu Ser Ser Gly Ser Leu Pro Leu Phe
        35                  40                  45

Leu Trp Pro
    50

<210> SEQ ID NO 43
<211> LENGTH: 82
<212> TYPE: DNA
<213> ORGANISM: Homo sapiens

<400> SEQUENCE: 43
gtgaggaggg agacaagggg catcctgaga ccaggacagg agaggctgaa gactgagccc      60
tggccttgtc accttgccgc ag                                               82

<210> SEQ ID NO 44
<211> LENGTH: 17
<212> TYPE: PRT
<213> ORGANISM: Homo sapiens

<400> SEQUENCE: 44

Glu Glu Gly Asp Lys Gly His Pro Glu Thr Arg Thr Gly Glu Ala Glu
 1               5                  10                  15

Asp
```

-continued

```
<210> SEQ ID NO 45
<211> LENGTH: 74
<212> TYPE: DNA
<213> ORGANISM: Homo sapiens

<400> SEQUENCE: 45
gtatgcacag ccctgaccct gaggtatggg gagccctgca cccccatgac tgagccactg      60
cttgttcctc acag                                                       74

<210> SEQ ID NO 46
<211> LENGTH: 17
<212> TYPE: PRT
<213> ORGANISM: Homo sapiens

<400> SEQUENCE: 46

Gly Met His Ser Pro Asp Pro Glu Val Trp Gly Ala Leu His Pro His
 1               5                  10                  15

Asp

<210> SEQ ID NO 47
<211> LENGTH: 3110
<212> TYPE: DNA
<213> ORGANISM: Homo sapiens
<220> FEATURE:
<221> NAME/KEY: CDS
<222> LOCATION: (12)..(2231)

<400> SEQUENCE: 47
ctcaagaagc c atg gcg gaa tcc agg ggc cgt ctg tac ctt tgg atg tgc      50
            Met Ala Glu Ser Arg Gly Arg Leu Tyr Leu Trp Met Cys
              1               5                  10 ttg gct gct gcg ctg gca tct ttc ctg atg gga ttt atg gtg ggc tgg      98
Leu Ala Ala Ala Leu Ala Ser Phe Leu Met Gly Phe Met Val Gly Trp
         15                  20                  25 ttt att aag cct ctc aaa gaa aca acc act tct gtg cgc tat cat caa     146
Phe Ile Lys Pro Leu Lys Glu Thr Thr Thr Ser Val Arg Tyr His Gln
 30                  35                  40                  45 agt ata cgg tgg aaa ctg gta tcc gaa atg aaa gct gaa aac atc aaa     194
Ser Ile Arg Trp Lys Leu Val Ser Glu Met Lys Ala Glu Asn Ile Lys
                 50                  55                  60 tca ttt ctt cgt tct ttt aca aag ctt cct cat ctg gca gga aca gaa     242
Ser Phe Leu Arg Ser Phe Thr Lys Leu Pro His Leu Ala Gly Thr Glu
             65                  70                  75 caa aat ttc ttg ctt gcc aag aaa atc caa acc cag tgg aag aaa ttt     290
Gln Asn Phe Leu Leu Ala Lys Lys Ile Gln Thr Gln Trp Lys Lys Phe
         80                  85                  90 gga cta gat tca gcc aag ttg gtt cat tat gat gtc ctc tta tct tac     338
Gly Leu Asp Ser Ala Lys Leu Val His Tyr Asp Val Leu Leu Ser Tyr
 95                 100                 105 ccc aat gag aca aat gcc aac tat ata tcg att gtg gat gaa cat gaa     386
Pro Asn Glu Thr Asn Ala Asn Tyr Ile Ser Ile Val Asp Glu His Glu
                110                 115                 120         125 act gag att ttc aaa aca tca tac ctt gaa cca cca cca gat ggc tat     434
Thr Glu Ile Phe Lys Thr Ser Tyr Leu Glu Pro Pro Pro Asp Gly Tyr
                 130                 135                 140 gag aat gtt aca aat att gtg cca cca tat aat gct ttc tca gcc caa     482
Glu Asn Val Thr Asn Ile Val Pro Pro Tyr Asn Ala Phe Ser Ala Gln
            145                 150                 155 ggc atg cca gag gga gat ctt gta tat gtg aac tat gct cgc act gaa     530
Gly Met Pro Glu Gly Asp Leu Val Tyr Val Asn Tyr Ala Arg Thr Glu
        160                 165                 170
```

-continued

| | | |
|---|---|---|
| gac ttt ttc aaa cta gaa aga gag atg ggc atc aac tgt act ggg aag<br>Asp Phe Phe Lys Leu Glu Arg Glu Met Gly Ile Asn Cys Thr Gly Lys<br>175                        180                    185 | 578 |
| att gtt att gca aga tat gga aaa atc ttc aga gga aat aaa gtt aaa<br>Ile Val Ile Ala Arg Tyr Gly Lys Ile Phe Arg Gly Asn Lys Val Lys<br>190                      195                    200                  205 | 626 |
| aat gcc atg tta gca gga gcc ata gga atc atc ttg tac tca gat cca<br>Asn Ala Met Leu Ala Gly Ala Ile Gly Ile Ile Leu Tyr Ser Asp Pro<br>210                      215                    220 | 674 |
| gct gac tac ttt gct cct gag gta cag cca tat ccc aaa gga tgg aat<br>Ala Asp Tyr Phe Ala Pro Glu Val Gln Pro Tyr Pro Lys Gly Trp Asn<br>225                      230                    235 | 722 |
| ctt cct gga act gca gcc cag aga gga aat gtg tta aat ttg aat ggt<br>Leu Pro Gly Thr Ala Ala Gln Arg Gly Asn Val Leu Asn Leu Asn Gly<br>240                      245                    250 | 770 |
| gct ggt gac cca ctc act cca ggc tat cca gca aaa gaa tac act ttc<br>Ala Gly Asp Pro Leu Thr Pro Gly Tyr Pro Ala Lys Glu Tyr Thr Phe<br>255                      260                    265 | 818 |
| aga ctt gat gtt gaa gaa gga gtg gga atc ccc cga ata cct gta cat<br>Arg Leu Asp Val Glu Glu Gly Val Gly Ile Pro Arg Ile Pro Val His<br>270                      275                    280                  285 | 866 |
| ccc att gga tat aat gat gca gaa ata tta tta cgc tac ttg gga gga<br>Pro Ile Gly Tyr Asn Asp Ala Glu Ile Leu Leu Arg Tyr Leu Gly Gly<br>290                      295                    300 | 914 |
| att gct cca cca gat aag agt tgg aag gga gcc ctt aat gtg agt tat<br>Ile Ala Pro Pro Asp Lys Ser Trp Lys Gly Ala Leu Asn Val Ser Tyr<br>305                      310                    315 | 962 |
| agt atc gga cct ggc ttt aca ggg agt gat tct ttc agg aag gtt aga<br>Ser Ile Gly Pro Gly Phe Thr Gly Ser Asp Ser Phe Arg Lys Val Arg<br>320                      325                    330 | 1010 |
| atg cat gtt tat aac atc aat aaa att aca agg att tac aat gta gtt<br>Met His Val Tyr Asn Ile Asn Lys Ile Thr Arg Ile Tyr Asn Val Val<br>335                      340                    345 | 1058 |
| gga act atc aga gga tct gtg gaa cct gac agg tat gtt att ctg gga<br>Gly Thr Ile Arg Gly Ser Val Glu Pro Asp Arg Tyr Val Ile Leu Gly<br>350                      355                    360                  365 | 1106 |
| ggt cac cgg gac tcc tgg gta ttt gga gct att gac cca acc agt ggg<br>Gly His Arg Asp Ser Trp Val Phe Gly Ala Ile Asp Pro Thr Ser Gly<br>370                      375                    380 | 1154 |
| gtt gct gtt ttg caa gaa att gcc cgg agt ttt gga aaa ctg atg agt<br>Val Ala Val Leu Gln Glu Ile Ala Arg Ser Phe Gly Lys Leu Met Ser<br>385                      390                    395 | 1202 |
| aaa ggc tgg aga cct aga aga act atc att ttt gcc agc tgg gat gca<br>Lys Gly Trp Arg Pro Arg Arg Thr Ile Ile Phe Ala Ser Trp Asp Ala<br>400                      405                    410 | 1250 |
| gaa gaa ttt gga ctt ctg ggt tcc aca gaa tgg gct gag gag aat gtc<br>Glu Glu Phe Gly Leu Leu Gly Ser Thr Glu Trp Ala Glu Glu Asn Val<br>415                      420                    425 | 1298 |
| aaa ata ctc cag gag aga agc att gct tat atc aac tcg gat tca tct<br>Lys Ile Leu Gln Glu Arg Ser Ile Ala Tyr Ile Asn Ser Asp Ser Ser<br>430                      435                    440                  445 | 1346 |
| ata gaa ggc aat tat act ctc aga gtt gac tgt act ccc ctt ctt tac<br>Ile Glu Gly Asn Tyr Thr Leu Arg Val Asp Cys Thr Pro Leu Leu Tyr<br>450                      455                    460 | 1394 |
| caa tta gtg tat aaa ctg aca aaa gag atc ccc agc cct gat gat ggg<br>Gln Leu Val Tyr Lys Leu Thr Lys Glu Ile Pro Ser Pro Asp Asp Gly<br>465                      470                    475 | 1442 |
| ttt gag agt aaa tca ctg tat gaa agc tgg ttg gaa aaa gac cct tca<br>Phe Glu Ser Lys Ser Leu Tyr Glu Ser Trp Leu Glu Lys Asp Pro Ser | 1490 |

```
                  480              485              490
cct gaa aat aaa aat ttg cct aga atc aat aag ctg gga tct gga agt      1538
Pro Glu Asn Lys Asn Leu Pro Arg Ile Asn Lys Leu Gly Ser Gly Ser
495              500              505 gac ttt gaa gct tat ttt cag aga ctt gga att gct tca ggc aga gcc      1586
Asp Phe Glu Ala Tyr Phe Gln Arg Leu Gly Ile Ala Ser Gly Arg Ala
510              515              520              525 cgt tac act aag aat aag aaa aca gat aag tac agc agc tac cca gtg      1634
Arg Tyr Thr Lys Asn Lys Lys Thr Asp Lys Tyr Ser Ser Tyr Pro Val
              530              535              540 tac cac aca att tat gag aca ttt gaa ttg gta gag aaa ttt tat gac      1682
Tyr His Thr Ile Tyr Glu Thr Phe Glu Leu Val Glu Lys Phe Tyr Asp
              545              550              555 ccc aca ttt aaa aaa caa ctt tct gtg gct caa tta cga gga gca ctg      1730
Pro Thr Phe Lys Lys Gln Leu Ser Val Ala Gln Leu Arg Gly Ala Leu
              560              565              570 gta tat gag ctt gtg gat tct aaa atc att cct ttt aat att caa gac      1778
Val Tyr Glu Leu Val Asp Ser Lys Ile Ile Pro Phe Asn Ile Gln Asp
575              580              585 tat gca gaa gct ttg aaa aac tat gca gca agt atc tat aat cta tct      1826
Tyr Ala Glu Ala Leu Lys Asn Tyr Ala Ala Ser Ile Tyr Asn Leu Ser
590              595              600              605 aag aaa cat gat caa caa tta aca gac cat gga gta tca ttt gac tcc      1874
Lys Lys His Asp Gln Gln Leu Thr Asp His Gly Val Ser Phe Asp Ser
              610              615              620 tta ttt tct gct gtg aaa aac ttc tca gag gct gct tca gat ttt cat      1922
Leu Phe Ser Ala Val Lys Asn Phe Ser Glu Ala Ala Ser Asp Phe His
              625              630              635 aaa cga ctt ata caa gtt gat ctt aac aat ccc att gca gtg aga atg      1970
Lys Arg Leu Ile Gln Val Asp Leu Asn Asn Pro Ile Ala Val Arg Met
              640              645              650 atg aat gac caa ctg atg ctc ctg gaa aga gca ttc atc gat cct ctt      2018
Met Asn Asp Gln Leu Met Leu Leu Glu Arg Ala Phe Ile Asp Pro Leu
655              660              665 ggt tta cca gga aag ctg ttc tat agg cac atc ata ttt gct cca agt      2066
Gly Leu Pro Gly Lys Leu Phe Tyr Arg His Ile Ile Phe Ala Pro Ser
670              675              680              685 agc cac aac aaa tat gct gga gaa tca ttt cct gga atc tat gat gct      2114
Ser His Asn Lys Tyr Ala Gly Glu Ser Phe Pro Gly Ile Tyr Asp Ala
              690              695              700 atc ttt gat att gaa aat aaa gcc aac tct cgt ttg gcc tgg aaa gaa      2162
Ile Phe Asp Ile Glu Asn Lys Ala Asn Ser Arg Leu Ala Trp Lys Glu
              705              710              715 gta aag aaa cat att tct att gca gct ttt aca att caa gca gca gca      2210
Val Lys Lys His Ile Ser Ile Ala Ala Phe Thr Ile Gln Ala Ala Ala
              720              725              730 gga act ctg aaa gaa gta tta tagaaggtct caagtggcta gccattaaag         2261
Gly Thr Leu Lys Glu Val Leu
            735              740 gtgttgctaa aagtctgagg ataaaattca cctttctgat aacttatgaa gccagggtgt    2321
tctaaactct tttcatgtca tgttttgatt ataggctttg gtcttttcat ctgcaaagcc    2381
tttttttttt ttgctctttta aaagttaata attatattag caaagtgtta atctaatgaa   2441
gtaaaaaact cctgtgtggc agaaagtaaa agaaaattcc ctaaattata gcaaggaaca    2501
tgaattctca gacattgtga gtgtgggaat gtaaaatggt aaaatcactt ttgaaaacag    2561
tttggcagtt tcctataaag ttaaacatac acttttactt taggactcca gaattccact    2621
tctagttatt tattcaagag aaggaaaaac aatgatcaca gcaatacttg tatgcatgtt    2681
```

-continued

```
cattgcaact taaaagcgta aaaccccaa atgtccatcc acagacgaat gtataaactg    2741
tggtatccat tacacaatag actacttact actcagcaat aaaaatgaag taactttcaa    2801
taaatgcaat attattggca gacattgttg aaggaaaaaa gccagacaaa caactacata    2861
aaatatgttt ctatttagat gaagtggcaa actaatctgt agtgttaaaa attagattag    2921
tgattgcctg ggccaagtgg caggttgggg aggatggctg caaagaagta tgaggaaact    2981
ttctccaata gatgagaatt ttccgtatct tgatctgagt ggcaaattgt aaacttaaaa    3041
tatatataaa atttattgaa agaaaattaa gcctcaataa acgtgattat aaaaaaaaaa    3101
aaaaaaagg                                                            3110
```

<210> SEQ ID NO 48
<211> LENGTH: 740
<212> TYPE: PRT
<213> ORGANISM: Homo sapiens

<400> SEQUENCE: 48

```
Met Ala Glu Ser Arg Gly Arg Leu Tyr Leu Trp Met Cys Leu Ala Ala
 1               5                  10                  15

Ala Leu Ala Ser Phe Leu Met Gly Phe Met Val Gly Trp Phe Ile Lys
                20                  25                  30

Pro Leu Lys Glu Thr Thr Thr Ser Val Arg Tyr His Gln Ser Ile Arg
            35                  40                  45

Trp Lys Leu Val Ser Glu Met Lys Ala Glu Asn Ile Lys Ser Phe Leu
        50                  55                  60

Arg Ser Phe Thr Lys Leu Pro His Leu Ala Gly Thr Glu Gln Asn Phe
 65                  70                  75                  80

Leu Leu Ala Lys Lys Ile Gln Thr Gln Trp Lys Lys Phe Gly Leu Asp
                 85                  90                  95

Ser Ala Lys Leu Val His Tyr Asp Val Leu Leu Ser Tyr Pro Asn Glu
            100                 105                 110

Thr Asn Ala Asn Tyr Ile Ser Ile Val Asp Glu His Glu Thr Glu Ile
        115                 120                 125

Phe Lys Thr Ser Tyr Leu Glu Pro Pro Asp Gly Tyr Glu Asn Val
    130                 135                 140

Thr Asn Ile Val Pro Pro Tyr Asn Ala Phe Ser Ala Gln Gly Met Pro
145                 150                 155                 160

Glu Gly Asp Leu Val Tyr Val Asn Tyr Ala Arg Thr Glu Asp Phe Phe
                165                 170                 175

Lys Leu Glu Arg Glu Met Gly Ile Asn Cys Thr Gly Lys Ile Val Ile
            180                 185                 190

Ala Arg Tyr Gly Lys Ile Phe Arg Gly Asn Lys Val Lys Asn Ala Met
        195                 200                 205

Leu Ala Gly Ala Ile Gly Ile Ile Leu Tyr Ser Asp Pro Ala Asp Tyr
    210                 215                 220

Phe Ala Pro Glu Val Gln Pro Tyr Pro Lys Gly Trp Asn Leu Pro Gly
225                 230                 235                 240

Thr Ala Ala Gln Arg Gly Asn Val Leu Asn Leu Asn Gly Ala Gly Asp
                245                 250                 255

Pro Leu Thr Pro Gly Tyr Pro Ala Lys Glu Tyr Thr Phe Arg Leu Asp
            260                 265                 270

Val Glu Glu Gly Val Gly Ile Pro Arg Ile Pro Val His Pro Ile Gly
        275                 280                 285
```

-continued

```
Tyr Asn Asp Ala Glu Ile Leu Leu Arg Tyr Leu Gly Ile Ala Pro
    290                 295                 300

Pro Asp Lys Ser Trp Lys Gly Ala Leu Asn Val Ser Tyr Ser Ile Gly
305                 310                 315                 320

Pro Gly Phe Thr Gly Ser Asp Ser Phe Arg Lys Val Arg Met His Val
                325                 330                 335

Tyr Asn Ile Asn Lys Ile Thr Arg Ile Tyr Asn Val Val Gly Thr Ile
                340                 345                 350

Arg Gly Ser Val Glu Pro Asp Arg Tyr Val Ile Leu Gly Gly His Arg
            355                 360                 365

Asp Ser Trp Val Phe Gly Ala Ile Asp Pro Thr Ser Gly Val Ala Val
    370                 375                 380

Leu Gln Glu Ile Ala Arg Ser Phe Gly Lys Leu Met Ser Lys Gly Trp
385                 390                 395                 400

Arg Pro Arg Arg Thr Ile Ile Phe Ala Ser Trp Asp Ala Glu Glu Phe
                405                 410                 415

Gly Leu Leu Gly Ser Thr Glu Trp Ala Glu Glu Asn Val Lys Ile Leu
                420                 425                 430

Gln Glu Arg Ser Ile Ala Tyr Ile Asn Ser Asp Ser Ser Ile Glu Gly
            435                 440                 445

Asn Tyr Thr Leu Arg Val Asp Cys Thr Pro Leu Leu Tyr Gln Leu Val
    450                 455                 460

Tyr Lys Leu Thr Lys Glu Ile Pro Ser Pro Asp Asp Gly Phe Glu Ser
465                 470                 475                 480

Lys Ser Leu Tyr Glu Ser Trp Leu Glu Lys Asp Pro Ser Pro Glu Asn
                485                 490                 495

Lys Asn Leu Pro Arg Ile Asn Lys Leu Gly Ser Gly Ser Asp Phe Glu
                500                 505                 510

Ala Tyr Phe Gln Arg Leu Gly Ile Ala Ser Gly Arg Ala Arg Tyr Thr
    515                 520                 525

Lys Asn Lys Lys Thr Asp Lys Tyr Ser Ser Tyr Pro Val Tyr His Thr
530                 535                 540

Ile Tyr Glu Thr Phe Glu Leu Val Glu Lys Phe Tyr Asp Pro Thr Phe
545                 550                 555                 560

Lys Lys Gln Leu Ser Val Ala Gln Leu Arg Gly Ala Leu Val Tyr Glu
                565                 570                 575

Leu Val Asp Ser Lys Ile Ile Pro Phe Asn Ile Gln Asp Tyr Ala Glu
            580                 585                 590

Ala Leu Lys Asn Tyr Ala Ala Ser Ile Tyr Asn Leu Ser Lys Lys His
    595                 600                 605

Asp Gln Gln Leu Thr Asp His Gly Val Ser Phe Asp Ser Leu Phe Ser
610                 615                 620

Ala Val Lys Asn Phe Ser Glu Ala Ala Ser Asp Phe His Lys Arg Leu
625                 630                 635                 640

Ile Gln Val Asp Leu Asn Asn Pro Ile Ala Val Arg Met Met Asn Asp
                645                 650                 655

Gln Leu Met Leu Leu Glu Arg Ala Phe Ile Asp Pro Leu Gly Leu Pro
                660                 665                 670

Gly Lys Leu Phe Tyr Arg His Ile Ile Phe Ala Pro Ser Ser His Asn
            675                 680                 685

Lys Tyr Ala Gly Glu Ser Phe Pro Gly Ile Tyr Asp Ala Ile Phe Asp
    690                 695                 700

Ile Glu Asn Lys Ala Asn Ser Arg Leu Ala Trp Lys Glu Val Lys Lys
```

```
                705                 710                 715                 720
            His Ile Ser Ile Ala Ala Phe Thr Ile Gln Ala Ala Gly Thr Leu
                            725                 730                 735

Lys Glu Val Leu
                        740

<210> SEQ ID NO 49
<211> LENGTH: 1884
<212> TYPE: DNA
<213> ORGANISM: Homo sapiens
<220> FEATURE:
<221> NAME/KEY: CDS
<222> LOCATION: (149)..(1564)

<400> SEQUENCE: 49
cggcgcggag ggccccagcc cagtcagggg tgtggccgcc gccaccgtaa ggctaggccg        60
cgagcttagt cctgggagcc gcctccgtcg ccgccgtcag agccgcccta tcagattatc       120
ttaacaagaa aaccaactgg aaaaaaaa atg aaa ttc ctt atc ttc gca ttt          172
                                Met Lys Phe Leu Ile Phe Ala Phe
                                  1               5 ttc ggt ggt gtt cac ctt tta tcc ctg tgc tct ggg aaa gct ata tgc         220
Phe Gly Gly Val His Leu Leu Ser Leu Cys Ser Gly Lys Ala Ile Cys
         10                  15                  20 aag aat ggc atc tct aag agg act ttt gaa gaa ata aaa gaa gaa ata         268
Lys Asn Gly Ile Ser Lys Arg Thr Phe Glu Glu Ile Lys Glu Glu Ile
 25                  30                  35                  40 gcc agc tgt gga gat gtt gct aaa gca atc atc aac cta gct gtt tat         316
Ala Ser Cys Gly Asp Val Ala Lys Ala Ile Ile Asn Leu Ala Val Tyr
                 45                  50                  55 ggt aaa gcc cag aac aga tcc tat gag cga ttg gca ctt ctg gtt gat         364
Gly Lys Ala Gln Asn Arg Ser Tyr Glu Arg Leu Ala Leu Leu Val Asp
             60                  65                  70 act gtt gga ccc aga ctg agt ggc tcc aag aac cta gaa aaa gcc atc         412
Thr Val Gly Pro Arg Leu Ser Gly Ser Lys Asn Leu Glu Lys Ala Ile
         75                  80                  85 caa att atg tac caa aac ctg cag caa gat ggg ctg gag aaa gtt cac         460
Gln Ile Met Tyr Gln Asn Leu Gln Gln Asp Gly Leu Glu Lys Val His
         90                  95                 100 ctg gag cca gtg aga ata ccc cac tgg gag agg gga gaa gaa tca gct         508
Leu Glu Pro Val Arg Ile Pro His Trp Glu Arg Gly Glu Glu Ser Ala
105                 110                 115                 120 gtg atg ctg gag cca aga att cat aag ata gcc atc ctg ggt ctt ggc         556
Val Met Leu Glu Pro Arg Ile His Lys Ile Ala Ile Leu Gly Leu Gly
                125                 130                 135 agc agc att ggg act cct cca gaa ggc att aca gca gaa gtt ctg gtg         604
Ser Ser Ile Gly Thr Pro Pro Glu Gly Ile Thr Ala Glu Val Leu Val
            140                 145                 150 gtg acc tct ttc gat gaa ctg cag aga agg gcc tca gaa gca aga ggg         652
Val Thr Ser Phe Asp Glu Leu Gln Arg Arg Ala Ser Glu Ala Arg Gly
        155                 160                 165 aag att gtt gtt tat aac caa cct tac atc aac tac tca agg acg gtg         700
Lys Ile Val Val Tyr Asn Gln Pro Tyr Ile Asn Tyr Ser Arg Thr Val
    170                 175                 180 caa tac cga acg cag ggg gcg gtg gaa gct gcc aag gtt ggg gct ttg         748
Gln Tyr Arg Thr Gln Gly Ala Val Glu Ala Ala Lys Val Gly Ala Leu
185                 190                 195                 200 gca tct ctc att cga tcc gtg gcc tcc ttc tcc atc tac agt cct cac         796
Ala Ser Leu Ile Arg Ser Val Ala Ser Phe Ser Ile Tyr Ser Pro His
                205                 210                 215
```

```
aca ggt att cag gaa tac cag gat ggc gtg ccc aag att cca aca gcc    844
Thr Gly Ile Gln Glu Tyr Gln Asp Gly Val Pro Lys Ile Pro Thr Ala
        220                 225                 230 tgt att acg gtg gaa gat gca gaa atg atg tca aga atg gct tct cat    892
Cys Ile Thr Val Glu Asp Ala Glu Met Met Ser Arg Met Ala Ser His
    235                 240                 245 ggg atc aaa att gtc att cag cta aag atg ggg gca aag acc tac cca    940
Gly Ile Lys Ile Val Ile Gln Leu Lys Met Gly Ala Lys Thr Tyr Pro
250                 255                 260 gat act gat tcc ttc aac act gta gca gag atc act ggg agc aaa tat    988
Asp Thr Asp Ser Phe Asn Thr Val Ala Glu Ile Thr Gly Ser Lys Tyr
265                 270                 275                 280 cca gaa cag gtt gta ctg gtc agt gga cat ctg gac agc tgg gat gtt   1036
Pro Glu Gln Val Val Leu Val Ser Gly His Leu Asp Ser Trp Asp Val
                285                 290                 295 ggg cag ggt gcc atg gat gat ggc ggt gga gcc ttt ata tca tgg gaa   1084
Gly Gln Gly Ala Met Asp Asp Gly Gly Gly Ala Phe Ile Ser Trp Glu
            300                 305                 310 gca ctc tca ctt att aaa gat ctt ggg ctg cgt cca aag agg act ctg   1132
Ala Leu Ser Leu Ile Lys Asp Leu Gly Leu Arg Pro Lys Arg Thr Leu
        315                 320                 325 cgg ctg gtg ctc tgg act gca gaa gaa caa ggt gga gtt ggt gcc ttc   1180
Arg Leu Val Leu Trp Thr Ala Glu Glu Gln Gly Gly Val Gly Ala Phe
    330                 335                 340 cag tat tat cag tta cac aag gta aat att tcc aac tac agt ctg gtg   1228
Gln Tyr Tyr Gln Leu His Lys Val Asn Ile Ser Asn Tyr Ser Leu Val
345                 350                 355                 360 atg gag tct gac gca gga acc ttc tta ccc act ggg ctg caa ttc act   1276
Met Glu Ser Asp Ala Gly Thr Phe Leu Pro Thr Gly Leu Gln Phe Thr
                365                 370                 375 ggc agt gaa aag gcc agg gcc atc atg gag gag gtt atg agc ctg ctg   1324
Gly Ser Glu Lys Ala Arg Ala Ile Met Glu Glu Val Met Ser Leu Leu
            380                 385                 390 cag ccc ctc aat atc act cag gtc ctg agc cat gga gaa ggg aca gac   1372
Gln Pro Leu Asn Ile Thr Gln Val Leu Ser His Gly Glu Gly Thr Asp
        395                 400                 405 atc aac ttt tgg atc caa gct gga gtg cct gga gcc agt cta ctt gat   1420
Ile Asn Phe Trp Ile Gln Ala Gly Val Pro Gly Ala Ser Leu Leu Asp
    410                 415                 420 gac tta tac aag tat ttc ttc ttc cat cac tcc cac gga gac acc atg   1468
Asp Leu Tyr Lys Tyr Phe Phe Phe His His Ser His Gly Asp Thr Met
425                 430                 435                 440 act gtc atg gat cca aag cag atg aat gtt gct gct gct gtt tgg gct   1516
Thr Val Met Asp Pro Lys Gln Met Asn Val Ala Ala Ala Val Trp Ala
                445                 450                 455 gtt gtt tct tat gtt gtt gca gac atg gaa gaa atg ctg cct agg tcc   1564
Val Val Ser Tyr Val Val Ala Asp Met Glu Glu Met Leu Pro Arg Ser
            460                 465                 470 tagaaacagt aagaaagaaa cgttttcatg cttctggcca ggaatcctgg gtctgcaact   1624
ttggaaaact cctcttcaca taacaatttc atccaattca tcttcaaagc acaactctat   1684
ttcatgcttt ctgttattat ctttcttgat actttccaaa ttctctgatt ctagaaaaag   1744
gaatcattct cccctccctc ccaccacata gaatcaacat atggtaggga ttacagtggg   1804
ggcatttctt tatatcacct cttaaaaaca ttgtttccac tttaaaagta aacacttaat   1864 aaattttttgg aagatctctg                                              1884

<210> SEQ ID NO 50
<211> LENGTH: 472
```

```
<212> TYPE: PRT
<213> ORGANISM: Homo sapiens

<400> SEQUENCE: 50

Met Lys Phe Leu Ile Phe Ala Phe Phe Gly Gly Val His Leu Leu Ser
  1               5                  10                  15

Leu Cys Ser Gly Lys Ala Ile Cys Lys Asn Gly Ile Ser Lys Arg Thr
             20                  25                  30

Phe Glu Glu Ile Lys Glu Ile Ala Ser Cys Gly Asp Val Ala Lys
         35                  40                  45

Ala Ile Ile Asn Leu Ala Val Tyr Gly Lys Ala Gln Asn Arg Ser Tyr
 50                  55                  60

Glu Arg Leu Ala Leu Val Asp Thr Val Gly Pro Arg Leu Ser Gly
 65                  70                  75                  80

Ser Lys Asn Leu Glu Lys Ala Ile Gln Ile Met Tyr Gln Asn Leu Gln
             85                  90                  95

Gln Asp Gly Leu Glu Lys Val His Leu Glu Pro Val Arg Ile Pro His
            100                 105                 110

Trp Glu Arg Gly Glu Glu Ser Ala Val Met Leu Glu Pro Arg Ile His
            115                 120                 125

Lys Ile Ala Ile Leu Gly Leu Gly Ser Ser Ile Gly Thr Pro Pro Glu
130                 135                 140

Gly Ile Thr Ala Glu Val Leu Val Val Thr Ser Phe Asp Glu Leu Gln
145                 150                 155                 160

Arg Arg Ala Ser Glu Ala Arg Gly Lys Ile Val Val Tyr Asn Gln Pro
                165                 170                 175

Tyr Ile Asn Tyr Ser Arg Thr Val Gln Tyr Arg Thr Gln Gly Ala Val
            180                 185                 190

Glu Ala Ala Lys Val Gly Ala Leu Ala Ser Leu Ile Arg Ser Val Ala
            195                 200                 205

Ser Phe Ser Ile Tyr Ser Pro His Thr Gly Ile Gln Glu Tyr Gln Asp
            210                 215                 220

Gly Val Pro Lys Ile Pro Thr Ala Cys Ile Thr Val Glu Asp Ala Glu
225                 230                 235                 240

Met Met Ser Arg Met Ala Ser His Gly Ile Lys Ile Val Ile Gln Leu
                245                 250                 255

Lys Met Gly Ala Lys Thr Tyr Pro Asp Thr Asp Ser Phe Asn Thr Val
            260                 265                 270

Ala Glu Ile Thr Gly Ser Lys Tyr Pro Glu Gln Val Val Leu Val Ser
            275                 280                 285

Gly His Leu Asp Ser Trp Asp Val Gly Gln Gly Ala Met Asp Asp Gly
            290                 295                 300

Gly Gly Ala Phe Ile Ser Trp Glu Ala Leu Ser Leu Ile Lys Asp Leu
305                 310                 315                 320

Gly Leu Arg Pro Lys Arg Thr Leu Arg Leu Val Leu Trp Thr Ala Glu
                325                 330                 335

Glu Gln Gly Gly Val Gly Ala Phe Gln Tyr Tyr Gln Leu His Lys Val
            340                 345                 350

Asn Ile Ser Asn Tyr Ser Leu Val Met Glu Ser Asp Ala Gly Thr Phe
            355                 360                 365

Leu Pro Thr Gly Leu Gln Phe Thr Gly Ser Glu Lys Ala Arg Ala Ile
            370                 375                 380

Met Glu Glu Val Met Ser Leu Leu Gln Pro Leu Asn Ile Thr Gln Val
385                 390                 395                 400
```

-continued

```
Leu Ser His Gly Glu Gly Thr Asp Ile Asn Phe Trp Ile Gln Ala Gly
                405                 410                 415
Val Pro Gly Ala Ser Leu Leu Asp Asp Leu Tyr Lys Tyr Phe Phe Phe
            420                 425                 430
His His Ser His Gly Asp Thr Met Thr Val Met Asp Pro Lys Gln Met
        435                 440                 445
Asn Val Ala Ala Val Trp Ala Val Ser Tyr Val Val Ala Asp
    450                 455                 460
Met Glu Glu Met Leu Pro Arg Ser
465                 470

<210> SEQ ID NO 51
<211> LENGTH: 750
<212> TYPE: PRT
<213> ORGANISM: Homo sapiens

<400> SEQUENCE: 51

Met Trp Asn Leu Leu His Glu Thr Asp Ser Ala Val Ala Thr Ala Arg
  1               5                  10                  15
Arg Pro Arg Trp Leu Cys Ala Gly Ala Leu Val Leu Ala Gly Gly Phe
             20                  25                  30
Phe Leu Leu Gly Phe Leu Phe Gly Trp Phe Ile Lys Ser Ser Asn Glu
         35                  40                  45
Ala Thr Asn Ile Thr Pro Lys His Asn Met Lys Ala Phe Leu Asp Glu
     50                  55                  60
Leu Lys Ala Glu Asn Ile Lys Lys Phe Leu His Asn Phe Thr Gln Ile
 65                  70                  75                  80
Pro His Leu Ala Gly Thr Glu Gln Asn Phe Gln Leu Ala Lys Gln Ile
                 85                  90                  95
Gln Ser Gln Trp Lys Glu Phe Gly Leu Asp Ser Val Glu Leu Ala His
            100                 105                 110
Tyr Asp Val Leu Leu Ser Tyr Pro Asn Lys Thr His Pro Asn Tyr Ile
        115                 120                 125
Ser Ile Ile Asn Glu Asp Gly Asn Glu Ile Phe Asn Thr Ser Leu Phe
    130                 135                 140
Glu Pro Pro Pro Pro Gly Tyr Glu Asn Val Ser Asp Ile Val Pro Pro
145                 150                 155                 160
Phe Ser Ala Phe Ser Pro Gln Gly Met Pro Glu Gly Asp Leu Val Tyr
                165                 170                 175
Val Asn Tyr Ala Arg Thr Glu Asp Phe Phe Lys Leu Glu Arg Asp Met
            180                 185                 190
Lys Ile Asn Cys Ser Gly Lys Ile Val Ile Ala Arg Tyr Gly Lys Val
        195                 200                 205
Phe Arg Gly Asn Lys Val Lys Asn Ala Gln Leu Ala Gly Ala Lys Gly
    210                 215                 220
Val Ile Leu Tyr Ser Asp Pro Ala Asp Tyr Phe Ala Pro Gly Val Lys
225                 230                 235                 240
Ser Tyr Pro Asp Gly Trp Asn Leu Pro Gly Gly Gly Val Gln Arg Gly
                245                 250                 255
Asn Ile Leu Asn Leu Asn Gly Ala Gly Asp Pro Leu Thr Pro Gly Tyr
            260                 265                 270
Pro Ala Asn Glu Tyr Ala Tyr Arg Arg Gly Ile Ala Glu Ala Val Gly
        275                 280                 285
Leu Pro Ser Ile Pro Val His Pro Ile Gly Tyr Tyr Asp Ala Gln Lys
```

-continued

```
                290                 295                 300
Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
                340                 345                 350

Thr Arg Ile Tyr Asn Val Ile Gly Thr Leu Arg Gly Ala Val Glu Pro
                355                 360                 365

Asp Arg Tyr Val Ile Leu Gly Gly His Arg Asp Ser Trp Val Phe Gly
370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
                420                 425                 430

Glu Trp Ala Glu Glu Asn Ser Arg Leu Leu Gln Glu Arg Gly Val Ala
                435                 440                 445

Tyr Ile Asn Ala Asp Ser Ser Ile Glu Gly Asn Tyr Thr Leu Arg Val
450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
                500                 505                 510

Ser Lys Leu Gly Ser Gly Asn Asp Phe Glu Val Phe Phe Gln Arg Leu
                515                 520                 525

Gly Ile Ala Ser Gly Arg Ala Arg Tyr Thr Lys Asn Trp Glu Thr Asn
                530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
                580                 585                 590

Leu Pro Phe Asp Cys Arg Asp Tyr Ala Val Val Leu Arg Lys Tyr Ala
                595                 600                 605

Asp Lys Ile Tyr Ser Ile Ser Met Lys His Pro Gln Glu Met Lys Thr
                610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
                660                 665                 670

Arg Ala Phe Ile Asp Pro Leu Gly Leu Pro Asp Arg Pro Phe Tyr Arg
                675                 680                 685

His Val Ile Tyr Ala Pro Ser Ser His Asn Lys Tyr Ala Gly Glu Ser
690                 695                 700

Phe Pro Gly Ile Tyr Asp Ala Leu Phe Asp Ile Glu Ser Lys Val Asp
705                 710                 715                 720
```

```
Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
            740                 745                 750

<210> SEQ ID NO 52
<211> LENGTH: 265
<212> TYPE: PRT
<213> ORGANISM: Saccharomyces cerevisiae

<400> SEQUENCE: 52

Thr Lys His Thr Val Ala Thr Val Gly Val Pro Tyr Lys Val Gly Lys
  1               5                  10                  15

Lys Leu Ile Ala Asn Ile Ala Leu Asn Ile Asp Tyr Ser Leu Tyr Phe
                 20                  25                  30

Ala Met Asp Ser Tyr Val Glu Phe Ile Lys Thr Gln Asn Ile Ile Ala
             35                  40                  45

Asp Thr Lys His Gly Asp Pro Asp Asn Ile Val Ala Leu Gly Ala His
         50                  55                  60

Ser Asp Ser Val Glu Gly Pro Gly Ile Asn Asp Asp Gly Ser Gly
 65                  70                  75                  80

Thr Ile Ser Leu Leu Asn Val Ala Lys Gln Leu Thr His Phe Lys Ile
                 85                  90                  95

Asn Asn Lys Val Arg Phe Ala Trp Trp Ala Ala Glu Glu Gly Leu
                100                 105                 110

Leu Gly Ser Asn Phe Tyr Ala Tyr Asn Leu Thr Lys Glu Glu Asn Ser
            115                 120                 125

Lys Ile Arg Val Phe Met Asp Tyr Asp Met Met Ala Ser Pro Asn Tyr
        130                 135                 140

Glu Tyr Glu Ile Tyr Asp Ala Asn Asn Lys Glu Asn Pro Lys Gly Ser
145                 150                 155                 160

Glu Glu Leu Lys Asn Leu Tyr Val Asp Tyr Tyr Lys Ala His His Leu
                165                 170                 175

Asn Tyr Thr Leu Val Pro Phe Asp Gly Arg Ser Asp Tyr Val Gly Phe
            180                 185                 190

Ile Asn Asn Gly Ile Pro Ala Gly Gly Ile Ala Thr Gly Ala Glu Lys
        195                 200                 205

Asn Asn Val Asn Asn Gly Lys Val Leu Asp Arg Cys Tyr His Gln Leu
    210                 215                 220

Cys Asp Asp Val Ser Asn Leu Ser Trp Asp Ala Phe Ile Thr Asn Thr
225                 230                 235                 240

Lys Leu Ile Ala His Ser Val Thr Tyr Ala Asp Ser Phe Glu Gly
                245                 250                 255

Phe Pro Lys Arg Glu Thr Gln Lys His
            260                 265

<210> SEQ ID NO 53
<211> LENGTH: 268
<212> TYPE: PRT
<213> ORGANISM: Vibrio cholerae

<400> SEQUENCE: 53

Gln Ile Thr Asn Thr Ile Arg Ala Leu Ser Ser Phe Asn Asn Arg Phe
  1               5                  10                  15

Tyr Thr Thr Ala Ser Gly Ala Gln Ala Ser Asp Trp Leu Ala Asn Glu
                 20                  25                  30
```

-continued

```
Trp Arg Ser Leu Ile Ser Ser Leu Pro Gly Ser Arg Ile Glu Gln Ile
         35                  40                  45
Lys His Ser Gly Tyr Asn Gln Lys Ser Val Val Leu Thr Ile Gln Gly
     50                  55                  60
Ser Glu Lys Pro Asp Glu Trp Val Ile Val Gly Gly His Leu Asp Ser
 65                  70                  75                  80
Thr Leu Gly Ser His Thr Asn Glu Gln Ser Ile Ala Pro Gly Ala Asp
                 85                  90                  95
Asp Asp Ala Ser Gly Ile Ala Ser Leu Ser Glu Ile Ile Arg Val Leu
                100                 105                 110
Arg Asp Asn Asn Phe Arg Pro Lys Arg Ser Ala Ala Leu Met Ala Tyr
            115                 120                 125
Ala Ala Glu Glu Val Gly Leu Arg Gly Ser Gln Asp Pro Ala Asn Gln
        130                 135                 140
Tyr Lys Ala Gln Gly Lys Lys Val Val Ser Val Leu Gln Leu Asp Met
145                 150                 155                 160
Thr Asn Tyr Arg Gly Ser Ala Glu Asp Ile Val Phe Ile Thr Asp Tyr
                165                 170                 175
Thr Asp Ser Asn Leu Thr Gln Phe Leu Thr Thr Leu Ile Asp Glu Tyr
                180                 185                 190
Leu Pro Glu Leu Thr Tyr Gly Tyr Asp Arg Cys Gly Tyr Ala Cys Ser
            195                 200                 205
Asp His Ala Ser Trp His Lys Ala Gly Phe Ser Ala Ala Met Pro Phe
        210                 215                 220
Glu Ser Lys Phe Lys Asp Tyr Asn Pro Lys Ile His Thr Ser Gln Asp
225                 230                 235                 240
Thr Leu Ala Asn Ser Asp Pro Thr Gly Asn His Ala Val Thr Phe Thr
                245                 250                 255
Lys Leu Gly Leu Ala Tyr Val Ile Glu Met Ala Asn
            260                 265

<210> SEQ ID NO 54
<211> LENGTH: 268
<212> TYPE: PRT
<213> ORGANISM: Aeromonas proteolytica

<400> SEQUENCE: 54

Gln Ile Thr Gly Thr Ile Ser Ser Leu Glu Ser Phe Thr Asn Arg Phe
  1               5                  10                  15
Tyr Thr Thr Thr Ser Gly Ala Gln Ala Ser Asp Trp Ile Ala Ser Glu
                 20                  25                  30
Trp Gln Ala Leu Ser Ala Ser Leu Pro Asn Ala Ser Val Lys Gln Val
         35                  40                  45
Ser His Ser Gly Tyr Asn Gln Lys Ser Val Val Met Thr Ile Thr Gly
     50                  55                  60
Ser Glu Ala Pro Asp Glu Trp Ile Val Ile Gly Gly His Leu Asp Ser
 65                  70                  75                  80
Thr Ile Gly Ser His Thr Asn Glu Gln Ser Val Ala Pro Gly Ala Asp
                 85                  90                  95
Asp Asp Ala Ser Gly Ile Ala Val Thr Glu Val Ile Arg Val Leu
                100                 105                 110
Ser Glu Asn Asn Phe Gln Pro Lys Arg Ser Ile Ala Phe Met Ala Tyr
            115                 120                 125
Ala Ala Glu Glu Val Gly Leu Arg Gly Ser Gln Asp Leu Ala Asn Gln
```

```
            130                 135                 140
Tyr Lys Ser Glu Gly Lys Asn Val Val Ser Ala Leu Gln Leu Asp Met
145                 150                 155                 160

Thr Asn Tyr Lys Gly Ser Ala Gln Asp Val Val Phe Ile Thr Asp Tyr
                165                 170                 175

Thr Asp Ser Asn Phe Thr Gln Tyr Leu Thr Gln Leu Met Asp Glu Tyr
            180                 185                 190

Leu Pro Ser Leu Thr Tyr Gly Phe Asp Thr Cys Gly Tyr Ala Cys Ser
            195                 200                 205

Asp His Ala Ser Trp His Asn Ala Gly Tyr Pro Ala Ala Met Pro Phe
210                 215                 220

Glu Ser Lys Phe Asn Asp Tyr Asn Pro Arg Ile His Thr Thr Gln Asp
225                 230                 235                 240

Thr Leu Ala Asn Ser Asp Pro Thr Gly Ser His Ala Lys Lys Phe Thr
                245                 250                 255

Gln Leu Gly Leu Ala Tyr Ala Ile Glu Met Gly Ser
            260                 265

<210> SEQ ID NO 55
<211> LENGTH: 263
<212> TYPE: PRT
<213> ORGANISM: Streptomyces griseus

<400> SEQUENCE: 55

Asn Asn Gly Gly Asn Arg Ala His Gly Arg Pro Gly Tyr Lys Ala Ser
1               5                   10                  15

Val Asp Tyr Val Lys Ala Lys Leu Asp Ala Ala Gly Tyr Thr Thr Thr
                20                  25                  30

Leu Gln Gln Phe Thr Ser Gly Gly Ala Thr Gly Tyr Asn Leu Ile Ala
            35                  40                  45

Asn Trp Pro Gly Gly Asp Pro Asn Lys Val Leu Met Ala Gly Ala His
        50                  55                  60

Leu Asp Ser Val Ser Ser Gly Ala Gly Ile Asn Asp Asn Gly Ser Gly
65                  70                  75                  80

Ser Ala Ala Val Leu Glu Thr Ala Leu Ala Val Ser Arg Ala Gly Tyr
                85                  90                  95

Gln Pro Asp Lys His Leu Arg Phe Ala Trp Trp Gly Ala Glu Glu Leu
            100                 105                 110

Gly Leu Ile Gly Ser Lys Phe Tyr Val Asn Asn Leu Pro Ser Ala Asp
            115                 120                 125

Arg Ser Lys Leu Ala Gly Tyr Leu Asn Phe Asp Met Ile Gly Ser Pro
130                 135                 140

Asn Pro Gly Tyr Phe Val Tyr Asp Asp Asp Pro Val Ile Glu Lys Thr
145                 150                 155                 160

Phe Lys Asn Tyr Phe Ala Gly Leu Asn Val Pro Thr Glu Ile Glu Thr
                165                 170                 175

Glu Gly Asp Gly Arg Ser Asp His Ala Pro Phe Lys Asn Val Gly Val
            180                 185                 190

Pro Val Gly Gly Leu Phe Thr Gly Ala Gly Tyr Thr Lys Ser Ala Ala
            195                 200                 205

Gln Ala Gln Lys Trp Gly Gly Thr Ala Gly Gln Ala Phe Asp Arg Cys
        210                 215                 220

Tyr His Ser Ser Cys Asp Ser Leu Ser Asn Ile Asn Asp Thr Ala Leu
225                 230                 235                 240
```

```
Asp Arg Asn Ser Asp Ala Ala His Ala Ile Trp Thr Leu Ser Ser
            245                 250                 255

Gly Thr Gly Glu Pro Pro Thr
            260
```

<210> SEQ ID NO 56
<211> LENGTH: 282
<212> TYPE: PRT
<213> ORGANISM: Homo sapiens

<400> SEQUENCE: 56

```
Asp Ala Gln Lys Leu Leu Glu Lys Met Gly Gly Ser Ala Pro Pro Asp
 1               5                  10                  15

Ser Ser Trp Arg Gly Ser Leu Lys Val Pro Tyr Asn Val Gly Pro Gly
                20                  25                  30

Phe Thr Gly Asn Phe Ser Thr Gln Lys Val Lys Met His Ile His Ser
            35                  40                  45

Thr Asn Glu Val Thr Arg Ile Tyr Asn Val Ile Gly Thr Leu Arg Gly
    50                  55                  60

Ala Val Glu Pro Asp Arg Tyr Val Ile Leu Gly Gly His Arg Asp Ser
65                  70                  75                  80

Trp Val Phe Gly Gly Ile Asp Pro Gln Ser Gly Ala Ala Val Val His
                85                  90                  95

Glu Ile Val Arg Ser Phe Gly Thr Leu Lys Lys Glu Gly Trp Arg Pro
            100                 105                 110

Arg Arg Thr Ile Leu Phe Ala Ser Trp Asp Ala Glu Glu Phe Gly Leu
        115                 120                 125

Leu Gly Ser Thr Glu Trp Ala Glu Glu Asn Ser Arg Leu Leu Gln Glu
130                 135                 140

Arg Gly Val Ala Tyr Ile Asn Ala Asp Ser Ser Ile Glu Gly Asn Tyr
145                 150                 155                 160

Thr Leu Arg Val Asp Cys Thr Pro Leu Met Tyr Ser Leu Val His Asn
                165                 170                 175

Leu Thr Lys Glu Leu Lys Ser Pro Asp Glu Gly Phe Glu Gly Lys Ser
            180                 185                 190

Leu Tyr Glu Ser Trp Thr Lys Lys Ser Pro Ser Pro Glu Phe Ser Gly
        195                 200                 205

Met Pro Arg Ile Ser Lys Leu Gly Ser Gly Asn Asp Phe Glu Val Phe
    210                 215                 220

Phe Gln Arg Leu Gly Ile Ala Ser Gly Arg Ala Arg Tyr Thr Lys Asn
225                 230                 235                 240

Trp Glu Thr Asn Lys Phe Ser Gly Tyr Pro Leu Tyr His Ser Val Tyr
                245                 250                 255

Glu Thr Tyr Glu Leu Val Glu Lys Phe Tyr Asp Pro Met Phe Lys Tyr
            260                 265                 270

His Leu Thr Val Ala Gln Val Arg Gly Gly
        275                 280
```

<210> SEQ ID NO 57
<211> LENGTH: 282
<212> TYPE: PRT
<213> ORGANISM: Homo sapiens

<400> SEQUENCE: 57

```
Asp Ala Glu Ile Leu Leu Arg Tyr Leu Gly Gly Ile Ala Pro Pro Asp
 1               5                  10                  15
```

-continued

```
Lys Ser Trp Lys Gly Ala Leu Asn Val Ser Tyr Ser Ile Gly Pro Gly
            20                  25                  30

Phe Thr Gly Ser Asp Ser Phe Arg Lys Val Arg Met His Val Tyr Asn
         35                  40                  45

Ile Asn Lys Ile Thr Arg Ile Tyr Asn Val Val Gly Thr Ile Arg Gly
 50                  55                  60

Ser Val Glu Pro Asp Arg Tyr Val Ile Leu Gly Gly His Arg Asp Ser
 65                  70                  75                  80

Trp Val Phe Gly Ala Ile Asp Pro Thr Ser Gly Val Ala Val Leu Gln
                 85                  90                  95

Glu Ile Ala Arg Ser Phe Gly Lys Leu Met Ser Lys Gly Trp Arg Pro
            100                 105                 110

Arg Arg Thr Ile Ile Phe Ala Ser Trp Asp Ala Glu Glu Phe Gly Leu
            115                 120                 125

Leu Gly Ser Thr Glu Trp Ala Glu Glu Asn Val Lys Ile Leu Gln Glu
130                 135                 140

Arg Ser Ile Ala Tyr Ile Asn Ser Asp Ser Ser Ile Glu Gly Asn Tyr
145                 150                 155                 160

Thr Leu Arg Val Asp Cys Thr Pro Leu Leu Tyr Gln Leu Val Tyr Lys
                165                 170                 175

Leu Thr Lys Glu Ile Pro Ser Pro Asp Asp Gly Phe Glu Ser Lys Ser
            180                 185                 190

Leu Tyr Glu Ser Trp Leu Glu Lys Asp Pro Ser Pro Glu Asn Lys Asn
            195                 200                 205

Leu Pro Arg Ile Asn Lys Leu Gly Ser Gly Ser Asp Phe Glu Ala Tyr
        210                 215                 220

Phe Gln Arg Leu Gly Ile Ala Ser Gly Arg Ala Arg Tyr Thr Lys Asn
225                 230                 235                 240

Lys Lys Thr Asp Lys Tyr Ser Ser Tyr Pro Val Tyr His Thr Ile Tyr
                245                 250                 255

Glu Thr Phe Glu Leu Val Glu Lys Phe Tyr Asp Pro Thr Phe Lys Lys
            260                 265                 270

Gln Leu Ser Val Ala Gln Leu Arg Gly Ala
            275                 280
```

<210> SEQ ID NO 58
<211> LENGTH: 283
<212> TYPE: PRT
<213> ORGANISM: Homo sapiens

<400> SEQUENCE: 58

```
Arg Asp Leu Leu Cys Asn Leu Asn Gly Thr Leu Ala Pro Ala Thr Trp
 1               5                  10                  15

Gln Gly Ala Leu Gly Cys His Tyr Arg Leu Gly Pro Gly Phe Arg Pro
            20                  25                  30

Asp Gly Asp Phe Pro Ala Asp Ser Gln Val Asn Val Ser Val Tyr Asn
         35                  40                  45

Arg Leu Glu Leu Arg Asn Ser Ser Asn Val Leu Gly Ile Ile Arg Gly
 50                  55                  60

Ala Val Glu Pro Asp Arg Tyr Val Leu Tyr Gly Asn His Arg Asp Ser
 65                  70                  75                  80

Trp Val His Gly Ala Val Asp Pro Ser Ser Gly Thr Ala Val Leu Leu
                 85                  90                  95

Glu Leu Ser Arg Val Leu Gly Thr Leu Leu Lys Lys Gly Thr Trp Arg
            100                 105                 110
```

```
Pro Arg Arg Ser Ile Val Phe Ala Ser Trp Gly Ala Glu Glu Phe Gly
        115                 120                 125

Leu Ile Gly Ser Thr Glu Phe Thr Glu Glu Phe Phe Asn Lys Leu Gln
    130                 135                 140

Glu Arg Thr Val Ala Tyr Ile Asn Val Asp Ile Ser Val Phe Ala Asn
145                 150                 155                 160

Ala Thr Leu Arg Val Gln Gly Thr Pro Pro Val Gln Ser Val Val Phe
                165                 170                 175

Ser Ala Thr Lys Glu Ile Arg Ser Pro Gly Pro Gly Asp Leu Ser Ile
                180                 185                 190

Tyr Asp Asn Trp Ile Arg Tyr Phe Asn Arg Ser Ser Pro Val Tyr Gly
                195                 200                 205

Leu Val Pro Ser Leu Gly Ser Leu Gly Ala Gly Ser Asp Tyr Ala Pro
    210                 215                 220

Phe Val His Phe Leu Gly Ile Ser Ser Met Asp Ile Ala Tyr Thr Tyr
225                 230                 235                 240

Asp Arg Ser Lys Thr Ser Ala Arg Ile Tyr Pro Thr Tyr His Thr Ala
                245                 250                 255

Phe Asp Thr Phe Asp Tyr Val Asp Lys Phe Leu Asp Pro Gly Phe Ser
                260                 265                 270

Ser His Gln Ala Val Ala Arg Thr Ala Gly Ser
                275                 280
```

<210> SEQ ID NO 59
<211> LENGTH: 259
<212> TYPE: PRT
<213> ORGANISM: Homo sapiens

<400> SEQUENCE: 59

```
Ser Pro His Thr Gly Ile Gln Glu Tyr Gln Asp Gly Val Pro Lys Ile
1               5                   10                  15

Pro Thr Ala Cys Ile Thr Val Glu Asp Ala Glu Met Met Ser Arg Met
                20                  25                  30

Ala Ser His Gly Ile Lys Ile Val Ile Gln Leu Lys Met Gly Ala Lys
            35                  40                  45

Thr Tyr Pro Asp Thr Asp Ser Phe Asn Thr Val Ala Glu Ile Thr Gly
        50                  55                  60

Ser Lys Tyr Pro Glu Gln Val Val Leu Val Ser Gly His Leu Asp Ser
65                  70                  75                  80

Trp Asp Val Gly Gln Gly Ala Met Asp Asp Gly Gly Gly Ala Phe Ile
                85                  90                  95

Ser Trp Glu Ala Leu Ser Leu Ile Lys Asp Leu Gly Leu Arg Pro Lys
            100                 105                 110

Arg Thr Leu Arg Leu Val Leu Trp Thr Ala Glu Glu Gln Gly Gly Val
        115                 120                 125

Gly Ala Phe Gln Tyr Tyr Gln Leu His Lys Val Asn Ile Ser Asn Tyr
    130                 135                 140

Ser Leu Val Met Glu Ser Asp Ala Gly Thr Phe Leu Pro Thr Gly Leu
145                 150                 155                 160

Gln Phe Thr Gly Ser Glu Lys Ala Arg Ala Ile Met Glu Glu Val Met
                165                 170                 175

Ser Leu Leu Gln Pro Leu Asn Ile Thr Gln Val Leu Ser His Gly Glu
                180                 185                 190

Gly Thr Asp Ile Asn Phe Trp Ile Gln Ala Gly Val Pro Gly Ala Ser
```

|  | 195 |  |  |  | 200 |  |  |  | 205 |  |  |
|---|---|---|---|---|---|---|---|---|---|---|---|
| Leu | Leu | Asp | Asp | Leu | Tyr | Lys | Tyr | Phe | Phe | His | Gly |
|  | 210 |  |  |  | 215 |  |  |  | 220 |  |  |

Asp Thr Met Thr Val Met Asp Pro Lys Gln Met Asn Val Ala Ala Ala
225                 230                 235                 240

Val Trp Ala Val Val Ser Tyr Val Val Ala Asp Met Glu Glu Met Leu
                245                 250                 255

Pro Arg Ser

<210> SEQ ID NO 60
<211> LENGTH: 2197
<212> TYPE: DNA
<213> ORGANISM: Homo sapiens
<220> FEATURE:
<221> NAME/KEY: modified_base
<222> LOCATION: (315)
<223> OTHER INFORMATION: a, c, g, t, unknown or other

<400> SEQUENCE: 60

```
gccaagagtc cgcaggatgc agtggacgaa ggtgttgggg ctggggctgg gggctgctgc        60
cctcttgggg ctgggatca tcctcggcca ctttgccatc cccaaaaaag ccaactcact       120
ggccccccag gacctggacc tggagatcct ggagaccgtc atggggcagc tggatgccca       180
caggatccgg gagaacctca gagaactctc caggagccca cacctggcct ccagccctcg       240
ggatgaggac ctggtgcagc tgctgctgca gcgctggaag gacccagagt caggcctgga       300
ctcggccgag gcctncacgt acgaagtgct gctgtccttc cctagccagg agcagcccaa       360
cgtcgtggac atcgtgggcc ccactggggg catcatccac tcctgccacc ggactgagga       420
gaacgtgacc ggggagcaag gggggccaga tgtggtacaa ccctatgctg cctatgctcc       480
ttctggaacc ccacaggctg tgaacgctgc caagcacggg gtagctgggg tgctggtgta       540
cacagaccct gccgacatca acgatgggct gagctcaccc gacgaaacct ttcccaactc       600
ctggtacctg cccccctcag gagtggagcg aggctcctac tacgagtatt tggggacccc       660
tctgactccc taccttccag ccgtcccctc ttccttccgc gtggaccttg ccaatgtctc       720
cggatttccc ccaattccta cacagcccat ggcttccag gatgcaagag acctgctctg       780
taacctcaac ggaactttgg ccccagccac ctggcaggga gcactgggct gccactacag       840
gttgggtccc ggcttccggc ctgacggaga cttcccagca gacagccagg tgaatgtgag       900
cgtctacaac cgcctggagc tgaggaactc ttccaacgtc ctgggcatca tccgtgggc        960
tgtggagcct gatcgctacg tgctgtatgg gaaccaccga gacagctggg tgcacggggc      1020
tgtggacccc agcagtggca ccgccgtcct cctggagctc tcccgtgtcc tggggacccct     1080
gctgaagaag ggcacctggc gtcctcgcag atcaatcgtg tttgcgagct gggggctga      1140
ggagtttggg ctcattggct ccacggaatt cacagaagag ttcttcaaca agctgcagga     1200
gcgcacggtg gcctacatca acgtggacat ctcggtgttt gccaacgcta cccttagggt     1260
gcaggggacg cccccctgtcc agagcgtcgt cttctctgca accaaagaga tccgctcacc    1320
aggccctggc gacctgagca tctacgacaa ctggatccgg tacttcaacc gcagcagccc     1380
ggtgtacggc ctggtcccca gcttgggttc tctgggtgct ggcagcgact atgcaccctt     1440
cgttcacttc ctgggcatct cctccatgga cattgcctat acctatgacc ggagcaagac     1500
ttcagccagg atctaccccca cctaccacac agcctttgac acctttgact atgtggacaa    1560
gttttttggac ccgggcttca gcagccatca ggctgtggcc cggacagcgg ggagtgtgat    1620
```

-continued

```
tctccggctc agtgacagct tcttcctgcc cctcaaagtc agtgactaca gtgagacact    1680
ccgcagcttc ctgcaggcag cccagcaaga tcttggggcc ctgctggagc agcacagcat    1740
cagcctgggg cctctggtga ctgcagtgga aagtttgag gcagaagctg cagccttggg     1800
ccaacgcata tcaacactgc agaagggcag ccctgacccc ctgcaggtcc ggatgctcaa    1860
tgaccagttg atgctcttgg aacggaccttt tctgaaccct agagccttcc cagaggaacg   1920
ctactacagc catgtgctct gggcaccttc gcacgggctc cgtagtcaca ttccggggct    1980
atccaatgcc tgctccaggg ccagggacac agcttctgga tctgaagctt gggctgaggt    2040
ccagagacag ctcagcattg tggtgacagc cctggagggt gcggcagcca ccctgaggcc    2100
tgtggctgac ctctgacccc agccctcttt cttcagccct ccctttactc cggtgcttta    2160
tatttacaaa gtgctttgtg ttttttaaaa gtcttt                              2197
```

<210> SEQ ID NO 61
<211> LENGTH: 699
<212> TYPE: PRT
<213> ORGANISM: Homo sapiens
<220> FEATURE:
<221> NAME/KEY: MOD_RES
<222> LOCATION: (100)
<223> OTHER INFORMATION: variable amino acid

<400> SEQUENCE: 61

```
Met Gln Trp Thr Lys Val Leu Gly Leu Gly Leu Gly Ala Ala Ala Leu
 1               5                  10                  15

Leu Gly Leu Gly Ile Ile Leu Gly His Phe Ala Ile Pro Lys Lys Ala
            20                  25                  30

Asn Ser Leu Ala Pro Gln Asp Leu Asp Leu Glu Ile Leu Glu Thr Val
        35                  40                  45

Met Gly Gln Leu Asp Ala His Arg Ile Arg Glu Asn Leu Arg Glu Leu
    50                  55                  60

Ser Arg Glu Pro His Leu Ala Ser Ser Pro Arg Asp Glu Asp Leu Val
65                  70                  75                  80

Gln Leu Leu Leu Gln Arg Trp Lys Asp Pro Glu Ser Gly Leu Asp Ser
                85                  90                  95

Ala Glu Ala Xaa Thr Tyr Glu Val Leu Leu Ser Phe Pro Ser Gln Glu
            100                 105                 110

Gln Pro Asn Val Val Asp Ile Val Gly Pro Thr Gly Gly Ile Ile His
        115                 120                 125

Ser Cys His Arg Thr Glu Glu Asn Val Thr Gly Glu Gln Gly Gly Pro
    130                 135                 140

Asp Val Val Gln Pro Tyr Ala Ala Tyr Ala Pro Ser Gly Thr Pro Gln
145                 150                 155                 160

Ala Val Asn Ala Ala Lys His Gly Val Ala Gly Val Leu Val Tyr Thr
                165                 170                 175

Asp Pro Ala Asp Ile Asn Asp Gly Leu Ser Ser Pro Asp Glu Thr Phe
            180                 185                 190

Pro Asn Ser Trp Tyr Leu Pro Ser Gly Val Glu Arg Gly Ser Tyr
        195                 200                 205

Tyr Glu Tyr Phe Gly Asp Pro Leu Thr Pro Tyr Leu Pro Ala Val Pro
    210                 215                 220

Ser Ser Phe Arg Val Asp Leu Ala Asn Val Ser Gly Phe Pro Pro Ile
225                 230                 235                 240

Pro Thr Gln Pro Ile Gly Phe Gln Asp Ala Arg Asp Leu Leu Cys Asn
                245                 250                 255
```

```
Leu Asn Gly Thr Leu Ala Pro Ala Thr Trp Gln Gly Ala Leu Gly Cys
        260                 265                 270

His Tyr Arg Leu Gly Pro Gly Phe Arg Pro Asp Gly Asp Phe Pro Ala
        275                 280                 285

Asp Ser Gln Val Asn Val Ser Val Tyr Asn Arg Leu Glu Leu Arg Asn
        290                 295                 300

Ser Ser Asn Val Leu Gly Ile Ile Arg Gly Ala Val Glu Pro Asp Arg
305                 310                 315                 320

Tyr Val Leu Tyr Gly Asn His Arg Asp Ser Trp Val His Gly Ala Val
                325                 330                 335

Asp Pro Ser Ser Gly Thr Ala Val Leu Leu Glu Leu Ser Arg Val Leu
            340                 345                 350

Gly Thr Leu Leu Lys Lys Gly Thr Trp Arg Pro Arg Ser Ile Val
                355                 360                 365

Phe Ala Ser Trp Gly Ala Glu Glu Phe Gly Leu Ile Gly Ser Thr Glu
        370                 375                 380

Phe Thr Glu Glu Phe Phe Asn Lys Leu Gln Glu Arg Thr Val Ala Tyr
385                 390                 395                 400

Ile Asn Val Asp Ile Ser Val Phe Ala Asn Ala Thr Leu Arg Val Gln
                405                 410                 415

Gly Thr Pro Pro Val Gln Ser Val Phe Ser Ala Thr Lys Glu Ile
        420                 425                 430

Arg Ser Pro Gly Pro Gly Asp Leu Ser Ile Tyr Asp Asn Trp Ile Arg
            435                 440                 445

Tyr Phe Asn Arg Ser Ser Pro Val Tyr Gly Leu Val Pro Ser Leu Gly
        450                 455                 460

Ser Leu Gly Ala Gly Ser Asp Tyr Ala Pro Phe Val His Phe Leu Gly
465                 470                 475                 480

Ile Ser Ser Met Asp Ile Ala Tyr Thr Tyr Asp Arg Ser Lys Thr Ser
                485                 490                 495

Ala Arg Ile Tyr Pro Thr Tyr His Thr Ala Phe Asp Thr Phe Asp Tyr
            500                 505                 510

Val Asp Lys Phe Leu Asp Pro Gly Phe Ser Ser His Gln Ala Val Ala
        515                 520                 525

Arg Thr Ala Gly Ser Val Ile Leu Arg Leu Ser Asp Ser Phe Phe Leu
        530                 535                 540

Pro Leu Lys Val Ser Asp Tyr Ser Glu Thr Leu Arg Ser Phe Leu Gln
545                 550                 555                 560

Ala Ala Gln Gln Asp Leu Gly Ala Leu Leu Glu Gln His Ser Ile Ser
                565                 570                 575

Leu Gly Pro Leu Val Thr Ala Val Glu Lys Phe Glu Ala Glu Ala Ala
            580                 585                 590

Ala Leu Gly Gln Arg Ile Ser Thr Leu Gln Lys Gly Ser Pro Asp Pro
        595                 600                 605

Leu Gln Val Arg Met Leu Asn Asp Gln Leu Met Leu Glu Arg Thr
        610                 615                 620

Phe Leu Asn Pro Arg Ala Phe Pro Glu Glu Arg Tyr Tyr Ser His Val
625                 630                 635                 640

Leu Trp Ala Pro Ser His Gly Leu Arg Ser His Ile Pro Gly Leu Ser
                645                 650                 655

Asn Ala Cys Ser Arg Ala Arg Asp Thr Ala Ser Gly Ser Glu Ala Trp
            660                 665                 670
```

```
Ala Glu Val Gln Arg Gln Leu Ser Ile Val Val Thr Ala Leu Glu Gly
        675                 680                 685

Ala Ala Ala Thr Leu Arg Pro Val Ala Asp Leu
        690                 695

<210> SEQ ID NO 62
<211> LENGTH: 2215
<212> TYPE: DNA
<213> ORGANISM: Homo sapiens
<220> FEATURE:
<221> NAME/KEY: modified_base
<222> LOCATION: (315)
<223> OTHER INFORMATION: a, c, g, t, unknown or other

<400> SEQUENCE: 62
gccaagagtc cgcaggatgc agtggacgaa ggtgttgggg ctggggctgg gggctgctgc      60
cctcttgggg ctgggatca tcctcggcca ctttgccatc cccaaaaaag ccaactcact     120 ggcccccag gacctggacc tggagatcct ggagaccgtc atgggcagc tggatgccca      180 caggatccgg gagaacctca gagaactctc cagggagcca cacctggcct ccagccctcg    240
ggatgaggac ctggtgcagc tgctgctgca gcgctggaag gacccagagt caggcctgga    300
ctcggccgag gcctncacgt acgaagtgct gctgtccttc cctagccagg agcagcccaa    360
cgtcgtggac atcgtgggcc ccactggggg catcatccac tcctgccacc ggactgagga    420
gaacgtgacc ggggagcaag gggggccaga tgtggtacaa ccctatgctg cctatgctcc    480
ttctggaacc ccacagggcc tcctcgtcta tgccaaccgg ggcgcggaag aagactttaa    540
ggagctacag actcagggca tcaaacttga aggcaccatt gccctgactc gatatggggg    600
tgtagggcgt ggggccaagg ctgtgaacgc tgccaagcac ggggtagctg gggtgctggt    660
gtacacagac cctgccgaca tcaacgatgg gctgagctca cccgacgaaa cctttcccaa    720
ctcctggtac ctgccccct caggagtgga gcgaggctcc tactacgagt attttgggga    780
ccctctgact ccctaccttc agccgtccc ctcttccttc cgcgtggacc ttgccaatgt     840 ctccggatt ccccccaattc ctacacagcc cattggcttc caggatgcaa gagacctgct    900
ctgccaggtg aatgtgagcg tctacaaccg cctggagctg aggaactctt ccaacgtcct    960
gggcatcatc cgtggggctg tggagcctga tcgctacgtg ctgtatggga ccaccgaga   1020 cagctgggtg cacggggctg tggaccccag cagtggcacc gccgtcctcc tggagctctc   1080
ccgtgtcctg gggaccctgc tgaagaaggg cacctggcgt cctcgcagat caatcgtgtt   1140
tgcgagctgg ggggctgagg agtttgggct cattggctcc acggaattca cagaagagtt   1200
cttcaacaag ctgcaggagc gcacggtggc ctacatcaac gtggacatct cggtgttt gc   1260 caacgctacc cttagggtgc aggggacgcc ccctgtccag agcgtcgtct tctctgcaac   1320
caaagagatc cgctcaccag gccctggcga cctgagcatc tacgacaact ggatccggta   1380
cttcaaccgc agcagcccgg tgtacggcct ggtcccagc ttgggttctc tgggtgctgg    1440
cagcgactat gcacccttcg ttcacttcct gggcatctcc tccatggaca ttgcctatac   1500
ctatgaccgg agcaagactt cagccaggat ctaccccacc taccacacag cctttgacac   1560 cttttgactat gtggacaagt ttttggaccc gggcttcagc agccatcagg ctgtggcccg   1620
gacagcgggg agtgtgattc tccggctcag tgacagcttc ttcctgcccc tcaaagtcag   1680
tgactacagt gagacactcc gcagcttcct gcaggcagcc cagcaagatc ttggggcccct  1740 gctggagcag cacagcatca gcctgggcc tctggtgact gcagtggaga agtttgaggc    1800
agaagctgca gccttgggcc aacgcatatc aacactgcag aagggcagcc ctgacccccct  1860
```

```
gcaggtccgg atgctcaatg accagttgat gctcttggaa cggacctttc tgaaccctag   1920
agccttccca gaggaacgct actacagcca tgtgctctgg gcaccttcgc acgggctccg   1980
tagtcacatt ccggggctat ccaatgcctg ctccagggcc agggacacag cttctggatc   2040
tgaagcttgg gctgaggtcc agagacagct cagcattgtg gtgacagccc tggagggtgc   2100
ggcagccacc ctgaggcctg tggctgacct ctgaccccag ccctctttct tcagccctcc   2160
ctttactccg gtgctttata tttacaaagt gctttgtgtt ttttaaaagt ctttt        2215
```

<210> SEQ ID NO 63
<211> LENGTH: 705
<212> TYPE: PRT
<213> ORGANISM: Homo sapiens
<220> FEATURE:
<221> NAME/KEY: MOD_RES
<222> LOCATION: (100)
<223> OTHER INFORMATION: variable amino acid

<400> SEQUENCE: 63

```
Met Gln Trp Thr Lys Val Leu Gly Leu Gly Leu Gly Ala Ala Ala Leu
 1               5                  10                  15

Leu Gly Leu Gly Ile Ile Leu Gly His Phe Ala Ile Pro Lys Lys Ala
                20                  25                  30

Asn Ser Leu Ala Pro Gln Asp Leu Asp Leu Glu Ile Leu Glu Thr Val
            35                  40                  45

Met Gly Gln Leu Asp Ala His Arg Ile Arg Glu Asn Leu Arg Glu Leu
        50                  55                  60

Ser Arg Glu Pro His Leu Ala Ser Ser Pro Arg Asp Glu Asp Leu Val
 65                  70                  75                  80

Gln Leu Leu Leu Gln Arg Trp Lys Asp Pro Glu Ser Gly Leu Asp Ser
                85                  90                  95

Ala Glu Ala Xaa Thr Tyr Glu Val Leu Leu Ser Phe Pro Ser Gln Glu
            100                 105                 110

Gln Pro Asn Val Val Asp Ile Val Gly Pro Thr Gly Gly Ile Ile His
        115                 120                 125

Ser Cys His Arg Thr Glu Glu Asn Val Thr Gly Glu Gln Gly Gly Pro
130                 135                 140

Asp Val Val Gln Pro Tyr Ala Ala Tyr Ala Pro Ser Gly Thr Pro Gln
145                 150                 155                 160

Gly Leu Leu Val Tyr Ala Asn Arg Gly Ala Glu Glu Asp Phe Lys Glu
                165                 170                 175

Leu Gln Thr Gln Gly Ile Lys Leu Glu Gly Thr Ile Ala Leu Thr Arg
            180                 185                 190

Tyr Gly Gly Val Gly Arg Gly Ala Lys Ala Val Asn Ala Ala Lys His
        195                 200                 205

Gly Val Ala Gly Val Leu Val Tyr Thr Asp Pro Ala Asp Ile Asn Asp
    210                 215                 220

Gly Leu Ser Ser Pro Asp Glu Thr Phe Pro Asn Ser Trp Tyr Leu Pro
225                 230                 235                 240

Pro Ser Gly Val Glu Arg Gly Ser Tyr Tyr Glu Tyr Phe Gly Asp Pro
                245                 250                 255

Leu Thr Pro Tyr Leu Pro Ala Val Pro Ser Ser Phe Arg Val Asp Leu
            260                 265                 270

Ala Asn Val Ser Gly Phe Pro Pro Ile Pro Thr Gln Pro Ile Gly Phe
        275                 280                 285
```

-continued

```
Gln Asp Ala Arg Asp Leu Leu Ser Gln Val Asn Val Ser Val Tyr Asn
    290                 295                 300
Arg Leu Glu Leu Arg Asn Ser Ser Asn Val Leu Gly Ile Ile Arg Gly
305                 310                 315                 320
Ala Val Glu Pro Asp Arg Tyr Val Leu Tyr Gly Asn His Arg Asp Ser
                325                 330                 335
Trp Val His Gly Ala Val Asp Pro Ser Ser Gly Thr Ala Val Leu Leu
            340                 345                 350
Glu Leu Ser Arg Val Leu Gly Thr Leu Leu Lys Lys Gly Thr Trp Arg
        355                 360                 365
Pro Arg Arg Ser Ile Val Phe Ala Ser Trp Gly Ala Glu Glu Phe Gly
    370                 375                 380
Leu Ile Gly Ser Thr Glu Phe Thr Glu Glu Phe Phe Asn Lys Leu Gln
385                 390                 395                 400
Glu Arg Thr Val Ala Tyr Ile Asn Val Asp Ile Ser Val Phe Ala Asn
                405                 410                 415
Ala Thr Leu Arg Val Gln Gly Thr Pro Pro Val Gln Ser Val Val Phe
            420                 425                 430
Ser Ala Thr Lys Glu Ile Arg Ser Pro Gly Pro Gly Asp Leu Ser Ile
        435                 440                 445
Tyr Asp Asn Trp Ile Arg Tyr Phe Asn Arg Ser Ser Pro Val Tyr Gly
    450                 455                 460
Leu Val Pro Ser Leu Gly Ser Leu Gly Ala Gly Ser Asp Tyr Ala Pro
465                 470                 475                 480
Phe Val His Phe Leu Gly Ile Ser Ser Met Asp Ile Ala Tyr Thr Tyr
                485                 490                 495
Asp Arg Ser Lys Thr Ser Ala Arg Ile Tyr Pro Thr Tyr His Thr Ala
            500                 505                 510
Phe Asp Thr Phe Asp Tyr Val Asp Lys Phe Leu Asp Pro Gly Phe Ser
        515                 520                 525
Ser His Gln Ala Val Ala Arg Thr Ala Gly Ser Val Ile Leu Arg Leu
    530                 535                 540
Ser Asp Ser Phe Phe Leu Pro Leu Lys Val Ser Asp Tyr Ser Glu Thr
545                 550                 555                 560
Leu Arg Ser Phe Leu Gln Ala Ala Gln Gln Asp Leu Gly Ala Leu Leu
                565                 570                 575
Glu Gln His Ser Ile Ser Leu Gly Pro Leu Val Thr Ala Val Glu Lys
            580                 585                 590
Phe Glu Ala Glu Ala Ala Leu Gly Gln Arg Ile Ser Thr Leu Gln
        595                 600                 605
Lys Gly Ser Pro Asp Pro Leu Gln Val Arg Met Leu Asn Asp Gln Leu
    610                 615                 620
Met Leu Leu Glu Arg Thr Phe Leu Asn Pro Arg Ala Phe Pro Glu Glu
625                 630                 635                 640
Arg Tyr Tyr Ser His Val Leu Trp Ala Pro Ser His Gly Leu Arg Ser
                645                 650                 655
His Ile Pro Gly Leu Ser Asn Ala Cys Ser Arg Ala Arg Asp Thr Ala
            660                 665                 670
Ser Gly Ser Glu Ala Trp Ala Glu Val Gln Arg Gln Leu Ser Ile Val
        675                 680                 685
Val Thr Ala Leu Glu Gly Ala Ala Ala Thr Leu Arg Pro Val Ala Asp
    690                 695                 700
Leu
```

-continued

705

<210> SEQ ID NO 64
<211> LENGTH: 2549
<212> TYPE: DNA
<213> ORGANISM: Homo sapiens
<220> FEATURE:
<221> NAME/KEY: modified_base
<222> LOCATION: (315)
<223> OTHER INFORMATION: a, c, g, t, unknown or other

<400> SEQUENCE: 64

| | | | | | |
|---|---|---|---|---|---|
| gccaagagtc | cgcaggatgc | agtggacgaa | ggtgttgggg | ctggggctgg | gggctgctgc | 60 |
| cctcttgggg | ctgggatca | tcctcggcca | ctttgccatc | cccaaaaaag | ccaactcact | 120 |
| ggcccccag | gacctggacc | tggagatcct | ggagaccgtc | atgggcagc | tggatgccca | 180 |
| caggatccgg | gagaacctca | gagaactctc | cagggagcca | cacctggcct | ccagccctcg | 240 |
| ggatgaggac | ctggtgcagc | tgctgctgca | gcgctggaag | gacccagagt | caggcctgga | 300 |
| ctcggccgag | gcctncacgt | acgaagtgct | gctgtccttc | cctagccagg | agcagcccaa | 360 |
| cgtcgtggac | atcgtgggcc | ccactggggg | catcatccac | tcctgccacc | ggactgagga | 420 |
| gaacgtgacc | ggggagcaag | gggggccaga | tgtggtacaa | ccctatgctg | cctatgctcc | 480 |
| ttctggaacc | ccacagggcc | tcctcgtcta | tgccaaccgg | ggcgcggaag | aagactttaa | 540 |
| ggagctacag | actcagggca | tcaaacttga | aggcaccatt | gccctgactc | gatatggggg | 600 |
| tgtagggcgt | ggggccaagg | ctgtgaacgc | tgccaagcac | ggggtagctg | gggtgctggt | 660 |
| gtacacagac | cctgccgaca | tcaacgatgg | gctgagctca | cccgacgaaa | cctttcccaa | 720 |
| ctcctggtac | ctgccccct | caggagtgga | gcgaggctcc | tactacgagt | attttgggga | 780 |
| ccctctgact | ccctaccttc | cagccgtccc | ctcttccttc | cgcgtggacc | ttgccaatgt | 840 |
| ctccggattt | cccccaattc | ctacacagcc | cattggcttc | caggatgcaa | gagacctgct | 900 |
| ctgtaacctc | aacggaactt | tggccccagc | cacctggcag | ggagcactgg | gctgccacta | 960 |
| caggttgggt | cccggcttcc | ggcctgacgg | agacttccca | gcagacagcc | aggtgaatgt | 1020 |
| gagcgtctac | aaccgcctgg | agctgaggaa | ctcttccaac | gtcctgggca | tcatccgtgg | 1080 |
| ggctgtggag | cctgtgagcg | tctacaaccg | cctggagctg | aggaactctt | ccaacgtcct | 1140 |
| gggcatcatc | cgtgggctg | tggagcctgg | tgagccctcc | tcttgctgcc | tgcacccag | 1200 |
| gcccctgctc | tgctctggat | gccgctgtcc | tcatccagcc | ctgccttgc | caccacccag | 1260 |
| cccagctccc | cctgcccacc | tctccctctc | ctctggttct | ctgccccttt | tcctctggcc | 1320 |
| aggatcgcta | cgtgctgtat | gggaaccacc | gagacagctg | ggtgcacggg | gctgtggacc | 1380 |
| ccagcagtgg | caccgccgtc | ctcctggagc | tctcccgtgt | cctggggacc | ctgctgaaga | 1440 |
| agggcacctg | gcgtcctcgc | agatcaatcg | tgtttgcgag | ctgggggct | gaggagtttg | 1500 |
| ggctcattgg | ctccacggaa | ttcacagaag | agttcttcaa | caagctgcag | gagcgcacgg | 1560 |
| tggcctacat | caacgtggac | atctcggtgt | ttgccaacgc | taccctagg | gtgcagggga | 1620 |
| cgcccctgt | ccagagcgtc | gtcttctctg | caaccaaaga | gatccgctca | ccaggccctg | 1680 |
| gcgacctgag | catctacgac | aactggatcc | ggtacttcaa | ccgcagcagc | ccggtgtacg | 1740 |
| gcctggtccc | cagcttgggt | tctctgggtg | ctggcagcga | ctatgcaccc | ttcgttcact | 1800 |
| tcctgggcat | ctcctccatg | gacattgcct | ataccctatga | ccggagcaag | acttcagcca | 1860 |
| ggatctaccc | cacctaccac | acagcctttg | acacctttga | ctatgtggac | aagttttgg | 1920 |
| acccgggctt | cagcagccat | caggctgtgg | cccggacagc | ggggagtgtg | attctccggc | 1980 |

-continued

```
tcagtgacag cttcttcctg cccctcaaag tcagtgacta cagtgagaca ctccgcagct     2040
tcctgcaggc agcccagcaa gatcttgggg ccctgctgga gcagcacagc atcagcctgg     2100
ggcctctggt gactgcagtg gagaagtttg aggcagaagc tgcagccttg ggccaacgca     2160
tatcaacact gcagaagggc agccctgacc ccctgcaggt ccggatgctc aatgaccagt     2220
tgatgctctt ggaacggacc tttctgaacc ctagagcctt cccagaggaa cgctactaca     2280
gccatgtgct ctgggcacct tcgcacgggc tccgtagtca cattccgggg ctatccaatg     2340
cctgctccag ggccagggac acagcttctg gatctgaagc ttgggctgag gtccagagac     2400
agctcagcat tgtggtgaca gccctggagg gtgcggcagc caccctgagg cctgtggctg     2460
acctctgacc ccagccctct ttcttcagcc ctcccttttac tccggtgctt tatatttaca     2520
aagtgctttg tgttttttaa aagtctttt                                       2549
```

<210> SEQ ID NO 65
<211> LENGTH: 791
<212> TYPE: PRT
<213> ORGANISM: Homo sapiens
<220> FEATURE:
<221> NAME/KEY: MOD_RES
<222> LOCATION: (100)
<223> OTHER INFORMATION: variable amino acid

<400> SEQUENCE: 65

```
Met Gln Trp Thr Lys Val Leu Gly Leu Gly Leu Gly Ala Ala Ala Leu
  1               5                  10                  15

Leu Gly Leu Gly Ile Ile Leu Gly His Phe Ala Ile Pro Lys Lys Ala
             20                  25                  30

Asn Ser Leu Ala Pro Gln Asp Leu Asp Leu Glu Ile Leu Glu Thr Val
         35                  40                  45

Met Gly Gln Leu Asp Ala His Arg Ile Arg Glu Asn Leu Arg Glu Leu
     50                  55                  60

Ser Arg Glu Pro His Leu Ala Ser Ser Pro Arg Asp Glu Asp Leu Val
 65                  70                  75                  80

Gln Leu Leu Leu Gln Arg Trp Lys Asp Pro Glu Ser Gly Leu Asp Ser
                 85                  90                  95

Ala Glu Ala Xaa Thr Tyr Glu Val Leu Leu Ser Phe Pro Ser Gln Glu
            100                 105                 110

Gln Pro Asn Val Val Asp Ile Val Gly Pro Thr Gly Gly Ile Ile His
        115                 120                 125

Ser Cys His Arg Thr Glu Glu Asn Val Thr Gly Glu Gln Gly Gly Pro
    130                 135                 140

Asp Val Val Gln Pro Tyr Ala Tyr Ala Pro Ser Gly Thr Pro Gln
145                 150                 155                 160

Gly Leu Leu Val Tyr Ala Asn Arg Gly Ala Glu Glu Asp Phe Lys Glu
                165                 170                 175

Leu Gln Thr Gln Gly Ile Lys Leu Glu Gly Thr Ile Ala Leu Thr Arg
            180                 185                 190

Tyr Gly Gly Val Gly Arg Gly Ala Lys Ala Val Asn Ala Ala Lys His
        195                 200                 205

Gly Val Ala Gly Val Leu Val Tyr Thr Asp Pro Ala Asp Ile Asn Asp
    210                 215                 220

Gly Leu Ser Ser Pro Asp Glu Thr Phe Pro Asn Ser Trp Tyr Leu Pro
225                 230                 235                 240

Pro Ser Gly Val Glu Arg Gly Ser Tyr Tyr Glu Tyr Phe Gly Asp Pro
```

-continued

```
                245                 250                 255
Leu Thr Pro Tyr Leu Pro Ala Val Pro Ser Ser Phe Arg Val Asp Leu
            260                 265                 270
Ala Asn Val Ser Gly Phe Pro Ile Pro Thr Gln Pro Ile Gly Phe
        275                 280                 285
Gln Asp Ala Arg Asp Leu Leu Cys Asn Leu Asn Gly Thr Leu Ala Pro
    290                 295                 300
Ala Thr Trp Gln Gly Ala Leu Gly Cys His Tyr Arg Leu Gly Pro Gly
305                 310                 315                 320
Phe Arg Pro Asp Gly Asp Phe Pro Ala Asp Ser Gln Val Asn Val Ser
                325                 330                 335
Val Tyr Asn Arg Leu Glu Leu Arg Asn Ser Ser Asn Val Leu Gly Ile
            340                 345                 350
Ile Arg Gly Ala Val Glu Pro Gly Glu Pro Ser Ser Cys Cys Leu His
        355                 360                 365
Pro Arg Pro Leu Leu Cys Ser Gly Cys Arg Cys Pro His Pro Ala Leu
    370                 375                 380
Pro Leu Pro Pro Pro Ser Pro Ala Pro Pro Ala His Leu Ser Leu Ser
385                 390                 395                 400
Ser Gly Ser Leu Pro Leu Phe Leu Trp Pro Asp Arg Tyr Val Leu Tyr
                405                 410                 415
Gly Asn His Arg Asp Ser Trp Val His Gly Ala Val Asp Pro Ser Ser
            420                 425                 430
Gly Thr Ala Val Leu Leu Glu Leu Ser Arg Val Leu Gly Thr Leu Leu
        435                 440                 445
Lys Lys Gly Thr Trp Arg Pro Arg Arg Ser Ile Val Phe Ala Ser Trp
    450                 455                 460
Gly Ala Glu Glu Phe Gly Leu Ile Gly Ser Thr Glu Phe Thr Glu Glu
465                 470                 475                 480
Phe Phe Asn Lys Leu Gln Glu Arg Thr Val Ala Tyr Ile Asn Val Asp
                485                 490                 495
Ile Ser Val Phe Ala Asn Ala Thr Leu Arg Val Gln Gly Thr Pro Pro
            500                 505                 510
Val Gln Ser Val Val Phe Ser Ala Thr Lys Glu Ile Arg Ser Pro Gly
        515                 520                 525
Pro Gly Asp Leu Ser Ile Tyr Asp Asn Trp Ile Arg Tyr Phe Asn Arg
    530                 535                 540
Ser Ser Pro Val Tyr Gly Leu Val Pro Ser Leu Gly Ser Leu Gly Ala
545                 550                 555                 560
Gly Ser Asp Tyr Ala Pro Phe Val His Phe Leu Gly Ile Ser Ser Met
                565                 570                 575
Asp Ile Ala Tyr Thr Tyr Asp Arg Ser Lys Thr Ser Ala Arg Ile Tyr
            580                 585                 590
Pro Thr Tyr His Thr Ala Phe Asp Thr Phe Asp Tyr Val Asp Lys Phe
        595                 600                 605
Leu Asp Pro Gly Phe Ser Ser His Gln Ala Val Ala Arg Thr Ala Gly
    610                 615                 620
Ser Val Ile Leu Arg Leu Ser Asp Ser Phe Phe Leu Pro Leu Lys Val
625                 630                 635                 640
Ser Asp Tyr Ser Glu Thr Leu Arg Ser Phe Leu Gln Ala Ala Gln Gln
                645                 650                 655
Asp Leu Gly Ala Leu Leu Glu Gln His Ser Ile Ser Leu Gly Pro Leu
            660                 665                 670
```

```
Val Thr Ala Val Glu Lys Phe Glu Ala Glu Ala Ala Leu Gly Gln
            675                 680                 685

Arg Ile Ser Thr Leu Gln Lys Gly Ser Pro Asp Pro Leu Gln Val Arg
        690                 695                 700

Met Leu Asn Asp Gln Leu Met Leu Leu Glu Arg Thr Phe Leu Asn Pro
705                 710                 715                 720

Arg Ala Phe Pro Glu Glu Arg Tyr Tyr Ser His Val Leu Trp Ala Pro
                725                 730                 735

Ser His Gly Leu Arg Ser His Ile Pro Gly Leu Ser Asn Ala Cys Ser
                740                 745                 750

Arg Ala Arg Asp Thr Ala Ser Gly Ser Glu Ala Trp Ala Glu Val Gln
        755                 760                 765

Arg Gln Leu Ser Ile Val Val Thr Ala Leu Glu Gly Ala Ala Ala Thr
    770                 775                 780

Leu Arg Pro Val Ala Asp Leu
785                 790

<210> SEQ ID NO 66
<211> LENGTH: 2402
<212> TYPE: DNA
<213> ORGANISM: Homo sapiens
<220> FEATURE:
<221> NAME/KEY: modified_base
<222> LOCATION: (315)
<223> OTHER INFORMATION: a, c, g, t, unknown or other

<400> SEQUENCE: 66
gccaagagtc cgcaggatgc agtggacgaa ggtgttgggg ctggggctgg gggctgctgc      60
cctcttgggg ctgggatca tcctcggcca ctttgccatc cccaaaaaag ccaactcact     120
ggccccccag gacctggacc tggagatcct ggagaccgtc atgggcagc tggatgccca     180
caggatccgg gagaacctca gagaactctc cagggagcca cacctggcct ccagcccctcg   240
ggatgaggac ctggtgcagc tgctgctgca gcgctggaag gacccagagt caggcctgga   300
ctcggccgag gcctncacgt acgaagtgct gctgtccttc cctagccagg agcagcccaa   360
cgtcgtggac atcgtgggcc ccactggggg catcatccac tcctgccacc ggactgagga   420
gaacgtgacc ggggagcaag gggggccaga tgtggtacaa ccctatgctg cctatgctcc   480
ttctggaacc ccacagggcc tcctcgtcta tgccaaccgg ggcgcggaag aagactttaa   540
ggagctacag actcagggca tcaaacttga aggcaccatt gccctgactc gatatggggg   600
tgtagggcgt ggggccaagg ctgtgaacgc tgccaagcac ggggtagctg ggtgctggt    660
gtacacagac cctgccgaca tcaacgatgg gctgagctca cccgacgaaa cctttcccaa   720
ctcctggtac ctgcccccct caggagtgga gcgaggctcc tactacgagt attttgggga   780
ccctctgact ccctaccttc cagccgtccc ctcttccttc cgcgtggacc ttgccaatgt   840
ctccggattt cccccaattc ctacacagcc cattggcttc caggatgcaa gagacctgct   900
ctgtaacctc aacggaactt tggccccagc cacctggcag ggagcactgg gctgccacta   960
caggttgggt cccggcttcc ggcctgacgg agacttccca gcagacagcc aggtgaatgt  1020
gagcgtctac aaccgcctgg agctgaggaa ctcttccaac gtcctgggca tcatccgtgg  1080
ggctgtggag cctgatcgct acgtgctgta tgggaaccac cgagacagct gggtgcacgg  1140
ggctgtggac cccagcagtg gcaccgccgt cctcctggag ctctcccgtg tcctggggac  1200
cctgctgaag aagggcacct ggcgtcctcg cagatcaatc gtgtttgcga gctggggggc  1260
```

-continued

```
tgaggagttt gggctcattg gctccacgga attcacagaa gagttcttca acaagctgca   1320
ggagcgcacg gtggcctaca tcaacgtgga catctcggtg tttgccaacg ctacccttag   1380
ggtgcagggg acgcccctg tccagagcgt cgtcttctct gcaaccaaag agatccgctc    1440
accaggccct ggcgacctga gcatctacga caactggatc cggtacttca accgcagcag   1500
cccggtgtac ggcctggtcc ccagcttggg ttctctgggt gctggcagcg actatgcacc   1560
cttcgttcac ttcctgggca tctcctccat ggacattgcc tataccctat gccggagcaa   1620
gacttcagcc aggatctacc ccacctacca cacagccttt gacaccttg actatgtgga    1680 caagttttg acccggtga ggagggagac aagggcatc ctgagaccag acaggagag       1740 gctgaagact gagccctggc cttgtcacct tgccgcaggg cttcagcagc catcaggctg   1800
tggcccggac agcggggagt gtgattctcc ggctcagtga cagcttcttc ctgcccctca   1860
aagtcagtga ctacagtgag acactccgca gcttcctgca ggcagcccag caagatcttg   1920
gggccctgct ggagcagcac agcatcagcc tggggcctct ggtgactgca gtggagaagt   1980
ttgaggcaga agctgcagcc ttgggccaac gcatatcaac actgcagaag gcagccctg    2040 accccctgca ggtccggatg ctcaatgacc agttgatgct cttggaacgg acctttctga   2100
accctagagc cttcccagag gaacgctact acagccatgt gctctgggca ccttcgcacg   2160
ggctccgtag tcacattccg gggctatcca atgcctgctc cagggccagg acacagctt    2220 ctggatctga agcttgggct gaggtccaga gacagctcag cattgtggtg acagccctgg   2280
agggtgcggc agccaccctg aggcctgtgg ctgacctctg accccagccc tctttcttca   2340
gccctcccct tactccggtg ctttatattt acaaagtgct tgtgttttt taaaagtctt    2400 tt                                                                  2402
```

<210> SEQ ID NO 67
<211> LENGTH: 757
<212> TYPE: PRT
<213> ORGANISM: Homo sapiens
<220> FEATURE:
<221> NAME/KEY: MOD_RES
<222> LOCATION: (100)
<223> OTHER INFORMATION: variable amino acid

<400> SEQUENCE: 67

```
Met Gln Trp Thr Lys Val Leu Gly Leu Gly Leu Gly Ala Ala Ala Leu
 1               5                  10                  15

Leu Gly Leu Gly Ile Ile Leu Gly His Phe Ala Ile Pro Lys Lys Ala
            20                  25                  30

Asn Ser Leu Ala Pro Gln Asp Leu Asp Leu Glu Ile Leu Glu Thr Val
        35                  40                  45

Met Gly Gln Leu Asp Ala His Arg Ile Arg Glu Asn Leu Arg Glu Leu
    50                  55                  60

Ser Arg Glu Pro His Leu Ala Ser Ser Pro Arg Asp Glu Asp Leu Val
65                  70                  75                  80

Gln Leu Leu Leu Gln Arg Trp Lys Asp Pro Glu Ser Gly Leu Asp Ser
                85                  90                  95

Ala Glu Ala Xaa Thr Tyr Glu Val Leu Leu Ser Phe Pro Ser Gln Glu
            100                 105                 110

Gln Pro Asn Val Val Asp Ile Val Gly Pro Thr Gly Gly Ile Ile His
        115                 120                 125

Ser Cys His Arg Thr Glu Glu Asn Val Thr Gly Glu Gln Gly Gly Pro
    130                 135                 140
```

-continued

```
Asp Val Val Gln Pro Tyr Ala Ala Tyr Ala Pro Ser Gly Thr Pro Gln
145                 150                 155                 160

Gly Leu Leu Val Tyr Ala Asn Arg Gly Ala Glu Asp Phe Lys Glu
            165                 170                 175

Leu Gln Thr Gln Gly Ile Lys Leu Glu Gly Thr Ile Ala Leu Thr Arg
            180                 185                 190

Tyr Gly Gly Val Gly Arg Gly Ala Lys Ala Val Asn Ala Ala Lys His
        195                 200                 205

Gly Val Ala Gly Val Leu Val Tyr Thr Asp Pro Ala Asp Ile Asn Asp
210                 215                 220

Gly Leu Ser Ser Pro Asp Glu Thr Phe Pro Asn Ser Trp Tyr Leu Pro
225                 230                 235                 240

Pro Ser Gly Val Glu Arg Gly Ser Tyr Tyr Glu Tyr Phe Gly Asp Pro
                245                 250                 255

Leu Thr Pro Tyr Leu Pro Ala Val Pro Ser Ser Phe Arg Val Asp Leu
            260                 265                 270

Ala Asn Val Ser Gly Phe Pro Pro Ile Pro Thr Gln Pro Ile Gly Phe
        275                 280                 285

Gln Asp Ala Arg Asp Leu Leu Cys Asn Leu Asn Gly Thr Leu Ala Pro
290                 295                 300

Ala Thr Trp Gln Gly Ala Leu Gly Cys His Tyr Arg Leu Gly Pro Gly
305                 310                 315                 320

Phe Arg Pro Asp Gly Asp Phe Pro Ala Asp Ser Gln Val Asn Val Ser
                325                 330                 335

Val Tyr Asn Arg Leu Glu Leu Arg Asn Ser Ser Asn Val Leu Gly Ile
            340                 345                 350

Ile Arg Gly Ala Val Glu Pro Asp Arg Tyr Val Leu Tyr Gly Asn His
        355                 360                 365

Arg Asp Ser Trp Val His Gly Ala Val Asp Pro Ser Ser Gly Thr Ala
370                 375                 380

Val Leu Leu Glu Leu Ser Arg Val Leu Gly Thr Leu Leu Lys Lys Gly
385                 390                 395                 400

Thr Trp Arg Pro Arg Arg Ser Ile Val Phe Ala Ser Trp Gly Ala Glu
                405                 410                 415

Glu Phe Gly Leu Ile Gly Ser Thr Glu Phe Thr Glu Glu Phe Phe Asn
            420                 425                 430

Lys Leu Gln Glu Arg Thr Val Ala Tyr Ile Asn Val Asp Ile Ser Val
        435                 440                 445

Phe Ala Asn Ala Thr Leu Arg Val Gln Gly Thr Pro Pro Val Gln Ser
450                 455                 460

Val Val Phe Ser Ala Thr Lys Glu Ile Arg Ser Pro Gly Pro Gly Asp
465                 470                 475                 480

Leu Ser Ile Tyr Asp Asn Trp Ile Arg Tyr Phe Asn Arg Ser Ser Pro
                485                 490                 495

Val Tyr Gly Leu Val Pro Ser Leu Gly Ser Leu Gly Ala Gly Ser Asp
            500                 505                 510

Tyr Ala Pro Phe Val His Phe Leu Gly Ile Ser Ser Met Asp Ile Ala
        515                 520                 525

Tyr Thr Tyr Asp Arg Ser Lys Thr Ser Ala Arg Ile Tyr Pro Thr Tyr
530                 535                 540

His Thr Ala Phe Asp Thr Phe Asp Tyr Val Asp Lys Phe Leu Asp Pro
545                 550                 555                 560

Gly Glu Glu Gly Asp Lys Gly His Pro Glu Thr Arg Thr Gly Glu Ala
```

-continued

```
                565                 570                 575
Glu Asp Phe Ser Ser His Gln Ala Val Ala Arg Thr Ala Gly Ser Val
            580                 585                 590
Ile Leu Arg Leu Ser Asp Ser Phe Phe Leu Pro Leu Lys Val Ser Asp
        595                 600                 605
Tyr Ser Glu Thr Leu Arg Ser Phe Leu Gln Ala Ala Gln Gln Asp Leu
    610                 615                 620
Gly Ala Leu Leu Glu Gln His Ser Ile Ser Leu Gly Pro Leu Val Thr
625                 630                 635                 640
Ala Val Glu Lys Phe Glu Ala Glu Ala Ala Leu Gly Gln Arg Ile
                645                 650                 655
Ser Thr Leu Gln Lys Gly Ser Pro Asp Pro Leu Gln Val Arg Met Leu
            660                 665                 670
Asn Asp Gln Leu Met Leu Leu Glu Arg Thr Phe Leu Asn Pro Arg Ala
        675                 680                 685
Phe Pro Glu Glu Arg Tyr Tyr Ser His Val Leu Trp Ala Pro Ser His
    690                 695                 700
Gly Leu Arg Ser His Ile Pro Gly Leu Ser Asn Ala Cys Ser Arg Ala
705                 710                 715                 720
Arg Asp Thr Ala Ser Gly Ser Glu Ala Trp Ala Glu Val Gln Arg Gln
                725                 730                 735
Leu Ser Ile Val Val Thr Ala Leu Glu Gly Ala Ala Ala Thr Leu Arg
            740                 745                 750
Pro Val Ala Asp Leu
        755

<210> SEQ ID NO 68
<211> LENGTH: 2394
<212> TYPE: DNA
<213> ORGANISM: Homo sapiens
<220> FEATURE:
<221> NAME/KEY: modified_base
<222> LOCATION: (315)
<223> OTHER INFORMATION: a, c, g, t, unknown or other

<400> SEQUENCE: 68
gccaagagtc cgcaggatgc agtggacgaa ggtgttgggg ctggggctgg gggctgctgc      60
cctcttgggg ctgggatca tcctcggcca ctttgccatc cccaaaaaag ccaactcact     120 ggcccccag acctggacc tggagatcct ggagaccgtc atggggcagc tggatgccca     180
caggatccgg gagaacctca gagaactctc cagggagcca cacctggcct ccagccctcg     240
ggatgaggac ctggtgcagc tgctgctgca gcgctggaag gacccagagt caggcctgga     300
ctcggccgag gcctncacgt acgaagtgct gctgtccttc cctagccagg agcagcccaa     360
cgtcgtggac atcgtgggcc ccactggggg catcatccac tcctgccacc ggactgagga     420
gaacgtgacc ggggagcaag gggggccaga tgtggtacaa ccctatgctg cctatgctcc     480
ttctggaacc ccacagggcc tcctcgtcta tgccaaccgg ggcgcggaag aagactttaa     540
ggagctacag actcagggca tcaaacttga aggcaccatt gccctgactc gatatgggga     600
tgtagggcgt ggggccaagg ctgtgaacgc tgccaagcac ggggtagctg ggtgctggt     660 gtacacagac cctgccgaca tcaacgatgg gctgagctca cccgacgaaa cctttcccaa     720
ctcctggtac ctgcccccct caggagtgga gcgaggctcc tactacgagt attttgggga     780
ccctctgact ccctaccttc cagccgtccc ctcttccttc cgcgtggacc ttgccaatgt     840
ctccggattt ccccccaatt ctacacagcc cattggcttc caggatgcaa gagacctgct     900
```

-continued

```
ctgtaacctc aacggaactt tggccccagc cacctggcag ggagcactgg gctgccacta      960
caggttgggt cccggcttcc ggcctgacgg agacttccca gcagacagcc aggtgaatgt     1020
gagcgtctac aaccgcctgg agctgaggaa ctcttccaac gtcctgggca tcatccgtgg     1080
ggctgtggag cctgatcgct acgtgctgta tgggaaccac cgagacagct gggtgcacgg     1140
ggctgtggac cccagcagtg gcaccgccgt cctcctggag ctctcccgtg tcctggggac     1200
cctgctgaag aagggcacct ggcgtcctcg cagatcaatc gtgtttgcga gctgggggc      1260 tgaggagttt gggctcattg gctccacgga attcacagaa gagttcttca acaagctgca     1320
ggagcgcacg gtggcctaca tcaacgtgga catctcggtg tttgccaacg ctacccttag     1380
ggtgcagggg acgcccccctg tccagagcgt cgtcttctct gcaaccaaag agatccgctc   1440
accaggccct ggcgacctga gcatctacga caactggatc cggtacttca accgcagcag     1500
cccggtgtac ggcctggtcc ccagcttggg ttctctgggt gctggcagcg actatgcacc     1560
cttcgttcac ttcctgggca tctcctccat ggacattgcc tataccctatg accggagcaa   1620 gacttcagcc aggatctacc ccacctacca cacagccttt gacaccttttg actatgtgga   1680 caagtttttg gacccgggct tcagcagcca tcaggctgtg gcccggacag cggggagtgt    1740
gattctccgg ctcagtgaca gcttcttcct gcccctcaaa gtcagtgact acagtgagac    1800
actccgcagc ttcctgcagg cagcccagca agatcttggg gccctgctgg agcagcacag    1860
catcagcctg tatgcacagc cctgaccctg aggtatgggg agccctgcac ccccatgact    1920
gagccactgc ttgttcctca caggggggcct ctggtgactg cagtgagaa gtttgaggca    1980 gaagctgcag ccttgggcca acgcatatca acactgcaga agggcagccc tgaccccctg    2040
caggtccgga tgctcaatga ccagttgatg ctcttggaac ggacctttct gaaccctaga    2100
gccttcccag aggaacgcta ctacagccat gtgctctggg caccttcgca cgggctccgt    2160
agtcacattc cggggctatc caatgcctgc tccaggggcca gggacacagc ttctggatct   2220
gaagcttggg ctgaggtcca gagacagctc agcattgtgg tgacagccct ggagggtgcg    2280
gcagccaccc tgaggcctgt ggctgacctc tgaccccagc cctctttctt cagccctccc    2340
tttactccgg tgctttatat ttacaaagtg ctttgtgttt tttaaaagtc tttt           2394
```

<210> SEQ ID NO 69
<211> LENGTH: 757
<212> TYPE: PRT
<213> ORGANISM: Homo sapiens
<220> FEATURE:
<221> NAME/KEY: MOD_RES
<222> LOCATION: (100)
<223> OTHER INFORMATION: variable amino acid

<400> SEQUENCE: 69

```
Met Gln Trp Thr Lys Val Leu Gly Leu Gly Leu Gly Ala Ala Ala Leu
 1               5                  10                  15

Leu Gly Leu Gly Ile Ile Leu Gly His Phe Ala Ile Pro Lys Lys Ala
                20                  25                  30

Asn Ser Leu Ala Pro Gln Asp Leu Asp Leu Glu Ile Leu Glu Thr Val
            35                  40                  45

Met Gly Gln Leu Asp Ala His Arg Ile Arg Glu Asn Leu Arg Glu Leu
        50                  55                  60

Ser Arg Glu Pro His Leu Ala Ser Ser Pro Arg Asp Glu Asp Leu Val
 65                  70                  75                  80

Gln Leu Leu Leu Gln Arg Trp Lys Asp Pro Glu Ser Gly Leu Asp Ser
```

-continued

```
                   85                  90                  95
Ala Glu Ala Xaa Thr Tyr Glu Val Leu Leu Ser Phe Pro Ser Gln Glu
            100                 105                 110
Gln Pro Asn Val Val Asp Ile Val Gly Pro Thr Gly Gly Ile Ile His
            115                 120                 125
Ser Cys His Arg Thr Glu Glu Asn Val Thr Gly Glu Gln Gly Gly Pro
130                 135                 140
Asp Val Val Gln Pro Tyr Ala Ala Tyr Ala Pro Ser Gly Thr Pro Gln
145                 150                 155                 160
Gly Leu Leu Val Tyr Ala Asn Arg Gly Ala Glu Glu Asp Phe Lys Glu
            165                 170                 175
Leu Gln Thr Gln Gly Ile Lys Leu Glu Gly Thr Ile Ala Leu Thr Arg
            180                 185                 190
Tyr Gly Gly Val Gly Arg Gly Ala Lys Ala Val Asn Ala Ala Lys His
            195                 200                 205
Gly Val Ala Gly Val Leu Val Tyr Thr Asp Pro Ala Asp Ile Asn Asp
        210                 215                 220
Gly Leu Ser Ser Pro Asp Glu Thr Phe Pro Asn Ser Trp Tyr Leu Pro
225                 230                 235                 240
Pro Ser Gly Val Glu Arg Gly Ser Tyr Tyr Glu Tyr Phe Gly Asp Pro
                245                 250                 255
Leu Thr Pro Tyr Leu Pro Ala Val Pro Ser Ser Phe Arg Val Asp Leu
            260                 265                 270
Ala Asn Val Ser Gly Phe Pro Pro Ile Pro Thr Gln Pro Ile Gly Phe
            275                 280                 285
Gln Asp Ala Arg Asp Leu Leu Cys Asn Leu Asn Gly Thr Leu Ala Pro
290                 295                 300
Ala Thr Trp Gln Gly Ala Leu Gly Cys His Tyr Arg Leu Gly Pro Gly
305                 310                 315                 320
Phe Arg Pro Asp Gly Asp Phe Pro Ala Asp Ser Gln Val Asn Val Ser
                325                 330                 335
Val Tyr Asn Arg Leu Glu Leu Arg Asn Ser Ser Asn Val Leu Gly Ile
            340                 345                 350
Ile Arg Gly Ala Val Glu Pro Asp Arg Tyr Val Leu Tyr Gly Asn His
        355                 360                 365
Arg Asp Ser Trp Val His Gly Ala Val Asp Pro Ser Ser Gly Thr Ala
        370                 375                 380
Val Leu Leu Glu Leu Ser Arg Val Leu Gly Thr Leu Leu Lys Lys Gly
385                 390                 395                 400
Thr Trp Arg Pro Arg Arg Ser Ile Val Phe Ala Ser Trp Gly Ala Glu
                405                 410                 415
Glu Phe Gly Leu Ile Gly Ser Thr Glu Phe Thr Glu Phe Phe Asn
            420                 425                 430
Lys Leu Gln Glu Arg Thr Val Ala Tyr Ile Asn Val Asp Ile Ser Val
            435                 440                 445
Phe Ala Asn Ala Thr Leu Arg Val Gln Gly Thr Pro Pro Val Gln Ser
        450                 455                 460
Val Val Phe Ser Ala Thr Lys Glu Ile Arg Ser Pro Gly Pro Gly Asp
465                 470                 475                 480
Leu Ser Ile Tyr Asp Asn Trp Ile Arg Tyr Phe Asn Arg Ser Ser Pro
            485                 490                 495
Val Tyr Gly Leu Val Pro Ser Leu Gly Ser Leu Gly Ala Gly Ser Asp
            500                 505                 510
```

```
Tyr Ala Pro Phe Val His Phe Leu Gly Ile Ser Ser Met Asp Ile Ala
        515                 520                 525

Tyr Thr Tyr Asp Arg Ser Lys Thr Ser Ala Arg Ile Tyr Pro Thr Tyr
        530                 535                 540

His Thr Ala Phe Asp Thr Phe Asp Tyr Val Asp Lys Phe Leu Asp Pro
545                 550                 555                 560

Gly Phe Ser Ser His Gln Ala Val Ala Arg Thr Ala Gly Ser Val Ile
                565                 570                 575

Leu Arg Leu Ser Asp Ser Phe Phe Leu Pro Leu Lys Val Ser Asp Tyr
            580                 585                 590

Ser Glu Thr Leu Arg Ser Phe Leu Gln Ala Ala Gln Gln Asp Leu Gly
        595                 600                 605

Ala Leu Leu Glu Gln His Ser Ile Ser Leu Gly Met His Ser Pro Asp
        610                 615                 620

Pro Glu Val Trp Gly Ala Leu His Pro His Asp Gly Pro Leu Val Thr
625                 630                 635                 640

Ala Val Glu Lys Phe Glu Ala Glu Ala Ala Leu Gly Gln Arg Ile
                645                 650                 655

Ser Thr Leu Gln Lys Gly Ser Pro Asp Pro Leu Gln Val Arg Met Leu
                660                 665                 670

Asn Asp Gln Leu Met Leu Leu Glu Arg Thr Phe Leu Asn Pro Arg Ala
            675                 680                 685

Phe Pro Glu Glu Arg Tyr Tyr Ser His Val Leu Trp Ala Pro Ser His
        690                 695                 700

Gly Leu Arg Ser His Ile Pro Gly Leu Ser Asn Ala Cys Ser Arg Ala
705                 710                 715                 720

Arg Asp Thr Ala Ser Gly Ser Glu Ala Trp Ala Glu Val Gln Arg Gln
                725                 730                 735

Leu Ser Ile Val Val Thr Ala Leu Glu Gly Ala Ala Ala Thr Leu Arg
                740                 745                 750

Pro Val Ala Asp Leu
            755
```

CLONING AND CHARACTERISATION OF NOVEL MAMMALIAN PEPTIDASE

RELATED APPLICATIONS

This application is a national stage filing under 35 U.S.C. §371 of PCT International application PCT/GB99/02241, filed Jul. 14, 1999, which was published under PCT Article 21(2) in English. Foreign priority benefits are claimed under 35 U.S.C. §119(a)–(d) or 35 U.S.C. §365(b) of Great Britain application number GB 9815284.6, filed Jul. 14, 1998.

The present invention is concerned with novel mammalian peptidases and, in particular, with peptidases designated NAALAD-ase (N-acetylated alpha-linked acidic dipeptidases), cDNA sequences encoding for said peptidases and methods of identifying compounds which inhibit or enhance the activity or expression of such peptidases in addition to the compounds so identified.

NAALAD-ase I has previously been identified as a type II membrane glycoprotein with carboxypeptidase activity and sequence similarity to the transferrin receptor and which may be important in the progression of prostate cancer, being highly expressed in prostate tumours. In the CNS it has been postulated to have a role in modulating neuronal glutameric activity. The nucleotide and amino acid sequences for NAALAD-ase I have previously been identified (U.S. Pat. No. 5,538,686).

The present inventors have now surprisingly identified and cloned cDNA molecules which represent an expansion of this family of proteins and which enzymes have never previously been identified or characterised.

Therefore, according to a first aspect of the present invention, there is provided a cDNA molecule encoding a peptidase designated human NAALAD-ase L having the amino acid sequence illustrated in FIG. 1 or a functional equivalent or derivative or bioprecursor thereof. Preferably, the cDNA molecule comprises the sequence of nucleotides illustrated in FIG. 1. Also provided by the present invention are splice variants of the human NAALAD-ase L protein illustrated in FIG. 3 and preferably which splice variants are encoded by the nucleotide deletions or insertions indicated in FIG. 3.

Figure 4:
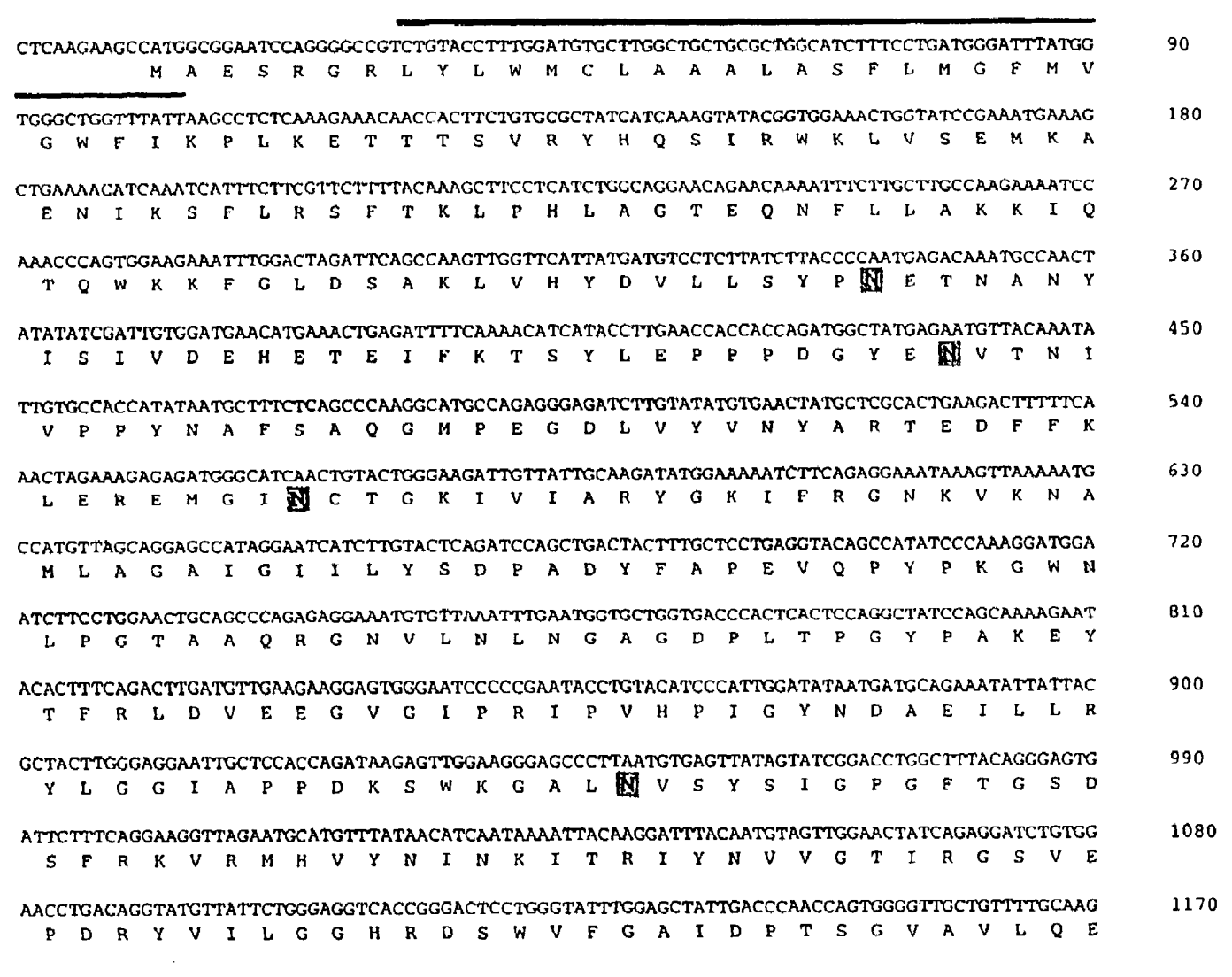

According to a further aspect of the present invention there is provided a cDNA molecule encoding a peptidase designated NAALAD-ase II or IV having the amino acid sequences as illustrated in FIGS. 4 and 5 respectively. Preferably, the cDNA comprises the sequences of nucleotides illustrated in FIGS. 4 and 5 respectively. Also encompassed within the present invention are nucleic acid molecules capable of hybridising to the cDNA molecules according to the invention.

Also provided by the present invention are the NAALAD-ase proteins encoded by the DNA sequences according to the invention. Therefore, according to a further aspect of the invention there is provided a human NAALAD-ase L protein having an amino acid sequence encoded by the nucleotide sequence illustrated in FIG. 1 or the sequence of FIG. 1 including the insertions or deletions illustrated in FIG. 3. Preferably, the NAALAD-ase L protein comprises a human NAALAD-ase L protein. Also provided by the present invention is a NAALAD-ase II and IV protein having amino acid sequences encoded by the nucleotide sequences illustrated in FIGS. 4 and 5 respectively or a functional equivalent, derivative or bioprecursor thereof and which protein is preferably of human origin. Preferably, the NAALAD-ase II and IV proteins comprise the amino acid sequences illustrated in FIGS. 4 and 5 respectively.

There is also provided by the invention an antisense molecule capable of hybridising to any of the nucleic acid sequences according to the invention, under high stringency conditions, which would be well known to those skilled in the art.

Stringency of hybridisation as used herein refers to conditions under which polynucleic acids are stable. The stability of hybrids is reflected in the melting temperature (Tm) of the hybrids. Tm can be approximated by the formula:

$$81.5° C. - 16.6(\log 10[Na^+] + 0.41(\% \; G\&C) - 600/l$$

wherein l is the length of the hybrids in nucleotides. Tm decreases approximately by 1–1.5° C. with every 1% decrease in sequence homology.

The cDNA molecules according to the invention may advantageously be included in an expression vector which may itself be used to transform, transfect or infect a host cell, which cell may be bacterial or eukaryotic in origin. Thus, advantageously, a range of cells, tissues or organisms may be transfected following incorporation of the appropriate cDNA into the expression vector. The vector may include an appropriate promoter, such as a cytomegalovirus promoter and optionally a sequence encoding a reporter molecule such as, for example, green fluorescent protein.

Regulatory elements required for expression include promoter sequences to bind RNA polymerase and transcription initiation sequences for ribosome binding. For example, a bacterial expression vector may include a promoter such as the lac promoter and for transcription initiations the Shine-Dalgarno sequence and the start codon AUG. Similarly, a eukaryotic expression vector may include a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art.

Thus, an expression vector refers to a recombinant DNA or RNA construct, such as a plasmid, a phage, recombinant virus or other vector that upon introduction into an appropriate host cell results inexpression of the DNA or RNA fragments. Appropriate expression vectors are well known to those skilled in the art and include those that are replicable in eukaryotic cells and/or prokaryotic cells and those that remain episomal or those which integrate into the host cell genome.

The antisense molecule capable of hybridising to the nucleic acid according to the invention may be used as a probe or as a medicament or in a pharmaceutical composition.

Nucleic acid molecules according to the invention may be inserted into the vectors described in an antisense orientation in order to provide for the production of antisense RNA. Antisense RNA or other antisense nucleic acids may be produced by synthetic means.

A further aspect of the invention comprises the host cell transformed, transfected or infected with the expression vector according to the invention, which cell preferably comprises a eukaryotic cell and more preferably a mammalian cell.

Incorporation of cloned DNA into a suitable expression vector for subsequent transformation of said cell and subsequent selection of the transformed cells is well known to those skilled in the art as provided in Sambrook et al (1989) Molecular Cloning, A Laboratory manual, Cold Spring Harbour Laboratory Press.

The present invention also comprises a transgenic cell, tissue or organism comprising a transgene, capable of expressing a NAALAD-ase protein according to the invention.

The term "transgene capable" of expression the protein according to the invention, as used herein should be taken to mean a suitable nucleic acid sequence which leads to the expression of said protein according to the invention or a protein having the same function or activity. The transgene may include, for example, genomic nucleic acid isolated from a human source or synthetic nucleic acid, inducing cDNA. The term "transgenic organism, tissue or cell" as used herein means any suitable organism and/or part of an organism, tissue or cell, that contains exogenous nucleic acid either stably integrated in the genome or in an extrachomosomal state. The transgenic cell is preferably a COS cell. Preferably, the transgene comprises an expression vector according to the invention.

The term "functional fragment" as used herein should be taken to mean a fragment of the gene encoding the NAALAD-ase protein according to the invention. For example, the gene may comprise deletions or mutations but may still encode a functional NAALAD-ase protein.

In accordance with the present invention, a defined nucleic acid sequence includes not only the identical nucleic acid but also minor base variations from the natural nucleic acid sequence, including in particular, substitutions in bases which result in a synonymous codon (a different codon specifying the same amino acid) due to the degenerate code in conservative amino acid substitution. The term "nucleic acid or cDNA sequence" also includes the complementary sequence to any single stranded sequence given which includes the definition given above regarding base variations.

Furthermore, a defined protein, polypeptide or amino acid sequence according to the invention includes not only the identical amino acid sequence but also minor amino acid variations from the natural amino acid sequence including conservative amino acid replacements (a replacement by an amino acid that is related in its side chains). Also included are amino acid sequences which vary from the natural amino acid but result in a polypeptide which is immunologically identical or similar to the polypeptide encoded by the naturally occurring sequence.

A further aspect of the invention provides a nucleic acid sequence of at least 15 nucleotides of a nucleic acid according to the invention and preferably from 15 to 50 nucleotides.

These sequences may, advantageously be used as probes or primers to initiate replication or the like. Such nucleic acid sequences may be produced according to techniques well known in the art, such as by recombinant or synthetic means. They may also be used in diagnostic kits or the like for detecting for the presence of a nucleic acid according to the invention. These tests generally comprise contacting the probe with a sample under hybridising conditions and detecting for the presence of any duplex formation between the probe and any nucleic acid in the sample.

Nucleic acid sequences according to the invention may also be produced using recombinant or synthetic means such as described in Sambrook et al (Molecular Cloning: A Laboratory Manual, 1989). Advantageously, human allelic variants or polymorphisms of the DNA according to the invention may be identified by, for example, probing DNA libraries from a range of individuals for example from different populations. Furthermore, nucleic acids and probes according to the invention may be used to sequence genomic DNA from patients using techniques well known in the art, such as the Sanger Dideoxy chain termination method, which may advantageously ascertain any predisposition of a patient to certain proliferative disorders.

The nucleic acids or oligonucleotides according to the invention may carry a revealing label. Suitable labels include radioisotopes such as $^{32}P$ or $^{35}S$, enzyme labels or other protein labels such as biotin or fluorescent markers. Such lables may be added to the nucleic acids or oligonucleotides of the invention and may be detected using known techniques per se.

Advantageously, human allelic variants or polymorphisms of the DNA molecule according to the invention may be identified by, for example, probing cDNA or genomic libraries from a range of individuals for example from different populations. Furthermore, nucleic acids and probes according to the invention may be used to sequence genomic DNA from patients using techniques well known in the art, such as the Sanger Dideoxy chain termination method, which may advantageously ascertain any predisposition of a patient to certain disorders associated with a NAALAD-ase according to the invention.

A nucleic acid sequence or protein identified according to the present invention may advantageously be used as a medicament, or in the preparation of a medicament for treating cancer or neurodegenerative disorders such as Alzheimer's disease or ALS, and other diseases or disorders mediated by peptidases according to the present invention. Advantageously, the cDNA and protein according to the invention in addition to nucleic acids hybridisable to the cDNA may also be included in a pharmaceutical composition together with a pharmaceutically acceptable carrier, diluent or excipient therefor. Thus, the composition may comprise antisense nucleic acids for use in, for example, gene therapy.

The present invention is further directed to inhibiting a NAALAD-ase according to the invention in vivo by the use of antisense technology. Antisense technology can be used to control gene expression through triple-helix formation or antisense DNA or RNA, both of which methods are based on binding of a polynucleotide to DNA or RNA. For example, the part of the DNA sequence coding for the mature protein of the present invention is used to design an antisense RNA oligonucleotide of from 10 to 50 base pairs in length. A DNA oligonucleotide is designed to be complementary to a region of the gene involved in transcription (triple-helix—see Lee et al. Nucl. Acids. Res., 6:3073 (1979); Cooney et al., Science, 241:456 (1988); and Dervan et al., Science, 251: 1360 (1991), thereby preventing transcription and the production of the peptidase. The antisense RNA oligonucleotide hybridises to the mRNA in vivo and blocks translation of an mRNA molecule into the NAALAD-ase.

Further provided by the present invention is a method of determining whether a compound is an inhibitor or an enhancer of NAALAD-ase activity, which method comprises contacting said compound in the present of [$^3$H]N-acetyl-L-aspartyl-L-glutamate (NAAG), and monitoring for the extent of hydrolysis of said NAAG.

NAALAD-ase peptides have previously been reported to have a role in prostate and other potential cancers in which case compounds identified as either inhibitors or enhancers of NAALAD-ase activity may advantageously be used as medicaments, or in the preparation of medicaments for treating cancers or neurodegenerative diseases such as Alzheimer's disease or ALS. These compounds may also be included in a pharmaceutical composition together with a pharmaceutically acceptable carrier, diluent or excipient therefor.

A further aspect of the present invention comprises a method of identifying a compound which is an inhibitor or an enhancer of expression of a NAALAD-ase protein according to the invention which method comprises contacting a host cell, tissue or organism expressing said protein with said compound and monitoring the expression of said protein compared to a control which comprises a cell expressing said peptidase according to the invention but which has not been contacted with said compound.

Preferably, said NAALAD-ase expressing cell comprises a host cell according to the invention or a transgenic cell, tissue or organism as described above. Preferably, said monitoring step comprises monitoring for the expression of said reporter molecule.

Compounds identified according to the above identified method may also be used as a medicament or in the preparation of a medicament for treating neurodegenerative disorders such as Alzheimer's disease, schizophrenia or ALS. Such compounds may also be included in a pharmaceutical composition together with a pharmaceutically acceptable carrier, diluent or excipient therefor to the present invention may also be prepared.

The NAALAD-ase antisense molecules or indeed the compounds identified as agonists or antagonists of the NAALAD-ase according to the invention may be used in the form of a pharmaceutical composition, which may be prepared according to procedures well known in the art. Preferred compositions include a pharmaceutically acceptable vehicle or diluent or excipient, such as for example, a physiological saline solution. Other pharmaceutically acceptable carriers including other non-toxic salts, sterile water or the like may also be used. A suitable buffer may also be present allowing the compositions to be lyophilized and stored in sterile conditions prior to reconstitution by the addition of sterile water for subsequent administration. Incorporation of NAALAD-ase into a solid or semi-solid biologically compatible matrix may be carried out which can be implanted into tissues requiring treatment.

Antibodies to the NAALAD-ase peptidases according to the present invention may, advantageously be prepared according to those techniques known in the art. Polyclonal antibodies against these peptides may be produced by immunizing animals using the selected peptides. Monoclonal antibodies are prepared using hybridoma technology by fusing antibody producing B cells from immunized animals with myeloma cells and selecting the resulting hybridoma cell line producing the desired antibody. Alternatively, monoclonal antibodies may be produced in in vitro techniques known to persons of ordinary skill in the art.

The antibodies prepared may be used in a method for detecting for the presence of said NAALAD-ase peptidases according to the invention by reacting said antibodies with a sample to be tested and identifying any protein bound thereto. A kit for such a method may also be provided and which comprises an antibody according to the aspect of the invention described above and means for reacting said antibody with said sample.

The carrier can also contain other pharmaceutically acceptable excipients for modifying other conditions such as pH, osmolarity, viscosity, sterility, lipophilicity, solubility or the like. Pharmaceutically acceptable excipients which permit sustained or delayed release following administration may also be included.

The NAALAD-ase protein or the nucleic acid molecules or compounds according to the invention may be administered orally. In this embodiment they may be encapsulated and combined with suitable carriers in solid dosage forms which would be well known to those skilled in the art.

As would be well known to those of skill in the art, the specific dosage regime may be calculated according to the body surface area of the patient or the volume of body space to be occupied, dependent upon the particular route of administration to be used. The amount of the composition actually administered will, however, be determined by a medical practitioner, based on the circumstances pertaining to the disorder to be treated, such as the severity of the symptoms, the composition to be administered, the age, weight, and response of the individual patient and the chosen route of administration.

A functionally active dose of such compounds according to the present invention comprises 300 ng/kg to 300 µg/kg in a rat. As aforementioned a skilled practitioner would arrive at an appropriate dosage for human subjects based on the relevant factors discussed.

The present invention may be more clearly understood by the following examples, which are purely exemplary, with reference to the accompanying drawings wherein:

FIG. 1: is an illustration of the nucleotide (SEQ ID NO: 34) and amino acid (SEQ ID NO: 35) sequences of human NAALAD-ase L. The nucleotide and predicted single letter code amino acid sequence are shown. the putative membrane spanning domain, deduced from hydrophilicity plots, is marked by a line. Potential N-glycosylation sites are shaded.

FIG. 2: is an alignment of the predicted protein sequences for human (SEQ ID NO: 35) and rat (SEQ ID NO: 36) NAALAD-ase L. The amino acid sequences were aligned using the ClustalW alignment program (EMBL, Heidelberg Germany). Amino acid residues identical in both proteins are highlighted in black. Amino acid residues are numbered in the right hand margin.

FIG. 3: is an illustration of alternative splicing of NAALAD-ase L. Amino acid sequence for NAALAD-ase L is shown (SEQ ID NO: 35). Sites at which putative DNA sequences are spliced out are marked by an arrow with the resulting (in-frame) amino acid deletions highlighted in bold italicised letters (SEQ ID NOS 37 & 38 respectively in order of appearance). Sites of putative intronic DNA insertion are marked by triangles, with the intronic DNA sequence shown above (SEQ ID NOS 41, 43 & 45 respectively in order of appearance). Resulting changes to the amino acid sequence are highlighted in bold italicised letters (SEQ ID NOS 42, 39, 44, 40 & 46 respectively in order of appearance). Numbering of amino acid residues is to the right.

FIG. 4: is a nucleotide (SEQ ID NO: 47) and amino acid sequence (SEQ ID NO: 48) of human NAALAD-ase II. The nucleotide and predicted one letter code amino acid sequence are shown. The putative membrane spanning domain, deduced from hydrophilicity plots, is marked by a line. Potential N-glycosylation sites are shaded.

FIG. 5: is a nucleotide sequence (SEQ ID NO: 49) and amino acid sequence (SEQ ID NO: 50) of human NAALAD-ase IV. The nucleotide and predicted one letter code amino acid sequence are shown. The putative membrane spanning domain, deduced from hydrophilicity plots, is marked by a line. Potential N-glycosylation sites are shaded.

Figure 6:
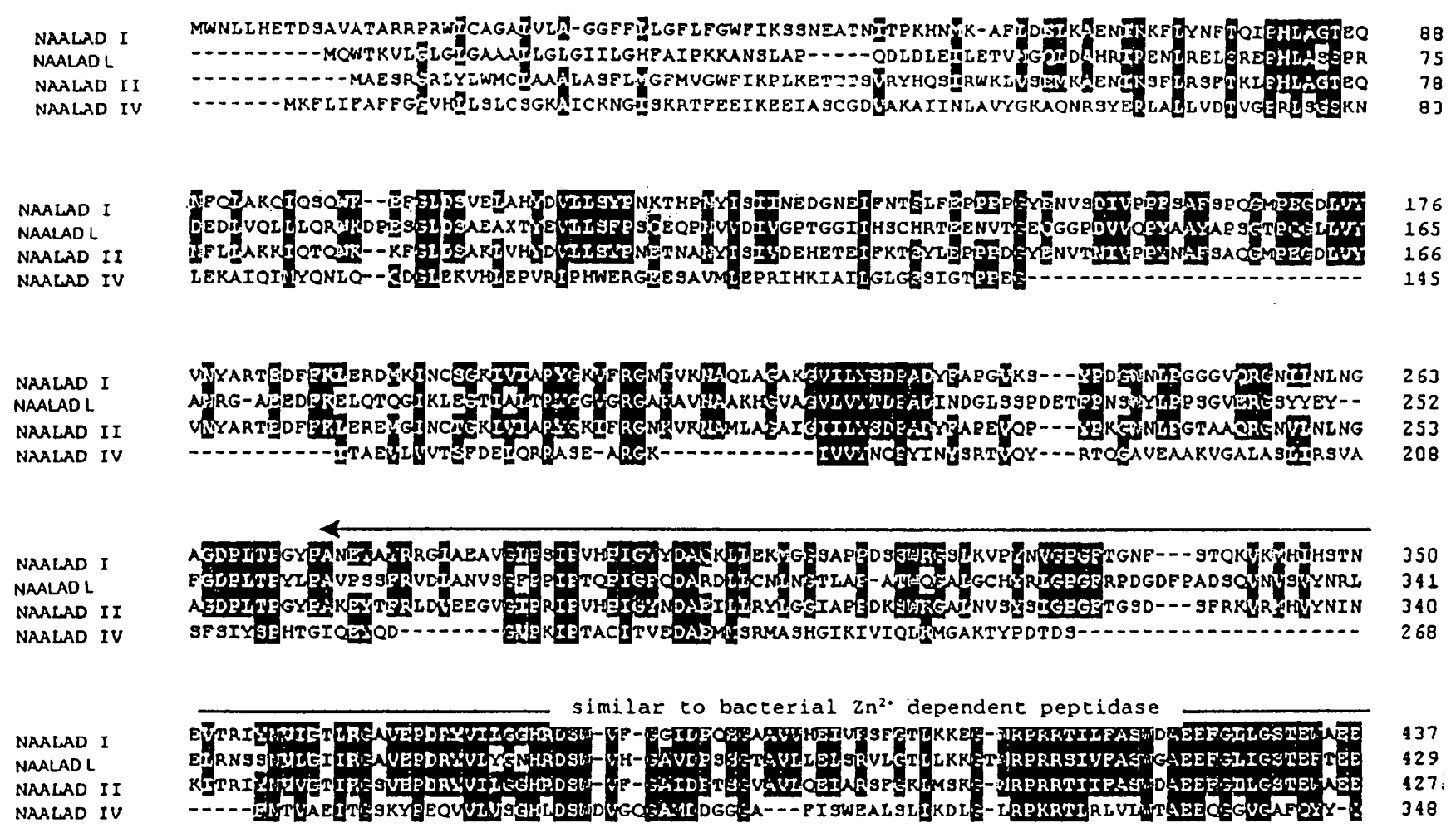
Figure 6:
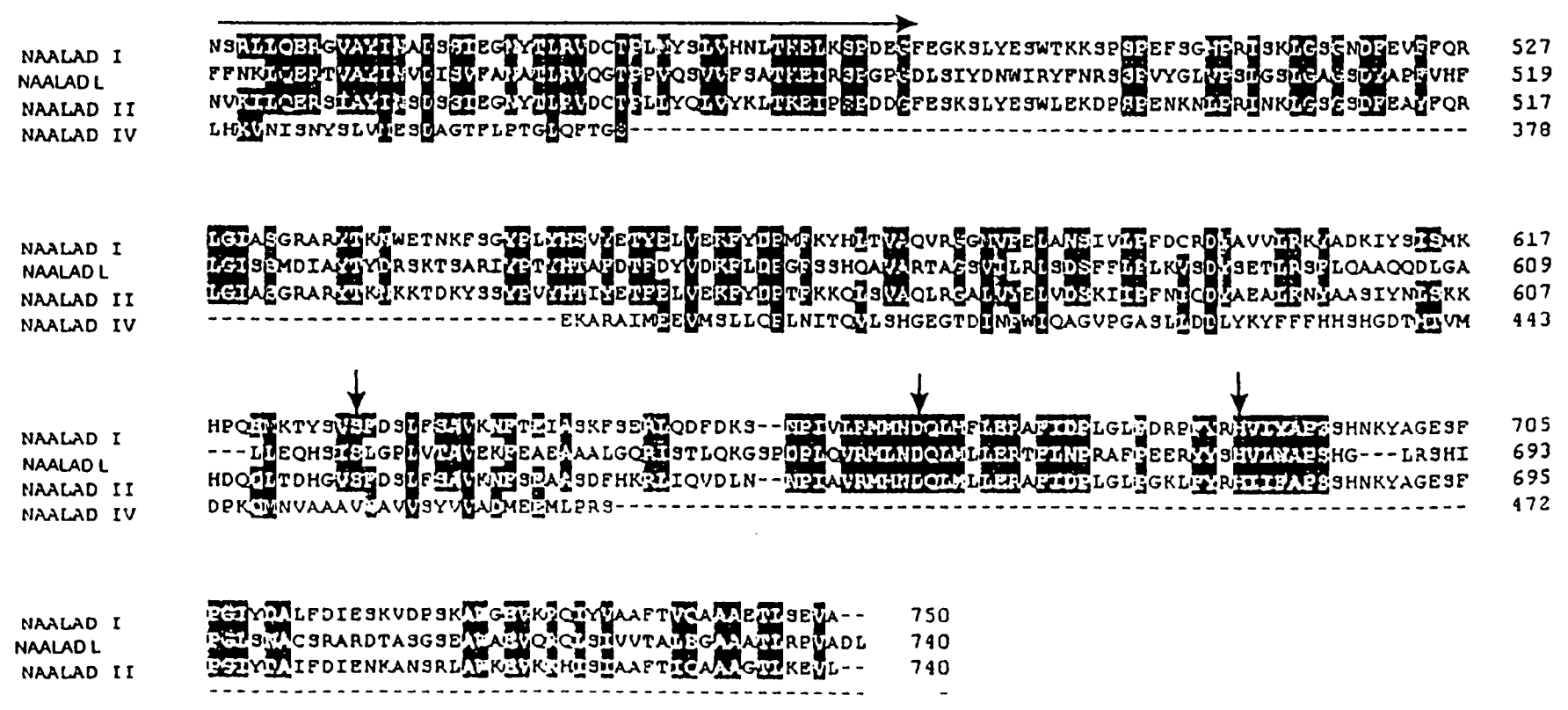

FIG. 6: is an alignment of the predicted protein sequences for human NAALAD-ases I (SEQ ID NO: 51), L (SEQ ID NO: 35), II (SEQ ID NO: 48) & IV (SEQ ID NO: 50). The amino acid sequences were aligned using the ClustalW alignment program. Amino acid residues identical to all four proteins are shaded in black. Amino acid residues identical to three of the four proteins are shaded in grey. Amino acid residues are numbered to the right. A putative $Zn^{2+}$ peptidase domain is highlighted between arrows and was identified by comparison to yeast and bacterial aminopeptidases. Putative residues involved in the catalytic site of the α/β hydrolase fold family of proteins are marked by three arrows (nucleophile-acid-base).

FIG. 7: is a phylogram of NAALAD-ase I, L, II and IV. The human and rat sequences were used and the alignments performed with the CLUSTALW program. The tree was constructed using the GCG 'Distances' program with standard parameters and the 'Growtree' program with the UPGMA method.

Figure 8:
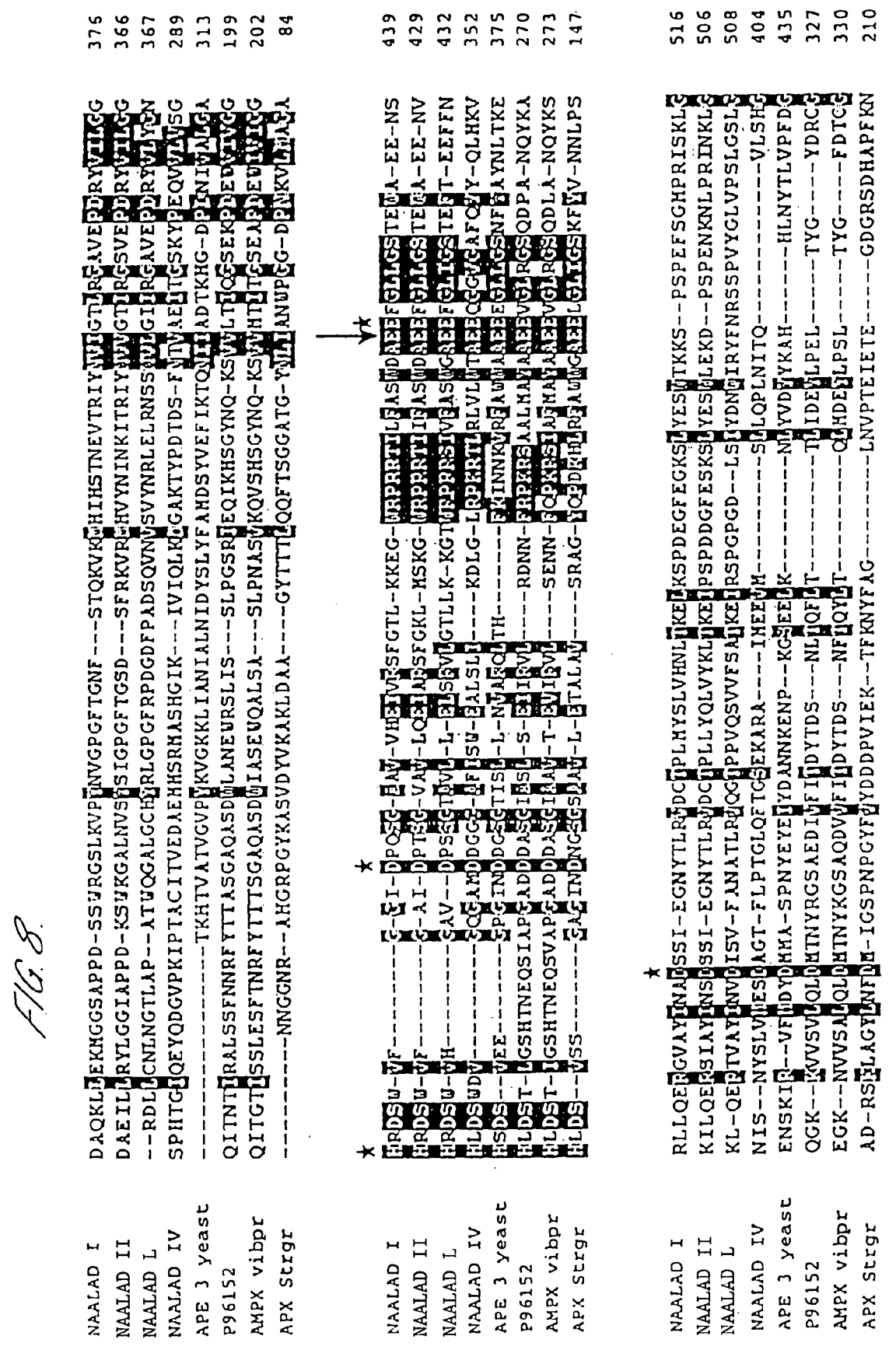

FIG. 8: is an alignment of the NAALAD-ase peptidase domains with related peptidases. Amino acid sequences were aligned using the standard settings of CLUSTALW alignment program. Similar amino acid residues conserved in proteins are shaded in black. Similar amino acid residues conserved in 80% of the proteins are shaded in dark grey. Similar amino acid residues conserved in 60–79% of the proteins are shaded in light grey. Amino acid residues are numbered to the right. Putative residues involved in zinc binding are marked by asterisks. The base residue thought to be important in catalysis is marked by an arrow. Sequence names other than NAALAD-ases (SEQ ID NOS 56–59 respectively in order of appearance) correspond to sequence accession numbers in Swiss-Prot and SPTREMBL; Ape 3 yeast (SEQ ID NO: 52), *Saccharomyces cervisiae* aminopeptidase Y; P96152 (SEQ ID NO: 53), *Vibrio cholerae* aminopeptidase; Ampx vibpr (SEQ ID NO: 54), *Aeromonoas proteolyitca* aminopeptidase, Application strgr (SEQ ID NO: 55), *Streptomyces griseus* aminopeptidase. Putative residues involved in zinc binding are marked by asterisks. General base residue thought to be important in catalysis is marked by an arrow.

FIG. 9: is an illustration of time course of NAALAD-ase activity. Activity of membrane preparations from COS cells transiently transfected with either NAALAD-ase I (A) or NAALAD-ase L (B). Hydrolysis of 500 nM 3[H]-NAAG in 1 mM $ZnCl_2$, 50 mM Tris.HCL (pH 7.4) was assayed for 0, 15, 30 and 60 min at 37° C. in the presence (open circles) or absence (closed circles) of 30 µM quisqualate. Reactions were terminated with 250 mM ice cold sodium phosphate and released 3[H]-glutamate measured. (C) Inhibition of NAALAD-ase I (open circles) and NAALAD-ase II (closed circles) activity by increasing concentrations of quisqualic acid expressed as % of control (activity in the absence of any inhibitor).

FIG. 10: is an illustration of NAALAD-ase activity determinations using SPA beads. (A) 10 µg of protein from LNCaP cell membrane preparations was used per reaction to develop a high throughput assay NAALAD-ase assay. Hydrolysis of 40 nM 3[H]-NAAG in 1 mM $ZnCl_2$, 50 mM Tris-HCL (pH 7.4) was measured at 25° C. for different incubation times in a 100 µl reaction volume. Reactions were terminated by the addition of 100 µl glycine buffer (pH 3.0) and naked YS-SPA beads. (C) Inhibition of NAALAD-ase I (open circles) or LNCaP membrane NAALAD-ase (closed circles) activity by increasing concentrations of quisqualic acid expressed as a % of control (activity in the absence of any inhibitor).

FIG. 11: is an illustration of chromosomal localisation of human NAALAD-ases. Diagrams of FISH mapping results for NAALAD-ase I (A), L (C) II (E) and IV (G). In each diagram dots represent the double FISH signals detected on identified chromosomes. Examples of FISH mapping of NAALAD-ase I (B), L (D), II (F) and IV (:H). Left panels show the FISH signals on the identified chromosome marked by a white arrow, right panels show the same mitotic Figure stained with DAI to identify the chromosome.

FIG. 12: is an illustration of northern blot analysis of NAALAD-ase II and IV expression. Human multiple tissue Northern blots (Klondike) containing 2 µg per lane of poly (A)+ RNA were hybridised with a $^{32}$p-labelled NAALAD-ase II (A) or IV (B) probes at 68° C. and washed at high stringency (final washes at 50° C. with 1/10 dilution of SSC/0.1% SDS). Autoradiographic exposure was done after 3 to 7 days at −70° C. with two intensifying screens. Molecular mass markers are indicated in bp on the left hand side of each autoradiogram.

FIG. 13: is an illustration of RT-PCR analysis of NAALAD-ase expression in different tissues. PCR amplifications with primers specific for human NAALAD-ase I (A), L (B), II (C) and IV (D) or GAPDH (E) were performed on normalised human MTC cDNAs™ for 25, 30 and 35 cycles. Images from ethidium bromide stained 1.5% agarose gels were captured using an EagleEye system and EagleSight software (Stratagene). Position control amplifications were performed using the appropriate NAALAD-ase DNA construct. Negative control amplifications contained reaction mix, enzyme and no DNA template. Positive and negative control reactions were performed for 35 cycles. Arrows highlight a specific size in bp as determined using a 100 bp ladder.

FIG. 14: is an illustration of RT-PCT analysis of NAALAD-ase expression in brain areas. PCR amplifications for 25, 30 and 35 cycles, with primers specific for human NAALAD-ase I (A), L (B), II (C) and IV (D) or GAPDH (E) were performed on normalised human cDNAs prepared from dissected brain areas. Images from ethidium bromide stained 11.5% agarose gels were captured using an EagleEye system and EagleSight software (Stratagene). Results from 30 and 35 cycles of amplification are shown. Positive control amplifications were performed using the appropriate NAALAD-ase DNA construct. Negative control amplifications contained reaction mix and enzyme with no DNA template. All control reactions were performed for 35 cycles. Arrows highlight a specific size in bp as determined from the 100 bp ladder.

FIG. 15: is an illustration of RT-PCR analysis of NAALAD-ase expression in prostate tumour cells. PCR amplifications with primers specific for human NAALAD-ase I (A), L (B), II (C) and IV (D) or GAPDH (E) were performed on normalised cDNAs prepared from cell lines derived from prostate tumours or on prostate tumour. Images from ethidium bromide stained 1.5% agarose gels were captured using an EagleEye stem and EagleSight software (Stratagene). Results from 25, 30 and 35 cycles of amplification were shown. Positive control amplifications were performed using the appropriate NAALAD-ase DNA construct. Negative control amplifications contained reaction mix and enzyme with no DNA template. All control reactions were performed for 35 cycles. Table 1.

Native Taq polymerase and PCR buffer with $MgCl_2$, the Expand™ long template PCR system, ampicillin, IPTG (isopropyl-β-D-thiogalactoside), X-gal (5-bromo-4-chloro-3-indolyl-β-D-galactopyranoside) and all restriction enzymes used were from Boehringer Mannheim (Mannheim, Germany). Super Taq polymerase was from HT Biotechnology (Cambridge, UK). 10 mM dNTP mix was purchased from Life Technologies (Gaithersburg, Md., USA). The original TA cloning kit and the expression vector pcDNA-3 were purchased from Invitrogen BV (Leek, The Netherlands). The Qiagen plasmid mini- and maxi- DNA purification kits, the Qiaquick gel extraction kit and the Qiaquick PCR purification kit were purchased from Qiagen GmbH (Düsseldorf, Germany). Marathon™ Ready cDNA kits, MTN cDNA panels and MTN Northern blots were obtained from Clontech Laboratories (Palo Alto, Calif., USA). The QuickChange™ Site-Directed Muatagenesis Kit was purchased from Stratagene GmbH (Heidelberg, Germany). All PCR reactions were performed in a GeneAmp PCR system 9600 cycler (Perkin Elmer, Foster City, Calif., USA). LB (Luria-Bertani) medium consists of 10 g/l of tryptone, 5 g/l of yeast extract and 10 g/l of NaCl. 2× YT/ampicillin plates consist of 16 g/l of tryptone, 10 g/l of yeast extract, 5 g/l of NaCl, 15 g/l of agar and 100 mg/l of ampicillin.

Expressed Sequence Tag Clones.

Clone numbers 4190746, 1547649, 3448872, 3608639, 2615389 and 1333965 were ordered from the LifeSeq™ expressed sequence tag (EST) database (Incyte Pharmaceuticals Inc., Palo alto, CA, USA). Samples were delivered as transformed bacterial clones.

Oligonucleotide synthesis for PCR and DNA sequencing. All oligonucleotide primers were synthesised by the β-cyanoethylphosphoramidite chemical method on a PerSeptive Biosystems (Framingham, Mass., USA) Expedite MOSS Synthesiser or ordered from Eurogentec (Seraing, Belgium). Insert-specific sequencing primers (15- and 16- Mars) were designed manually. DNA was prepared on Qiagen-tip-20 or -100 anion exchange or Qiaquick spin columns (Qiagen GmbH, Düsseldorf, Germany) and recovered from the columns in 30 µl TE-buffer (10 mM Tris.HCL, 1 mM EDTA (sodium salt), pH 8.0). Sequencing reactions were done on both strands using the ABI prism BigDye Terminator Cycle sequencing kit and were run on an Applied Biosystems 377XL sequencer (Perkin Elmer; ABI Division, Foster City, Calif., USA). The Sequencher™ software was used for sequence assembly and manual editing (GeneCodes, Ann Arbor, Mich., USA).

Cloning and sequence analysis of NAALAD-ase I, L, II and IV.

Sequence similarity searching for NAALAD-ase like molecules. Using the complete human (Accession no.M99487), rat (Accession no. RNU75973) and mouse (Accession no. AF026380) NAALAD-ase I protein sequences, the complete rat NAALAD-ase L (GenBank™ Accession no AF009921) protein sequence and a partial human NAALAD-ase L protein sequence (GenBank™ Accession no. AF010141) as query sequences, a BLAST (Basic Local Alignment Search Tool; Altschul et al., 1990) search was performed on the WashU Merck expressed sequence tag (EST) database and on a proprietary LifeSeq™ human EST database (Incyte Pharmaceuticals Inc, Palo Alto, Calif., USA). Six EST clones with homology to NAALAD-ase I and L were ordered from the Incyte Pharmaceuticals.

Plasmid DNA preparation and sequencing from Incyte clones. Each Incyte bacterial clone was grown overnight at 37° C. in 100 ml LB-medium supplemented with 100 µg/ml of ampicillin. Plasmid DNA was prepared using a Qiagen plasmid midi or maxi kit according to the manufacturer's instructions. The DNA inserts of all clones were completely sequenced on both strands. Clone 4190746 contained sequences corresponding to human NAALAD-ase L and also included likely intronic sequences, clones 133965, 1547649, 3448872, 3608639 contained overlapping DNA sequences coding for a novel protein with some similarity to other NAALAD-ases and clone 2615389 contained DNA sequences corresponding to yet another novel protein with some similarity to previously identified NAALAD-ases. The novel protein sequences derived from these clones were termed NAALAD-ase II and NAALAD-ase IV respectively.

Cloning of NAALAD-ase I by PCR. Sequence data from human NAALAD-ase I (Accession no. M99487) was used to design primers to amplify the complete coding sequence of NAALAD-ase I by PCR. Primers used were NAALD1S2 (BamHI)=5'-CCC GGA TCC GAG ATG TGG ATT CTC CTT CAC GAA AC-3' (SEQ ID NO: 1) and NAALDIAS2 (XhoI)=5'-CCC CTC GAG TTA GGC TAC TTC ACT CAA AGT CTC TGC-3' (SEQ ID NO: 2) (restriction sites to be introduced are underlined). PCR amplification was performed using Human Marathon-Ready™ cDNA from prostate in a total reaction volume of 50 µL, containing 1× Expand LongTemplate™ PCR buffer 2, 0.2 mM of each dNTP, 0.2 µM each of oligonucleotide primers NAALD1S1 (BamHI) and NAALD1AS1 (XhoI), 1 µL of Marathon-Ready™ cDNA and 2.5 U of Expand Long Template PCR mix. Samples were pre-heated at 94° C. for 5 min before addition of enzyme. Cycling was for 45 s at 94° C., 1 min at 55° C. and 1 min 48 s at 68° C. for 30 cycles, with a final step of 7 min at 72° C. PCR products were analysed on a 1% agarose gel (wt/vol) in 1× TAE buffer (40 mM Tris-acetate, 1 mM EDTA (sodium salt), pH 8.3) and the most prominent DNA band was excised from the gel and purified with the Qiaquick gel extraction kit (Qiagen GmbH, Dusseldorf, Germany).

The resulting 2303 base pair (bp) fragment was cloned into the plasmid vector pCR2.1 using the original TA cloning kit according to the manufacturer's instructions. Approximately 20 ng of purified fragment was ligated to 50 ng of pCR2.1 plasmid DNA with 4 U T4 DNA ligase in a total volume of 10 µl.

Ligations were incubated overnight at 14° C. 2 µl of the ligation reaction was transformed into TOP10F' competent cells using heat-shock transformation and plated on 2× YT/ampicillin plates supplemented with IPTG and X-gal for blue-white screening. Colony screening was performed on 10 white colonies, from which plasmid DNA was prepared using the Qiagen plasmid mini DNA purification kit, and then digested with BAMHI and XHoI. Four clones containing an insert of the appropriate size were sequenced fully. All the clones had at least one mis-sense PCR error. Clone 10.0 with a single PCR error at position 1183 was used as the template for a site directed mutagenesis (SDM) reaction using the QuickChange™ SDM Kit. Reactions were carried out according to the manufacturer's instructions. Primers designed for the amplification reactions were NAALD1-SDM-S1=5'-CCC TCA GAG TGG AGC AGC TGT TGT TCA TGA AAT TGT GAG G-3' (SEQ ID NO: 3) and NAALD1-SDM-AS1=5'-CCT CAC AAT TTC ATG AAC AAC AGC TGC TCC ACT CTG AGG G-3' (SEQ ID NO: 4). Three white clones from the SDM transformations were screened. Plasmid DNA was prepared using the Qiagen plasmid mini DNA purification kit, digested with BamHI and XhoI and sequenced around the mutation site. A single clone (cl. 2.0) was sequenced fully on both strands to confirm the complete correct NAALAD-ase I sequence.

Cloning of NAALAD-ase L by PCR and 5' rapid amplification of cDNA ends (RACE) PCR. Sequence data from partial human NAALAD-ase L (GenBank Accession no. AF10141) was used to design primers to amplify the 3' end of NAALAD-ase L by PCR. Primers used were NAALD2S1=5'-GTT CTT CAA CAA GCT GCA GGA GCG-3' (SEQ ID NO: 5) and NAALD2AS1(XhoI)=5'-CCC CTC GAG CCG GAG TAA AGG GAG GGC TGA AG-3' (SEQ ID NO: 6). HumanMarathon-Ready™ cDNA from brain, fetal brain, prostate, small intestine, colon were used in the amplification reactions. First round PCR amplification was performed in a total reaction volume of 50 µl containing 1× Expand High Fidelity™ PCR buffer, 0.2 mM of each dNTP, 0.2 µM each of oligonucleotide primers NAALD2S1 and NAALD2AS1, 1 µl of Marathon-Ready™ cDNA and 2.5 U of Expand High Fidelity PCR mix. Samples were preheated at 94° C. for 5 min before addition of the enzyme. Cycling was for 45 s at 94° C., 1 min at 58° C. and 1 min at 72° C. for 30 cycles, with a final step of 7 min at 72° C. PCR products were analysed on a 1% agarose gel in 1× TAE buffer. Second round PCR amplification was performed with nested primers NAALD2S2=5'-GGC GAC CTG AGC ATC TAC GAC AAC-3' (SEQ ID NO: 7) and NAALD2AS2 (XhoI)=5'-CCC CTC GAG TCC CCT CAG AGG TCA GCC ACA G-3' (SEQ ID NO: 8). 1 µl of the first round amplification reaction in a total volume of 50 µl containing 1× Expand High Fidelity™ PCR buffer, 0.2 mM of each dNTP, 0.2 µM each of oligonucleotide primers NAALD2S2 and NAALD2AS2 and 2.5 U of Expand High Fidelity PCR mix. Samples were preheated at 94° C. for 5 min before addition of the enzyme. Cycling was for 45 s at 94° C., 1 min at 57° C. and 1 min at 72° C. for 30 cycles, with a final step of 7 min at 72° C. PCR products were analysed on a 1% agarose gel in 1× TAE buffer and the most prominent DNA bands were excised from the gel and purified with the Qiaquick gel extraction kit. The resulting fragments 600–800 bp were cloned into CR2.1 as described previously. Ligations were incubated overnight at 14° C. and transformed into TOP10F' competent cells and plated on 2× YT/ampicillin plates supplemented with IPTG and X-gal for blue-white screening. Colony screening was performed on five white colonies from each transformation. Plasmid DNA was prepared from these colonies using the Qiagen plasmid mini DNA purification kit and then digested with EcoRI. Plasmids containing inserts of the appropriate size were end sequenced using vector primers and then the full sequencing on both strands of putative NAALAD-ase L clones was performed. Clone 6.9 derived from small intestine extended to the translation termination codon.

To obtain unknown 5' coding sequence for human NAALADase L, two anti-sense primers were designed for 5' rapid amplification of cDNA ends (5'RACE). The primers were NAALD2AS3=5'-GCC AGC ACC CAG AGA ACC CAA G-3' (SEQ ID NO: 9) and NAALD2AS4=5'-GCT GCG GTT GAA GTA CCG GAT C-3' (SEQ ID NO: 10). HumanMarathon-Ready cDNA from brain, fetal brain, prostate, small intestine and colon were used for the 5' RACE according to the manufacturer's instructions. The Marathon-Ready cDNA was prepared using oligo-dT priming and a Marathon cDNA adaptor (including two different adaptor-primer annealing sites) ligated to the 5' end of the cDNA. AdaptorprimerAP1 (5'-CCA TCC TAA TAC GAC TCA CTA TAG GGC3') (SEQ ID NO: 11) and nested adaptor-primer AP2 (5'-ACT CAC TAT AGG GCT CGA GCG GC-3') (SEQ ID NO: 12) were included in the kit.

First round PCR amplification was performed in a total reaction volume of 50 µl containing 1× Expand High Fidelity™ PCR buffer, 0.2 mM of each dNTP, 0.2 µM each of oligonucleotide primers AP1 and NAALD2AS3, 5 µl of Marathon-Ready™ cDNA and 2.5 U of Expand High Fidelity PCR mix. Samples were preheated at 94° C. for 5 min before addition of the enzyme. Cycling was for 30 s at 94° C., 30 s at 58° C. and 2 min at 72° C. for 30 cycles, with a final step of 7 min at 72° C. PCR products were analysed on a 1% agarose gel in 1× TAE buffer. Second round 5' RACE was performed using 1 µl of the first round amplification reaction in a total volume of 50 µl containing 1× Expand High Fidelity™ PCR buffer, 0.2 mM of each dNTP, 0.2 µM each of oligonucleotide primers AP2 and NAALD2AS4 and 2.5 U of Expand High Fidelity PCR mix. Samples were preheated at 94° C. for min before addition of the enzyme. Cycling was for s at 94° C., 30 s at 57° C. and 1 min at 72° C. for 30 cycles, with a final step of 7 min at 72° C. PCR products were excised from the gel and cloned into the vector pCR2.1 as described earlier. Colony screening by PCR was performed on 60 white colonies in 45 41 PCR mix containing 1× PCR buffer with M9Cl2, 0.2 mM dNTP, 0.5 µM each of vector primer M13FOR (5'-TGT AAA ACG ACG GCC AGT-3') (SEQ ID NO: 13) and M13REV (51-CAG GAA ACA GCT ATG ACC-3') (SEQ ID NO: 14) and 0.35 U of super Taq DNA polymerase.

Colonies were picked from the plates, inoculated into 100 µLB medium supplemented with 100 µg/ml of ampicillin and incubated for 1 hr at 37° C. 5 µl of the incubated culture was then added to 45 µl PCR mix. PCR was performed for 30 cycles (45 s at 95° C., 1 min at 48° C. and 50 s at 72° C.). 20 µl of the PCR reactions was analyzed on 1% agarose gel in 1× TAE buffer. Clones containing inserts were grown overnight in 3 ml LB medium supplemented with 100 µg/ml of ampicillin and plasmid DNA was prepared using the Qiagen plasmid mini DNA purification kit. From the 51 clones sequenced one clone 4.10 contained 258 bp of sequence 5' to NAALD2AS4 of which 70 bp were novel.

The 5' RACE clone (cl. 4.10) and 3' PCR clone (cl. 6.9) were both digested with BamHI. The digested material was run on 1% agarose gel in 1× TAE buffer. Two bands were excised, a 336 bp band from cl. 4.10 containing all additional 5' RACE DNA sequences and a ~4700 bp fragment containing the remaining 3' NAALAD-ase L and vector sequence from cl. 6.9. The gel slices were purified with the Qiaquick gel extraction kit. The larger of the two fragments was dephosphorylated with 1.5 U calf of intestinal alkaline phosphatase for 1 hr at 37° C. and then heat inactivated for 20 min at 75° C., in order to prevent the self ligation of the fragment with itself. Ligations were performed as described previously and 2 µl of the reaction mixture transformed into 35 µl DH10b electrocompetent cells by electroporation (single pulse; 2500V, 25 µF 201 W, 5 ms). The electroporated sample was added to 1 ml SOC media and incubated for 1 hr at 37° C. before 100 µl of the culture was plated on to 2× YT/ampicillin plates.

Colonies were picked the following day, plasmid DNA prepared and tested by restriction digest. A single clone (cl. 2.0) was fully sequenced on both strands and found to contain the complete 3' coding sequence and the additional sequence from the first 5' RACE reactions. To obtain additional 5' coding sequence for the human NAALAD-ase L, two new anti-sense primers were synthesized corresponding to sequences from Incyte clone number 4190746. Primers used were NAALD2ASS=5'-CTG CAG CTT GTT GAA CTC TTC TGT G-3' (SEQ ID NO: 15) and NAALD2AS6=5' CAA ACA CGA TTG ATC TGC GAG GAC-3' (SEQ ID NO: 16). Human Marathon-Ready™ cDNA from brain, fetal brain, prostate, small intestine, colon and heart were used for the 5' rapid amplification of cDNA ends (5' RACE) according to the manufacturer's instructions.

First round PCR amplification was performed in a total reaction volume of 50 µl containing 1× Expand High Fidelity™ PCR buffer, 0.2 mM of each dNTP, 0.2 µM each of oligonucleotide primers AP1 and NAALD2AS5, 5 µl of Marathon-Ready™ cDNA and 2.5 U of Expand High Fidelity PCR mix. Samples were preheated at 94° C. for 5 min before addition of the enzyme. Cycling was for 30 s at 94° C., 30 s at 58° C. and 1 min at 72° C. for 30 cycles, with a final step of 7 min at 72° C. PCR products were anlysed on a 1% agarose gel in 1× TAE buffer (40 mM Tris-acetate, 1 mM EDTA, pH 8.3). Second round PCR amplification was performed using 1 µl of the first round amplification reaction in a total volume of 50 MG containing 1× Expand High Fidelity™ PCR buffer, 0.2 mM of each dNTP, 0.2 µM each of oligonucleotide primers AP2 and NAALD2AS6 and 2.5 U of Expand High Fidelity PCR mix. Samples were preheated at 94° C. for 5 min before addition of the enzyme. Cycling was for 30 s at 94° C. and 1 min at 72° C. PCR products were analysed on a 1% agarose gel in 1× TAE buffer and the 8 most prominent DNA bands were excised from the gel and purified with the Qiaquick gel extraction kit. The resulting fragments (400–1300 bp) were cloned into the plasmid vector pCR2.1 using the original TA cloning kit. Ligations and transformations were performed as described earlier before plating on 2× YT/ampicillin plates supplemented with IPTG and X-gel for blue-white screening. Colony screening was performed on five white colonies from each transformation. Plasmid DNA was prepared from these colonies using the Qiagen plasmid mini DNA kit and digested with EcoRI. Plasmids containing inserts of the appropriate size were end sequenced using vector primers and then the full sequence of putative NAALAD-ase L clones was determined using primer walking. The DNA sequence of five clones, from a small intestine cDNA, extended the coding sequence for NAALAD-ase L in the 5' direction beyond the putative translation start codon and included part of the 5' untranslated region. One of these clones one (cl. 2.2) was used for further experiments.

To construct a full length NAALAD-ase L clone, two new primer sets were designed to introduce a unique restriction site (Mun I) into the DNA sequence of NAALAD-ase L without resulting in a change in amino acid sequence or frame shift in the open reading frame (ORF). The first primer set was NAALD2S3 (EcoRV)=51-CGG ATA TCC GCA GGA TGC AGT GGA CGA AG-3' (SEQ ID NO: 17) and NAALD2AS8 (Mun I)-5'-CAA ACA CAA TTG ATC TGC GAG GAC GC-3' (SEQ ID NO: 18) and the second primer set was NAALD2S8 (Mun I)'-GCG TCC TCG CAG ATC AAT TGT GTT TG-3' (SEQ ID NO: 19) and NAALD2AS1 (XhoI). PCR amplification was performed on 1 µL cl. 2.0 plasmid DNA with primers NAALD2S3 (EcoRV) and NAALD2AS8 (MunI) or on 1 µl cl. 2.2 plasmid DNA with primers NAALD2S8 (MunI) and NAALD2AS1 (XhoI).

Total reaction volumes were as previously described. Samples were preheated at 94° C. for 5 min before addition of the Expand High Fidelity enzyme. Cycling was for 45 s at 95° C., 1 min at 57° C. and 1 min at 72° C. for 30 cycles, with a final step of 7 min at 72° C. PCR products were analysed on a 1% agarose gel in 1× TAE buffer and TA cloned into pCR2.1 as previously described.

Splice Variant Analysis of NAALAD-ase L.

In PCR reactions using NAALAD-ase L specific primers, a number of amplified PCR products were observed of unexpected size. These PCR reactions were repeated using a number of different cDNAs and bands were excised and purified prior to original TA cloning, as described previously. Plasmid DNA was prepared from these clones and inserts were fully sequenced on both strands in order to identify possible splice variants.

Cloning of NAALAD-ase II by PCR and 5' Rapid Amplification of cDNA Ends (RACE) PCR.

Sequencing results from Incyte clone 3608639 suggested that this clone contained DNA sequence spanning the complete coding sequence, 2220 bp in size, of a putative NAALAD-ase like molecule (NAALAD-ase II) that had similar sequence to NAALAD-ase I and L. To confirm that there was no possible initiation codon upstream of the initiation codon already determined 5' RACE PCR was performed. Two anti-sense primers were designed for 5' RACE based on the sequence derived from the clone 3608639, NAALD3ASI=5'-CTT TGA TGA TAG CGC ACA GAA GTG G-3' (SEQ ID NO: 20) and NAALD3AS2=5' GGA AAG ATG CCA GCG CAG GAC 03' (SEQ ID NO: 21). Human Marathon-Ready™ cDNA from brain, foetal brain, prostate, small intestine and colon were used for the 5' RACE according to the manufacturer's instructions. First round PCR amplification was performed in a total reaction volume of 50 µl containing 1× Expand High Fidelity™ PCR buffer, 0.2 mM of each dNTP, 02 µM each of oligonucleotide primers AP1 and NAALD3AS1, 5 µl of Marathon-Ready™ cDNA and 2.5 U of Expand High Fidelity PCR mix. Samples were preheated at 94° C. for 5 min before addition of the enzyme. Cycling was for 30 s at 94° C., 30 s at 58° C. and 2 min at 72° C. for 30 cycles, with a final step of 7 min at 72° C. Second round 5' PACE was performed using 1 µl of the first round amplification reaction in a total volume of 50 µl containing 1× Expand High Fidelity™ PCR buffer, 0.2 mM of each dNTP, 0.2 µM of each oligonucleotide primers AP2 and NAALD3AS2 and 2.5 U of Expand-High Fidelity PCR mix. Samples were preheated at 94° C. for 5 min before addition of the enzyme. Cycling was for 30 s at 94° C., 30 s at 57° C. and 1 min at 72° C. for 30 cycles, with a final step of 7 min at 72° C. PCR products were analysed on a 1% agarose gel in 1× TAE buffer and the most prominent DNA bands were excised from the gel and purified with the Qiaquick gel extraction kit. The resulting fragments (250–600 bp) were cloned into the plasmid pCR2.1 as described previously. 32 white colonies were grown overnight in 3 ml LB medium supplemented with 100 µg/ml of ampicillin and plasmid DNA was prepared using the Qiagen plasmid mini DNA purification kit. No upstream initiation codon was identified from any of the 32 clones analysed.

Cloning of NAALAD-ase IV by PCR.

Sequencing results from Incyte clone 2615389 revealed that this clone contained partial coding sequence and 3' UTR, of another putative NAALAD-ase like molecule (NAALAD-ase IV) that was related in sequence to NAALAD-ase I, L and II. The DNA sequence obtained was used in a BLAST search on the Incyte LifeSeq™ EST database. One contig (2519841) was assembled from 150 overlapping Incyte EST sequences that spanned 1881 bp and contained a coding region of 1419 bp. The sequence data from human NAALAD-ase IV contig 2519841 was used to design primers to amplify the complete coding sequence of by PCR. Primers used were NAALD4SP2=51-CGT CAG AGC CGC CCT ATC AGA TTA TC-3' (SEQ ID NO: 22) and NAALD4AP4'-GAG GAG TTT TCC AAA GTT GCA GAC CC-3' (SEQ ID NO: 23). PCR amplification was performed using a human hippocampal cDNA in a total reaction volume of 50 µl, containing 1× Expand High Fiedlity™ PCR buffer, 0.2 mM of each dNTP, 0.2 µM each of oligonucleotide primers NAALD4SP2 and NAALD4APA4, 1 µl of cDNA and 2.5 U of Expand High Fidelity™ PCR mix. Samples were pre-heated at 95° C. for 5 min before addition of enzyme. Cycling was for 45 s at 94° C., 1 min at 58° C. and 35 s at 72° C. for 30 cycles, with a final step of 7 min at 72° C. PCR products were analysed on a 1% agarose gel in 1× TAE buffer and the most prominent DNA band was excised from the gel and purified with the Qiaquick gel extraction kit. The resulting 1544 bp DNA fragment was sub-cloned into the plasmid vector pCR2.1-TOPO using the TA TOPO cloning it according to the manufacturer's instructions. Approximately 10 ng of purified fragment was ligated to 10 ng of pCR2.1-TOPO plasmid DNA. Ligations were incubated for 5 min at 25° C. Transformations into TOPIOF1 competent cells and colony screening was performed as previously described. Three clones containing an insert of the correct size were sequenced fully and two clones were found to contain no PCR errors (cl. 28.0 and cl. 1.0).

Activity Determinations of NAALAD-ases Transiently Expressed in COS Cells.

Sub-cloning of NAALAD-ases into expression vectors. NAALAD-ase I, L, II and IV clones were each sub-cloned into the cytomegalovirus (CMV) promoter-based plasmid vector pcDNA-3. NAALAD-ase I/pCR2.1 (cl.2.0) was digested with BamHI/XhoI to excise the complete NAALAD-ase I sequence. NAALAD-ase L-5'/pCR2.1 (cl.2.0) was digested with EcoRV/MunI and NAALAD-ase II-3'/pCR2.1 (cl.2.2) was digested with MunI/XhoI to excise the two halves of complete NAALAD-ase L sequence. NAALAD-ase II/pINCYTE was digested with EcoRI to excise the complete NAALAD-ase II sequence. NAALAD-ase IV/pCR2.1 (cl.28.0) was digested with HindIII/XbaI to excise the complete NAALAD-ase IV sequence. Fragments were gel-purified and sub-cloned into dephosphorylated pcDNA3 that had been previously digested with the appropriate restriction enzymes. The resulting expression constructs were verified by complete sequence analysis as described earlier.

Transient Transfection into COS Cells.

COS cells were maintained in complete medium (DMEM supplemented with 10% foetal calf serum, 1× non-essential amino acids and a 1× strptamycin/penicillin/glutamine mix). Prior to transfection cells were washed twice with PBS, $Ca^{+2}/Mg^{2+}$ free pre-warmed to 37° C. and dissociated from culture plates by addition of a trypsin/EDTA solution for 1–2 minutes. Cells were collected after a 10 min spin at 1600 rpm and re-suspended in 1–2 ml of equilibrated (5% $CO_2$/95% air) pre-warmed medium. The cell titre was determined in a Coulter counter and cells were seeded in 6 well plates at a density of 15000 cells/cm$^2$ and allowed to reach approximately 80% confluence (~2 days growth). For each transfection 6 µl FuGENE6 (Boehringer Mannheim, Germany) was added to 96 µl serum free medium and incubated for 5 minutes at 20° C. This preparation was added to a second tube containing 1 µg of NAALAD-ase/pcDNA3 DNA, mixed gently and allowed to stand for 15 minutes at room temperature. The DNA/FuGENE6/serum-free medium mix was pipetted into a well containing 2 ml fresh complete medium. Cells were incubated for 72 hrs in a 37° C. incubator before collection.

Determination of Biological Activity of NAALAD-ase Homologues.

NAALAD-ase activity was quantified by determination of the extent of hydrolysis of N-acetyl-L-aspartyl-L-(3,4-[$^3$H])-glutamate as previously described (Blakeley et al., 1988). Transfected COS cell pellets were incubated with 50 mM Tris-HCl (pH7.4)/0.1% Triton X-100 and vortexed. Homogenates were put through at least one freeze/thaw cycle in liquid $N_2$ before being used for assay. All assays were formed in a total volume of 200 µl containing 50 mM Tris-HCl (pH 7.4), 1 mM $Zn^{2+}Cl_2$, 500 nM N-acetyl-L-aspartyl-L-(3,4-3[H])-glutamate ([$^3$H]-NAAG) and 10–200 µg membrane protein in the presence or absence of 3 µM quisqualate/1% DMSO (vol/vol). Assays were initiated by the addition of the membrane homogenates to the assay mixture, preincubated at 37° C. The assay mixture was vortexed and incubated at 37° C. for various time points. Reactions were terminated by addition of 200 µl ice cold 250 mM potassium phosphate and placing the reaction tubes in ice water. After a 5 min centrifugation step at 14000 rpm, the assay samples were loaded onto 4 cm anion exchange mini-columns (Bio-Rad Ag1-X 8) that had been pre-washed with MilliQ water. Columns were rinsed twice with 2 ml MilliQ water, and then twice with 2 ml of 0.5 M formic acid to selectively elute the [3H]-glutamate. The remaining substrate could be eluted with 7.5M formic acid. Assay eluates were diluated with scintillation cocktail (16 ml Ultima Gold XR) and counted in a scintillation counter (Packard). Blanks (not exposed to membranes) were always subtracted. Inhibition curves were performed under similar conditions with concentrations of quisqualate (QA) ranging up to 300 µM. Reactions were followed for 30 min for NAALAD-ase I and for 60 min for NAALAD-ase L and II prior to termination of the reaction.

SPA Development for High Throughput Screening.

NAALAD-ase assays were performed at 37° C. or 25° C. for 10 min in the presence of 50 mM Tris-HCl, pH 7.4, containing 1 mM $ZnCl_2$. Each assay was performed in a 100 µl reaction volume containing 40 nM 3[H]-NAAG, 50 mM Tris-HCl (pH 7.4), 1 mM $Zn^{2+}C_2$ and either 10 µg of recombinant NAALAD-ase I or LNCaP cell membrane preparations. Reactions were terminated by addition of 100 µl glycine buffer (pH 3.0) and 1 mg naked YS-SPA beads. After allowing the beds to settle for 30 min, the assay mixture was counted in a microtiterplate scintillation counter.

Chromosomal Localisation of NAALAD-ases by FISH.

Chromosomal mapping studies were carried out by Sidney Biotech Inc (North York, Ontario Canada) using fluorescent in situ hybridisation (FISH) analysis.

Slide preparation. Lymphocytes isolated from human blood were cultured in α-minimal essential medium (MEM) supplemeneted with 10% foetal calf serum and phytohaemagglutinin at 37° C. for 68–72 h. The lymphocyte cultures were treated with BrdU (0.18 mg/ml, Sigma Chemical Company, St. Louis, Mo., USA) to synchronise the cell population. The synchronised cells were washed three times with serum-free medium to release the block and re-cultured at 37° C. for 6 h in α-MEM with thymidine (2.5 µg/ml, Sigma). Cells were harvested and slides were prepared using standard procedures including hypotonic treatment, fixation and air-drying.

FISH detection: Probes (NAALAD-aseI/pCR2.1 (cl. 2.0) cut with BamHI/XhoI; NAALAD-aseL/pCR2.1 (cl.2.0) cut with XhoI; NAALAD-aseII/pcDNA3 (cl. 3.0) cut with HindIII/XbaI; NAALAD-aseIV/pCR2.1 (cl. 28.0) cut with HindIII/XbaI; were biotinylated with dATP for 1 h at 150 C using the BioNick labelling system (Life Technologies, Gaithersburg, Md., USA). The procedure for FISH detection was performed as previously described (Heng et al, 1992; Heng & Tsui, 1993). Slides were baked at 55° C. for 1 h. After Rnase treatment, the slides were denatured in 70% formamide in 2×SSC (20×SSC being 3 M NaCl, 0.3 M sodium citrate, pH 7.0) for 2 min at 70° C. followed by dehydration with ethanol. Probes were denatured at 75 C for 5 min in a hybridisation mix consisting of 50% formamide and 10% dextran sulphate. Probes were then loaded on the denatured chromosomal slides. After overnight hybridisation, slides were washed and detected. FISH signals and the DAPI-banding pattern were recorded separately by taking photographs, and the assignment of the FISH mapping data with chromosomal bands was achieved by superimposing FISH signals with DAPI banded chromosomes.

Tissue Distribution of NAALAD-ases.

Northern Blot Analysis for NAALAD-ase II and IV. Human MTN Northern blots containing 2 μg of poly (A)+ RNA derived from non-neuronal tissues were hybridised in ExpressHyb™ hybridisation solution for 2 to 3 h at 68° C. according to the manufacturer's instructions. A 546 bp NAALAD-ase II fragment was isolated from NAALAD-ase II/pcDNA3 (cl. 3.0) following digestion with EcoRI and BglII and a NAALAD-ase IV 526 bp fragment was isolated from NAALAD-ase IV/pCR2.1-TOPO (cl. 28.0) following digestion with PstI. Radiolabelled probes were generated with these DNA fragments using a Rapid Multiprime Labelling kit and [$^{32}$P]—dCTP as label. Following removal of unincorporated label using a Micospin S-200 HR column (Pharamcia), 50 μl of hot denatured probe in 6 ml ExpressHyb™ hybridisation solution was incubated in a rotating shaker at 68 C overnight. Washes were 4×15 min RT in 2×SSC/0.05% SDS, 1×20 min wash at 50 C in 0.1×SSC/0.1% SDS and 2×20 min at 55 C in 0.1×SSC/0.1% SDS and 2×20 min. Blots were wrapped in cling flim, without drying and exposed to X-omat AR Scientific Imaging Flim (Kodak Scientific Imaging Systems, Cambridge, UK) for 2 to 4 days at −70° C. with two intensifying screens.

Gene Expression of NAALAD-ase I, L, II and IV by RT-PCR Analysis.

Oligonucleotide primers designed for the specific amplification of a PCR fragment for each NAALD-ase; NAALAD-ase I primers were NAALAD1S3 5'-GGG AAA CAA ACA AAT TCA GCG GC-3' (SEQ ID NO: 24) and NAALD1AS3 51 GTC AAA GTC CTG GAG TCT CTC ACT GM C-3' (SEQ ID NO: 25) yielding a 341 bp product, NAALAD-ase L primers were NAALD2S7 51-GAC CGG AGC AAG ACT TCA GCC AG-3' (SEQ ID NO: 26) and NAALD2AS7 5'-GTG TTG ATA TGC GTT GGC CCA AG-3' (SEQ ID NO: 27) yielding a 330 bp product, NAALAD-ase II primers were NAALD3S4 51 CAC TAA GAA TAA GAA AAC AGA TAA GTA CAG C-3' (SEQ ID NO: 28) and NAALD3AS4 51-GAT CAA CTT GTA TAA GTC GTT TAT GAA AAT CTG-3' (SEQ ID NO: 29) yielding a 353 bp product and NAALAD-ase IV primers were NAALD4SI 5'-GCA GAA GAA CAA GGT GGA GTT GGT G-3' (SEQ ID NO: 30) and NAALD4ASI 5'-GCT TTG GAT CCA TGA CAG TCA TGG-3' (SEQ ID NO: 31) yielding a 336 bp product. Each primer set for each NAALAD-ase was tested for its ability to specifically amplify that NAALAD-ase and not to cross react in amplification reactions with the other three forms. PCR amplifications for human GAPDH were performed on the same cDNA samples as positive controls using GAPDH specific primers 5'-TGA AGG TCG GAG TCA ACG GAT TTG GT-3' (SEQ ID NO: 32) (sense primer) and 5'-CAT GTG GGC CAT GAG GTC CAC CAC-3' (SEQ ID NO: 33) (anti-sense primer), yielding a 1000 bp fragment. These primers sets were used for PCR amplifications on human multiple tissue cDNA (MTCTM) panels normalised to the mRNA expression levels of six different housekeeping genes. Human cDNAs from 15 brain regions were also prepared from mRNA and normalised to the mRNA expression levels of three different housekeeping genes, GAPDH, clathrin and actin. Brain area mRNA was prepared starting from carefully dissected tissue samples, using the Fast-TrackR 2.0 kit (Invitrogen BV, Netherlands) according to the manufacture's instructions. 1 μg of poly (A)+ RNA was reverse transcribed using oligo (dT) 15 as a primer and 50 U of Exapnd™ Reverse Transcriptase (Boehringer Mannheim, Germany) according to the manufacturer's instructions.

Finally, normalised cDNA was prepared in a similar manner from 3 transformed prostate tumour cell lines and a prostate tumour. PCR reactions with NAALAD-ase or GAPDH specific primers were performed on 2 or 5 μl of cDNA. PCR reactions were performed in a total volume of 50 μl in 1× Advantage PCR buffer, 0.2 mM dNTP and 0.5 μM of each PCR primer and 1 μl Advantage Taq polymerase mix (95° C.-30 sec, 68° C.-1 min 30 s for 35 cycles). Upon completion of 25 cycles the PCR machine was paused at 80 C, reaction tubes were removed and 15 μl were removed from each PCR tube. Tubes were then returned to the machine and the cycling method continued. Aliquots were removed in a similar manner after 30 and 35 cycles. Each sample taken was analysed by 1.0% agarose gel electrophoresis as previously described and images of the ethidium bromide stained gels were obtained using an Eagle Eye II Video system (Stratagene, La Jolla, Calif., USA).

Results

Molecular Cloning and Sequence Analysis of NAALAD-ase II, L and IV.

NAALAD-ase L; Similarity searching of the Incyte LifeSeq™ database with the human, rat and mouse NAALAD-ase I sequences and with rat and partial human NAALAD-ase L protein sequences yielded 13 EST sequences, some of which were overlapping, encoding for putatively novel protein sequences similar to NAALAD-ase I and L. DNA obtained from six of the most 5' clones were sequenced.

Incyte clone 4190746, from a cerebellar cDNA library contained sequences corresponding to NAALAD-ase L. However, since this clone also contained two segments of intronic sequence it was not suitable for further cloning experiments. PCR reactions were performed to amplify a PCR product containing the 3' half of the NAALAD-ase L coding region from a small intestine cDNA. To identify the remaining as yet unknown human 5' NAALAD-ase L sequence, 5' RACE PCR was performed on a number of cDNAs. Sequencing of the amplification products obtained from reactions using small intestine cDNA yielded a further 1344 bp fragment covering the complete coding sequence of NAALAD-ase L. The full cDNA sequence contained an open reading frame of 2223 bp encoding a protein of 740 amino acid residues with a calculated molecular mass of 80.6 kDa and an isoelectric point of 5.26 (FIG. 1). The putative ATG translation start codon is in a favourable context for translation initiation (Kozak, 1989) with no ATG codons detected upstream. Analysis of the human NAALAD-ase L ORF predicted a type II integral membrane protein containing a single hydrophobic membrane-spanning domain extending from amino acid residues 6–27, with lysine residues bordering either side of the potential membrane-spanning domain (determined by the method of Kyte-Doolittle, 1982). There are 7 potential N-glycosylation sites (N×S/T), indicated in FIG. 1. The predicted protein sequences of human NAALAD-ase L was compared to that of rat using the alignment program Genedoc. Human NAALAD-ase L sequence was 78% identical and 87% similar to rat NAALAD-ase L. The two protein sequences were aligned using the ClustalW alignment program (EMBL, Heidelberg, Germany; FIG. 2)

NAALAD-ase II; Incyte clones 1547649, 3448872, 3608639 and 1333965 contained sequences originating from the same gene that were similar to but not identical to NAALAD-ase I or L. Clone 3608639, from a lung carcinoma cDNA library, contained a 3110 bp DNA sequence, with a 2223 bp ORFcoding for a 740 amino acid residue protein, which we termed NAALAD-ase II (FIG. 4). Analysis of this open reading frame predicted a calculated molecular mass of 83.6 kDa and an isoelectric point of 8.53. The putative ATG translation start codon is in a favourable context for translation initation (Kozak, 1989) and no ATG codons were detected upstream. NAALAD-ase II was predicted to be a type II integral membrane protein containing a hydrophobic membrane spanning domain extending from amino acid residues 8–31 (determined by the method of Kyte and Doolittle, 1982). There are also 7 potential N-glycosylation sites (N×S/T) indicated in FIG. 4.

NAALAD-ase IV; Sequencing of Incyte clone 2615389, derived from a gall bladder cDNA library, identified sequences originating from a gene with some similarity to NAALAD-ase I and L. Homology searching in the Incyte EST database using this new sequence information identified a contig of over 150 overlapping EST sequences spanning 1884 bp and containing an ORF of 1419 bp, plus 5' and 3' UTRs. Translation of the ORF predicted a 472 amino acid protein with calculated molecular mass of 51.9 kDa and an isoelectric point of 5.99 (FIG. 5). We have named this protein NAALAD-ase IV. The putative ATG translation start codon is in a favourable context for translation initiation with no ATG codons detected upstream. Analysis of the NAALAD-ase IV sequence predicted a type II integral membrane protein containing a hydrophobic membrane spanning domain extending from amino acid 3 to approximately 24 with lysine residues found on either side of the potential membrane-spanning domain (determined by the method of Kyte and Doolittle, 1982). There are 5 potential N-glycosylation sites (N×S/T) indicated in FIG. 5.

The predicted protein sequences of NAALAD-ase I, L, II and IV were compared to each other using the alignment program BESTFIT (Wisconsin package, Genetics Computer Group Software, Madison, Wis., USA). The % identity and % similarity between each pair of sequences calculated by the Genedoc program is indicated in Table 1. NAALAD-ase I sequence was 67% identical to NAALAD-ase II, 35% identical to NAALAD-ase L and 10% identical to NAALAD-ase IV. NAALAD-ase L and II were 37% identical. The four protein sequences for NAALAD-ase I, II, L and IV were aligned using the ClustalW alignment program (EMBL, Heidelberg, Germany) and are shown in FIG. 6. The highest regions of conservation between these proteins occur in the two predicted catalytic domains. A phylogram of NAALAD-ase I, II, L and IV was constructed using GCG 'Distances' program with standard parameters and the 'Growtree' program with the UPGMA method and is depicted in FIG. 7. From this phylogram it is clear that NAALAD-ase I and II are the most closely related proteins with NAALAD-ase IV being the distant relative.

Two putative catalytic domains have been identified in NAALAD-ase I and L sequences by comparison to other peptidases (Bzegda et al., 1997; Shneider et al., 1997). Using multiple sequence alignments of NAALAD-ase I, II, L and IV we have identified similar putative catalytic domains in human NAALAD-ase II, L and IV (see FIGS. 6 and 8). The first catalytic domain is related to bacterial and yeast $Zn^{2+}$ dependent peptidase domains (Bzegda et al., 1997). Alignments of these peptidases with NAALAD-ases I, II, L and IV are shown in FIG. 8. All five residues important in $Zn^{2+}$ binding are conserved in the NAALAD-ase family. Additionally, a Glu residue thought to play a role in catalysis is also present. The NAALAD-ase IV sequence, although more distantly related, also shows statistically significant similarity to the bacterial and yeast amino-peptides $Zn^{2+}$ binding domain as determined by the Blastp algorithm (~60% similar, p=10–5). The second catalytic domain is related to members of the α/β hydrolase fold family of proteins (Shneider et al., 1997). Interestingly, there is a conserved nucleophile-acid-base alignment amongst NAALAD-ase I, II and L that may be important in the enzymes catalytic activity (Goossens et al., 1995). Rat NAALAD-ase L has been suggested to belong to an α/β hydrolase fold family of peptidases, similar to dipeptidyl peptidase IV (DPPIV). In contrast, NAALAD-ase IV which is about 270 residues shorter than the other NAALAD-ase proteins lacks this domain.

Alternative Splicing of NAALAD-ase L.

In the course of the cloning and RT-PCR gene expression analysis of NAALAD-ase L a number of amplified PCR products were observed, isolated and sequenced in order to identify possible splice variants. We found both the splicing out of putative exon sequences, as well as the presence of intronic sequences, as judged by the presence of GT/AG donor/acceptor sites, that were repeatedly amplified from our cDNA preparations (FIG. 3). When performing 5' RACE amplifications deletions between bases 497–619 and 903–1007 were identified in small intestine and colon that resulted in two in-frame amino acid deletions. In addition a 153 bp intron was found inserted at base 1094 resulting in an in-frame amino acid insertion of 51 amino acid residues. This insertion is most likely an intron as it has the consensus GT/AG donor acceptor sites at its 5' and 3' ends respectively. In the 3' RACE amplification reactions several variants were also identified in amplifications from small intestine, colon, brain and foetal brain. These consisted of either a deletion of bases 1525–1615 or a larger deletion between bases 1525–1697. Both these deletions resulted in frame shifts and the premature termination of the protein sequence. Finally, in every cDNA sample examined, two intronic sequences were found to be inserted at either base 1697 and/or at base 1870. Inclusion of one or both of these intronic sequences into the ORF of NAALAD-ase L accounted for the unexpected amplified PCR products migrating at 420 and 500 bp in the RT-PCR experiments. Introduction of one or both these sequences results in a frame shift of the amino acid coding sequence (FIG. 3).

Expression and functional activity of NAALAD-ases. To determine if the newly identified NAALAD-ases had peptidase activity, mammalian expression constructs were transiently transfected into COS cells. Membranes from mock transfections were always prepared in parallel as negative controls. Expression of NAALAD-ase I in COS cells was performed as positive control to establish the working conditions of the assay. FIG. 9A shows the amount of [3H]-glutamate in dpms eluted off mini-columns following incubation of [3H]-NAAG with the recombinant NAALAD-ase I. Increasing [3H]-glutamate is eluted from the column in a time dependent manner. Activity was observed for both NAALAD-ase L (data no shown) and NAALAD-ase II (FIG. 9B) suggesting that these enzymes have a similar dipeptidase activity as NAALAD-ase I in this assay. No NAALAD-ase IV dipeptidase activity was observed under these assay conditions. Addition of 30 μM quisqualic acid to the reaction inhibited this activity by over 50% after 60 min (FIGS. 9A and 9B). Inhibition curves with increasing concentrations of QA were also performed (FIG. 9C) with $IC_{50}$ values of $1.2\times10^{-5}$ M and $1.7\times10^{-5}$ M for NAALAD-ase I NAALAD-ase II respectively.

A scintillation proximity assay (SPA) was also developed in order to facilitate screening of NAALAD-ase type activity using either the recombinant proteins or membrane preparations from sources known to contain NAALAD-ase activity. A time course of [3H]-NAAG hydrolysis was initially performed using NAALAD-ase I rich LNCaP membrane preparations (FIG. 10A). Stopping the reaction with glycine buffer resulted in binding of the remaining [3H]-NAAG substrate to the SPA beads whereas hydrolysed [3H]-glutamate remained unbound. Therefore as the reaction proceeded and the substrate is hydrolysed, a decrease in signal bound to the beads is observed. Under these SPA conditions, inhibition curves were performed on LNCaP membranes or recombinant NAALAD-ase I membrane preparations using increasing concentrations of QA (FIG. 10B). The IC50 values were $9.1\times10^{-7}$ M for LNCaP preparations and $1\times10^{-6}$ M for NAALAD-ase I preparations.

Chromosomal Localisation.

The complete coding sequence of NAALAD-ase I was used as a probe for FISH analysis. Under the conditions used, the hybridisation efficiency was approximately 71% for this probe (among 100 checked mitotic Figures, 71 of them showed signals on one pair of the chromosomes). DAPI banding was used to identify the specific chromosome and an assignment between the signal from the probe and the short arm of chromosome 11 was obtained. The detailed position was further determined based upon summary data from 10 photographs (FIG. 11). A weak hybridisation signal was also detected in the region of 11q14.3 with low frequency. With the mapping data obtained from NAALAD-ase II it was concluded that this weak signal was a result of cross-hybridisation (see later) and that NAALAD-ase I is located solely at human chromosome 11, region p11.21. Example of the mapping results are presented in FIG. 11. For NAALAD-ase L, a 1059 bp fragment (from pos. 1204–2262 bp) was used as a probe for FISH analysis. The hybridisation efficiency was approximately 71% and DAPI banding was used to identify the signal to the long arm of chromosome 11. The detailed position determined from 10 photographs was on human chromosome 11, region q12 (FIG. 11). For NAALAD-ase II, a 2.5 kb fragment (from pos. 1–2552 bp) was used as a probe for FISH analysis. The hybridisation efficiency was approximately 74% for this probe. DAPI banding was used to identify the signal to the long arm of chromosome 11. The detailed position determined from 10 photographs was on human chromosome 11, region q14.3-q21 (FIG. 11). For NAALAD-ase IV, a 1539 bp fragment (from pos. 1–1539 bp) was used as a probe for FISH analysis. The hybridisation efficiency was approximately 72% for this probe. DAPI banding was used to identify the signal to the long arm of chromosome 8. The detailed position (FIG. 11) determined from 10 photographs was on human chromosome 8, region q21.3.

Tissue Distribution of NAALAD-ase III and IV as Determined by Northern Blot.

The tissue distribution of TrnR3 in different brain regions and in non-neuronal tissues was investigated using RT-PCR, Northern blot analysis and in situ hybridization. Northern blot analysis was performed on mRNA derived from different human tissues (FIG. 12A). A NAALAD-ase II specific probe indicated the presence of transcripts in testis>>>ovary, spleen>prostate, heart and placenta with no signal observed in other tissues. In testis, four transcripts were represented. The most predominant transcript was of approximately 3.4 kb, consistent with the approximate expected size of a NAALAD-ase II message. Two transcripts of 2.4 and 4.4 kb respectively and a weaker transcript of about 7.5 kb were also present. In the other tissues the 3.4 kb transcript was the only signal detected, apart from ovary where a weak 7.5 kb signal could also be seen. The precise nature of these transcripts awaits further elucidation but may be due to alternative splicing of the message. The nature of these messages is unclear. A NAALAD-ase IV specific probe showed the ubiquitous presence of transcripts in all tissues examined with slightly less signal observed in brain, thymus and testis (FIG. 12B). The most predominant transcript was of approximately 2.2 kb, consistent with the approximate expected size of a NAALAD-ase IV message, with a faint band detected in some tissues at 4.4 kb.

Analysis of NAALAD-ase gene expression by RT-PCR. To further examine the detailed tissue distribution of all NAALAD-ases, PCR was performed on normalised cDNAs from 16 different tissues. FIG. 13A shows the results from PCR reactions performed with NAALAD-ase I specific primers, yielding amplification products of the expected size (~341 bp). Highest expression of NAALAD-ase I appeared to be in prostate. Rank order of expression after 25 cycles was prostate>>>liver and kidney>small intestine>brain, spleen, with no product amplification observed in the other tissues. At 30 cycles amplification products could be seen in most other tissues with the exception of muscle, blood and thymus in which products could only be observed after 35 cycles of amplification. NAALAD-ase L specific primers yielded a 330 bp amplification product of the expected size, as well as two products migrating with slightly higher sizes of 420 bp and 500 bp (FIG. 13B). NAALAD-ase L expression was highest in small intestine, spleen and testis with PCR products detected after 25 cycles of amplification, whilst products in heart, ovary, colon, blood and prostate could be seen after 30 cycles. All tissues exhibited some amplification products following 35 cycles with brain and muscle showing the lowest levels. The 420 and 500 bp bands were due to amplification of NAALAD-ase L sequences containing one or two intronic sequences that were commonly found in all our amplification reactions (see earlier). NAALAD-ase II specific primers yielded a 353 bp amplification product of the expected size (FIG. 13C). NAALAD-ase II expression was highest in ovary, testis and spleen with PCR products detected after 25 cycles of amplification. After 30 cycles amplification products could be detected from all tissue cDNAs apart from lung, muscle, blood and thymus in which a product could only be seen after 35 cycles. These results are in good accordance with the expression data obtained with the MTN Northern blots. NAALAD-ase IV specific primers yielded a 336 bp amplification product of the expected size (FIG. 13D). NAALAD-ase IV expression was low in all tissues with amplification products only detected after 35 cycles. Expression levels were comparable in all the cDNAs apart from brain, lung, muscle and thymus in which no amplification products were clearly visible. Control amplification reactions using GAPDH specific primers demonstrated comparable levels of amplification products for each cDNA (FIG. 13E). Comparison of the relative abundance between the four messages was also possible from these experiments, since the same cDNAs were used for each set of amplifications. Abundance of NAALAD-ase I message was greater than NAALAD-ase II which was greater than NAALAD-ase L, as judged by the relative amount of amplification products detected at 25 and 30 cycles. NAALAD-ase IV was expressed at the lowest levels, with PCR products detected only after 35 cycles of amplification.

PCR reactions were also performed with the same NAALAD-ase primers as in the above experiments, on 13 different brain cDNAs normalised to the expression levels of three different housekeeping genes. NAALAD-ase I specific amplification products were detected with highest levels of ventral striatum and brain stem after 30 cycles. After 35 cycles NAALAD-ase I specific amplification products could clearly be detected in all brain areas studied (FIG. 14A). NAALAD-ase L specific primers yielded a 330 bp amplification product of the expected size, as well as a product migrating at a higher size of 500 bp (FIG. 14B). Amplification of the 500 bp product was observed after 35 cycles in brain stem, amygdala, thalamus, ventral striatum and to a lesser extent in striatum and hippocampus, whereas the 330 bp product of the expected size was only seen in brain stem and ventral striatum. NAALAD-ase II specific primers yielded a 353 bp amplification product of the expected size (FIG. 14C). Amplification products were observed after 30 cycles in striatum, parietal cortex and ventral striatum with lower levels of amplification product detected in hippocampus, brain stem, putamen and superior colliculus. After 35 cycles the presence of NAALAD-ase II specific products could be detected in all cDNAs apart from inferior colliculus. NAALAD-ase IV specific products could be detected in all brain cDNAs studied after 30 cycles with little difference observed in expression pattern. Levels of amplification products were slightly higher in striatum, hippocampus, brain stem and ventral striatum (FIG. 14D). Control amplification reactions using GAPDH specific primers demonstrated comparable levels of amplification products for each cDNA apart from brain stem which yielded relatively more GAPDH specific product (FIG. 14E). Overall expression of NAALAD-ase L appears to be lower in these brain areas relative to NAALAD-ase I, II and IV.

Finally, NAALAD-ase expression was investigated in cDNAs prepared from either prostate tumour cell lines or a prostate tumour, that had been normalised against three different housekeeping genes. NAALAD-ase I expression was highest in LNCaP and prostate tumour (FIG. 15A). Amplification products were also detected in PC-3 cDNA after 30 and 35 cycles but not in DU145 cDNA. The 330 bp NAALAD-ase L product was detected in highest amounts in cDNA from prostate tumour and less in PC-3 and DU145 samples after 35 cycles (FIG. 15B). Interestingly, in all samples apart from prostate tumour, the higher 500 bp amplification product could be detected. NAALAD-ase II expression was higher in LNCaP than prostate tumour. A faint amplification product could also be detected in PC-3 after 35 cycles but not in DU145 cDNA (FIG. 15C). NAALAD-ase IV expression was highest in LNCaP and prostate tumour (FIG. 15D). Representative amplification with GAPDH primers are also shown (FIG. 15E).

NAALAD-ase I is a type II membrane glycoprotein, with carboxypeptidases activity and sequence similarly to the transferrin receptor (54% identical, Israeli et al., 1993). It may be important in the progression of prostate cancer since it is highly expressed in prostate tumours, and in the CNS it may have an important role in modulating neuronal glutamatergic activity. In this report we describe the identification and cloning of human cDNAs encoding distinct NAALAD-ase enzymes, that represent an expansion of this family of proteins. We have identified in this report two novel members of the NAALAD-ase enzyme family, NAALAD-ase II and NAALAD-ase IV and determined the full coding sequence of human NAALAD-ase L. The degree of divergence of NAALAD-ase L, II and IV at the amino acid sequence level indicates that these are not variants of existing known genes but new and distinct members of this family. As has been determined for NAALAD-ase I, features common to all three receptors include a hydrophobic leader sequence at the amino-terminus suitable for secretion, and the presence of several possible N-glycosylation sites. All three novel NAALAD-ases contain a single hydrophobic region of approximately 21 to 24 amino acid residues at their amino-terminus, which is likely membrane spanning, a short intracellular domain and a large globular extracellular domain. This structure is typical of type II integral membrane proteins and is common amongst membrane bound hydrolases (Kenny et al., 1982). Sequence alignment comparisons of the four proteins suggests that NAALAD-ase II is most closely related to NAALAD-ase I (81% similar at the amino acid level), whereas NAALAD-ase L is equally similar to both NAALAD-ase I and II (54% similar to both). NAALAD-ase IV is distantly related to the other members of the family.

Analysis of NAALAD-ase L sequences using different PCR primers sets revealed the presence of multiple splice variants and isoforms. The biological significance or alternatively spliced isoforms of NAALAD-ase L awaits further clarification. However, the spliced out residues may affect levels of glycosylation and more importantly the conformation and activity of the protein. Furthermore, inclusion of three different intronic sequences identified in amplification reactions from numerous cDNAs, result in either an in-frame addition of a proline rich, 51 amino acid residue, sequence close to the putative catalytic zinc binding domain, or in frame shifts and subsequent premature termination of the NAALAD-ase L protein. These premature terminations result in elimination of the predicted nucleophile-acid-base arrangement of the putative catalytic site found in $\alpha/\beta$ hydrolases and will result in a gross change in the proteins conformation (see FIG. 3). Inclusion of two of the intronic DNA sequences, resulting in frame shifts and premature protein termination, were identified in nearly all the cDNAs studied, suggesting that expression of these sequences may be used to regulate the levels of active protein. Expression studies using these different splice variants will help to understand the structure/activity relationship of NAALAD-ase L and help identify which amino acid residues within the protein are important for enzymatic activity. A soluble splice variant of NAALAD-ase I has been reported, lacking the first 40 amino acid residues, including the membrane spanning domain (Su et al., 1995). An increased ratio of full length protein to truncated protein was observed in malignant prostate tissues, suggesting that expression of alternative splice variants may correlate with tumour progression. Further work will determine if NAALAD-ase L is involved in oncogenesis and if these splice variants effect tumour progression to differing degrees.

In human tissues, NAALAD-ase I mRNA was highly expressed in prostate but also in liver, kidney and small intestine and to a lesser extent in brain and spleen. This is partial agreement with Northern blot results obtained in rat in which the highest levels of expression were found to be in brain and kidney but not liver or spleen (prostate was not studied; Bzedga et al. 1997; Carter et al., 1998). NAALAD-ase L expression by RT-PCR was highest in spleen, small intestine and testis. Schneider and colleagues (1997) identified a rat ileal 100 kD protein (I-100; rat NAALAD-ase L) expressed in rat ileum and human small intestine as seen by Northern blot, but not in testis or spleen. Discrepancies between NAALAD-ase I and L expression patterns could be attributed either to species differences or t the increased sensitivity of mRNA detection by RT-PCR compared to Northern blot hybridisation. NAALAD-ase II mRNA expression was studied both by Northern blot and RT-PCR experiments. Expression experiments using these methods yielded comparable results with the highest levels of mRNA expression being observed in testis and ovary, with less message in spleen, placenta and heart. A number of differently sized transcripts were observed that hybridised to the NAALAD-ase II probe, suggesting the presence of multiple isoforms. It remains to be determined whether these are due to physiologically relevant smaller transcripts or due to problems with the integrity of the mRNA. NAALAD-ase IV mRNA expression was also studied using both techniques and expression data were consistent between the experiments. NAALAD-ase IV expression appeared to be more evenly distributed amongst tissues, with the highest expression in ovary and little or no expression in brain, lung, thymus and testis. Analysis of NAALAD-ase expression in different human brain areas by RT-PCR suggests that NAALAD-ase L is expressed at lowest levels in these brain areas. The amplification products (except those from ventral striatum) migrating at 500 bp were of a higher than expected size and found to contain intronic DNA sequences (see earlier). NAALAD-ase I, II and IV were expressed at the mRNA level in almost all brain areas studied to differing degrees, with highest expression observed in brain stem, striatum, ventral striatum and putamen. In addition, NAALAD-ase II expression appeared relatively more abundant in frontal and parietal cortex. RT-PCR experiments performed on various prostate tumour cell lines and on a prostate tumour sample agreed with reports showing that NAALAD-ase I is expressed in highest amounts in the androgen receptor positive LNCaP cell line (Israeli et al., 1993). Some amplification products were also observed in PC-3 cells after 30 and 35 cycles of amplification, in contrast to previous studies detecting no message in the androgen receptor negative cells DU-145 and PC-3 by Northern blotting (Israeli et al. 1993). Since low levels of NAALAD-ase actively have been observed in these latter two cell lines, some expression of these enzymes, including NAALAD-ase I, may occur (Pinto et al., 1996). NAALAD-ase II was also expressed in LNCaP cells at the highest levels, whereas NAALAD-ase IV expression was highest in PC-3 cells. Interestingly, NAALAD-ase L amplification products from LNCaP cells were of a higher than expected size and contained intronic sequences, in contrast to the product observed from prostate tumour. PC-3 and DU-145 cells yielded both the high and low sized amplification products.

Carboxypeptidase activity of NAALAD-ase I has been demonstrated against two classes of substrate in vitro. The first is based on the enzymes ability to hydrolyse x-linked acidic peptides such as N-acetylaspartyl glutamate (NAAG) or x-glutamylglutamate and the second is based on its ability to hydrolyse γ-linked peptides such as folyl-poly-γ-glutamate or -γ glutamylglutamate. In this study we have expressed NAALAD-ase II, L and IV in COS cells and studied the ability of these recombinant preparations to hydrolyse NAAG. NAALAD-ase I, II and L all showed activity against this substrate that was inhibited by QA. QAIC50s for NAALAD-ase I and II were determined to be about 10 μM for both proteins, comparable to that described for NAALAD-ase activity in lysed synaptosomal membranes (Robinson et al., 1987). The X-linked NAALAD-ase hydrolysis of NAAG was initially characterised in membrane preparations from brain and shown to be QA sensitive. Activity was increased by divalent cations and inhibited by divalent metal chelators or general metalloprotease inhibitors (Robinson et al., 1987; Blakely et al, 1988). It was subsequently shown that the enzymatic activity associated with prostate specific marker (PSM, Carter et al., 1996) and rat brain carboxypeptidase II (Luthi-Carter et al., 1998) following transfection experiments, exhibited similar enzyme characteristics to those observed for the QA sensitive NAALAD-ase activity. It has previously been shown that alignment of NAALAD-ase I with zinc amino peptidases from yeast and bacteria identifies a domain of conserved sequences involved in the co-ordination of two zinc ions locate din the catalytic site (Bzedga et al., 1997), Rawlings et al., 1997). The basis for these observations comes from the three dimensional crystal structure of the *Aeromonas proteolytica* zinc aminopeptidase in which residues His 379, Asp 389, Glu 427, Asp 455, His 555 are thought to be involved in the binding of two zinc ions and Glu426 is proposed to be a base residue important in catalysis (Chevrier et al., 1994, 1996). Alignment of the newly identified NAALAD-ases with these amino peptidases (FIG. 8) shows that these zinc binding domains are conserved, suggesting that they may all share the same catalytic mechanism. Bzedga and colleagues (1997) have further suggested that NAALAD-ase I may be a member of the α/β hydrolase fold family because of its dipeptidyl IV and acylaminoacyl peptidase activity, although sequence homology alignments have shown these proteins to be clearly distinct. However, a hypothesised catalytic site arrangement of nucleophile, acid and base (Ser 623, Asp 663 and His 686) is covered and found in NAALAD-ase I, L and II but absent from NAALAD-ase IV (see FIG. 6). The second γ-linked enzymatic activity of NAALAD-ase I to peptides such as pteroyl-γ-glutamate (folate hydrolase activity) has been found at high levels in the brush border of human small intestine (Chandler et al., 1986; Pinto et al., 1996). In addition, carcinoma cells transfected with NAALAD-ase I show increased folate hydrolase activity and the ability to progressively liberate glutamate from methotrexate triglutamate by hyrolysis of γ-glutamyl linkages (Pinto et al., 1996). Indeed, a correlation has been observed between increased pteroyl hydrolases activity and methotrexate resistance in tumours (Banerjee et al., 1986), suggesting that modulating NAALAD-ase activity may be important in developing improved or novel cancer treatments. It will be interesting to determine if these novel NAALAD-ase enzymes with their common secondary structure also have a dual peptidase activity as has been described NAALAD-ase I, and how their structural relationship reflects their activity. Using FISH analysis to determine the chromosomal localisation of NAALAD-ase I, II and L we observed a symmetrical fluorescent signal on chromosome 11, at p11.21 for NAALAD-ase I, q12 for NAALAD-ase L and between q14.3-q21 for NAALAD-ase II. In our FISH studies a NAALAD-ase I probe revealed two hybridisation signals, one hybridising at 11p11.21 and another weekly at 11q14.3. This is similar to the results obtain by Leek and colleagues (1995) who observed two hybridisation signals at 11p11.2 and 11q13.5. Having now localised NAALAD-ase II to 11q14.3-q21, it is clear that the second signal is due to cross hybridisation of the NAALAD-ase I probe with the NAALAD-ase II locus. The chromosomal localisation of NAALAD-ase IV revealed a symmetrical fluorescent signal on human chromosome 8 at q21.3, suggesting that this gene is distantly related to the other three genes located on chromosome 11. Chromosome 11 contains a number of genetic disease loci in these regions, including vitreoretinopathy (11q13-q23), xeroderma pigmentosa (11q12-q13), atopy (11q12-q13) and perhaps more interestingly a tumour suppression locus (11p11.2-p11.13) involved in rat prostate carcinoma. Introduction of this portion of the chromosome into highly metastatic rate prostatic cells was able to suppress cancer metastases without suppression of the in vivo growth rate or tumourgenicity of the cells (Ichikawa et al., 1992). Since it has been shown that NAALAD-ase I expression increases with decreasing androgen levels, it is possible that current prostate cancer treatments involving androgen level reduction (e.g. orchidectomy) may work at least in part through alteration of NAALAD-ase expression (Israeli et al., 1994). The enzymatic activity of NAALAD-ase I is similar to that of NAALAD-ase II and L, so it is also conceivable by analogy that these enzymes may also have a role to play in tumour suppression. Interestingly, region 11q13-q23 has also been identified as a region with tumour suppressor activity using tumourgenic HeLa/fibroblast hybrids (Misra and Srivatsan, 1989). In addition, in a systematic analysis of primary cervical carcinomas, region 11q22-q24, was shown to contain tumour suppressor activity (Hampton et al., 1994). These latter two tumour suppressing regions on the long arm of chromosome 11, cover the gene loci of NAALAD-ase L and NAALAD-ase II identified in this study. However, it should be noted that mapping of these tumour suppressing activities to these three chromosomal regions, in no way establishes if any of the identified NAALAD-ases are capable of having tumour or metastatic suppressing activity. α-NAAG is one of the most abundant peptides in the brain, being present in millimolar concentrations in certain brain regions (see Coyle, 1997). Clarification of the physiological role of NAAG has been difficult as it is co-localised with L-glutamate, but it does fulfil some of the criteria for a neurotransmitter. It is localised in synaptic vesicles, is realised in $Ca^{2+}$ dependent manner from nerve terminals and is rapidly inactivated by a QA sensitive enzyme activity first identified in brain membrane preparations (Robinson et al., 1986, 1987). Cloning experiments revealed the sequence identity of this enzymatic activity to be derived from a previously identified protein, PSM (or NAALAD-ase I, Carter et al., 1996). In this study, NAALAD-ases L and II but not NAALAD-ase IV, have been shown to be able to hydrolyse [3H]-NAAG to N-acetylaspartate and glutamate as has been previously shown with NAALAD-ase I. Given the localisation of these NAALAD-ases in prostate and ovary, as well as other peripheral tissues, it is quite possible that these enzymes may modulate local extracellular glutamate levels in these tissues. For example it is known that substantial amounts of glutamate are present in seminal fluid. In the CNS, NAAG has been shown to act as a partial agonist at the NMDA receptor but not at AMPA or kainate receptors (Vallivullah et al., 1994; Puttfarcken et al., 1993; Sekiguchi et al., 1992) and to attentuate NMDA or glutamate induced neurodegeneration (Bruno et al., 1998). Furthermore, it has also been shown that addition of NAAG to hippocampal slices or mixed cortical cultures results in neuroprotection following addition of excitotoxins via a mechanism distinct from its action of the NMDA receptor. In this case it is postulated that NAAG, which is poorly transported or actively taken up, diffuses from the synaptic cleft and binds as an agonist to type II metabotropic glutamate receptors (mGluR), such as mGluR3, leading to reduced glutamatergic neurotransmission (Wroblewska et al., 1993 and 1997). This hypothesis has been further tested using the mGluR3 antagonist, ethylglutamate, which eliminated the neuroprotective actions of NAAG (Bruno et al., 1998). Although the intact peptide has predominantly inhibitory actions, another possible mechanism of excitotoxic induced cell death may arise from the aberrant catabolism of NAAG by NAALAD-ases. With endogenous levels of NAAG being so high in brain, catabolism of NAAG by NAALAD-ases should in theory be a rich source of glutamate, which if not properly regulated may result in excitotoxic effects. Indeed abnormal levels of NAAG or NAALAD-ase activity have been reported in epilepsy (Myerhoof et al., 1985 and 1992), Schitzophrenia (Tsai et al., 1995), ALS (Tsai et al., 1991), Alzheimer's disease (Passani et al., 1997a; Jaarsma et al., 1994 and stroke (Sager et al., 1995). Inhibition of NAALAD-ase activities with specific inhibitors may be useful in treating ischemic induced neurodegeneration or other neurodegenerative disorders involving abnormalities in glutamate neurotramsmission, such as Alzheimer's disease, schizophrenia or ALS (Passani et al., 1997b). In vitro at least, the NAALAD-ase (carboxypeptidase) inhibitor, 2-(phosphonemethyl) pentanedoic acid, inhibited toxicity induced by the carboxypeptidase cleavage of folic acid hexaglutamate (Slusher et al., 1997).

REFERENCES

Altschul, S. F., Gish, W., Miller, W., Myers, E. W. and Lipman, D. J. (1990). Basic local alignment search tool. J. Mol. Biol., 215, 403–410.

Bruno, V., Wroblewska, B., Wroblewski, J. T., Fiore, L. and Nicoletti, F. (1998) Neuroprotective activity of n-acetylaspartylglutamate in cultured cortical cells. Neurosci., 85(3), 751–757.

Burlina, A. P., Skaper, S. D., Mazza, M. R., Ferrari, V., Leon, A. and Burlina, A. B. (1994) N-acetylaspartylglutamate selectively inhibits neuronal responses to N-methyl-D-aspartic acid in vitro. J. Neurochem., 63(3), 1174–7, 1994.

Bzdega, T., Turi, T., Wroblewska, B., She, D., Chung, H. S., Kim, H. and Neale, J. H. (1997). Molecular cloning of a peptidase against N-acetylaspartylglutamate from a rat hippocampal cDNA library. J. Neurochem., 69, 2270–2277.

Carter, R. E. Feldman, A. R. and Coyle, J. T. (1996) Prostate-specific membrane antigen is a hydrolase with substrate and pharmacologic characteristics of a neuropeptidase. P. Natl. Acad. Sci. USA., 93(2), 749–753.

Cassidy, M. and Neale, J. H. (1993) N-acetylaspartylglutamate catabolism is achieved by an enzyme on the cell surface or neurons and glia. Neuropeptides., 25(4), 271–278.

Chandler, C. J., Wange, T. T. and Halsted, C. H. (1996) Pteroylpolyglutamate hydrolase from human jejunal brush borders. Purification and characterisation. J. Biol. Chem., 261(2), 928–933.

Chevrier, B., D'Orchymont, H., Schalk, C., Tarnus, C. and Moras, D. (1996) The structure of the *Aeromonas proteolytica* aminopeptidase complexed with a hydroxamate inhibitor. Involvement in catalysis of Glu51 and two zinc ions of the co-catalytic unit. Eur. J. Biochem., 237(2), 393–398.

Chevrier, B., Schalk, C., D'Orchymont, H., Rondeau, J. M., Moras, D. and Tarnus, C. (1994) Crystal structure of the *Aeromonas proteolytica* aminopeptidase, a prototypical member of the co-catalytic zinc enzyme family. Structure, 2, 283–291.

Coyle, J. T. (1997) The nagging question of the function of N-acetylaspartylglutamate. Neurobio. Disease., 4(3–4), 231–238, Ghose, S., Wroblewska, B., Corsi, L., Grayson, D. R., De Blas, A. L., Vicini, S. and Neale, J. H. (1997) N-acetylaspartylglutamate stimulates metabotropic glutamate receptor 3 to regulate expression of the GABA(A) $\alpha_6$ sub-unit in cerebellar granule cells. J. Neurochem., 69(6), 2326–2335.

Hampton, G. M., Penny, L. A., Baergen, R. N., Larson, A., Brewer. C., Liao, S., Busby-Earle, R. M., Williams, A. W., Steel, C. M., Bird C. C., Stanbridge, E. J. and Evans, G. A. (1994) Loss of heterozygosity in sporadic human breast carcinoma, a common region between 11q22 and 11q23.3. P. Natl. Acad. Sci. USA., 91 (6953–6957).

Ichikawa, T., Ichikawa, Y., Doing, J., Hawkins, A. L., Griffin, C. A., Isaacs, W. B., Oshimura, M., Barrett, J. C. Isaacs, J. T. (1992) Localisation of metastasis suppressor gene(s) for prostatic cancer to the short arm of human chromosome 11. Cancer Res., 52(12), 3486–3490.

Israel, R. S., Powell, C. T., Corr, J. G., Fair, W. R. and Heston, W. D. (1994) Expression of the prostate-specific membrane antigen. Cancer Res., 54(7), 1807–1811.

Israeli, R. S., Powell, C. T., Fair, W. R. Heston, W. D. (1993) Molecular cloning of a complementary DNA encoding a prostate-specific membrane antigen. Cancer Res., 53(2), 227–230. J. Neurochem., 69(1), 174–181.

Jaarsma, D., Veenma-van der Duin, L. and Korf, J. (1994) N-acetylaspartate and N-acetylaspartylglutamate levels in Alzheimer's disease port-mortem brain tissue. J. Neurol. Sci., 127(2), 230–233.

Kenny, A. J. and Maroux, S. (1982) Topology of microvillar membrane hydrolases of Kidney and intestine. Physiol. Revs. 62(1), 91–128.

Kozak, M. (1989) The scanning model for translation, an update. J. Cell Biol., 108, 229–241.

Kyte, J and Doolittle, R. F. (1982) A simple method for displaying the hydropathic character of a protein. J. Mol. Biol., 157(1), 105–132.

Leek, J., Lench, N., Maraj, B., Baily, A., Carr, I. M., Andersen, S., Cross, J., Whelan, P., MacLennan, K. A., Meredith, D. M. and Markham, A. F. (1995) Prostate-specific membrane antigen, evidence for the existence of a second related human gene. Brit. J. Cancer, 72(3), 583–588.

Luthi-Carter, R., Berger, U. V., Barczak, A., Enna, J. Coyle, J. T. (1998) Isolation and expression of a rat brain Cdna encoding glutamate carboxypeptidase II. P. Natl. Acad. Sci. USA., 95(6), 3215–3220.

Meyerhoff, J. L., Carter, R. E., Yourick, D. L., Slusher, B. S. and Coyle, J. T. (1992) Activity of a NAAG-hydrolyzing enzyme in brain may affect seizure susceptibility in genetically epilepsy-prone rates. Epilepsy Research (Supp.)., 9, 163–172.

Meyerhoff, J. L., Robinson, M. B., Bixler, M. A., Richards, S. S. and Coyle, J. T. (1989) Seizures decrease regionals enzymatic hydrolysis of N-acetylaspartylglutamate in rat brain. Brain Res., 505(1), 130–134.

Meyerhoff, J. L., Koller, K. J., Walczak, D. D. and Coyle, J. T., (1985) Regional brain levels of N-acetylaspartylglutamate, the effect of kindled seizures. Brain Res., 346(2), 392–396.

Misra, B. C. and Srivatsa, E. S. (1989) Localization of HeLa cell tumor-suppressor gene to the long arm of chromosome 11. Am. J. Hum. Genet., 45(4), 565–577.

Orlando, L. R., Luthi-Carter, R., Standaert, D. G., Coyle, J. T., Penney, J. B Jr. and Young, A. B. (1997) N-acetylaspartylglutamate (NAAG) protects against rat stiatal quinolinic acid lesions in vivo. Neurosci. Letts., 236(2), 91–94.

Passani, L. A., Vonsattel, J. P. and Coyle, J. T. (1997) Distribution of N-acetylaspartyl-glutamate immunoreactivity in human brain and its alteration in neurodegenerative disease. Brain Res., 772(1–2), 9–22.

Passani, L. A., Vonsattel, J. P., Carter, R. E. and Coyle, J. T. (1997) N-acetylaspartyl-glutamate, N-acetylaspartate, and N-acetylated alpha-linked acidic dipeptidase in human brain and their alterations in Huntington and Alzheimer's diseases. Mol. Chem. Neuropathol., 31(2), 97–118.

Pinto, J. T., Suffoletto, B. P., Berzin, T. M., Qiao, C. H., Lin, S., Tong, P. T., May, F., Mukherjee, B. and Heston, W. D. (1996) Prostate-specific membrane antigen, A novel folate hydrolase in human prostatic carcinoma cells. Clin. Caner Res., 2, 1445–1451.

Puttfarcken, P. S., Handen, J. S., Montgomery, D. T., Coyle, J. T. and Werling, L. (1993) N-acetyl-aspartylgultamate modulation of N-methyl-D-aspartate-stimulated [3H] norepinephrine relase from rat hippocampal slices. J. Pharmacol. Exp. Ther., 266(2), 796–803.

Rawlings, N. D. and Barrett, A. J. (1997) Structure of membrane glutamate carboxypeptidase. Biochim. et Bioph. Acta., 1339(2), 247–252.

Robinson, M. B., Blakely, R. D., Couto, R. and Coyle, J. T. (1987) Hydrolysis of the brain dipeptide N-acetyl-L-aspartyl-L-glutamate. Identification and characterisation of a novel N-acetylated alpha-linked acidic dipeptidase activity from rate brain. J. Biol. Chem., 262(30), 14498–14506.

Robinson, M. B., Blakely, R. D. and Coyle, J. T. (1986) Quisqualate selectively inhibits a brain peptidase which cleaves N-acetyl-L-aspartyl-L-glutamate in vitro. Eur. J. Biochem., 130(3), 345–347.

Sager, T. N., Laursen, H. and Hansen, A. J. (1995) Changes in N-acetyl-aspartate content during focal and global brain ischemia of the rate. J. Cerebr. Blood F. Met., 15(4), 639–646.

Sekiguchi, M., Wada, K. and Wenthold, R J. (1992) N-acetylaspartylglutamate acts as an agonist upon homomeric NMDA receptor (NMDAR1) expressed in Xenopusoocytes. FEBS Letts., 311(3) 285–289.

Serval, V., Barbeito, L., Pittaluga, A., Cheramy, A., Lavielle, S. and Glowinski, J. (1990) Competitive inhibition of N-acetylated-alpha-linked acidic dipeptidase activity by N-acetyl-L-aspartyl-beta-linked L-glutamate. J. Neurochem., 55(1), 39–46.

Shneider, B. L., Thevananther, S., Moyer, M. S., Walters, H. C., Rinaldo, P., Deverajan, P., Sun, A. Q., Dawson, P. A. and Ananthanarayanan M. (1997) cloning and characterisation of a novel peptidase from rat and human ileum. J. Biol. Chem., 272(49), 31006–31015.

Slusher, S, Thomas A. T., Jackson, P. F., Tiffany, C. W. and Suzdak, P. D. (1997) Folate polyglutamate toxicity in rat cortica neurones is attenuated by NAALAD-ase inhibition. Soc. Neurosci. Abst., 898.7.

Su, S. L., Huang, I. P., Fair, W. R., Powell, C. T. and Heston, W. D. (1995) Alternatively spliced variants of prostate-specific membrane antigen RNA, ratio of expression as a potential measurement of progression. Cancer Res., 55(7), 1441–1443.

Tsai, G., Passani, L. A., Slusher, B. S., Carter, R., Baer, L., Kleinman, J. E. and Coyle, J. T. (1995) Abnormal excitatory neurotransmiffer metabolism in schizophrenic brains. Arch. Gen. Psych., 52(10), 829–836.

Tsai, G. C., Stach-Slusher, B., Sim, L., Hedreen, J. C., Rothstein, J. D., Kuncl, R. and Coyle, J. T. (1991) Reductions in acidic amino acids and N-acetylaspartyl-glutamate in amyotrophic lateral sclerosis CNS. Brain Res., 556(1), 151–156.

Valivullah, H. M., Lancaster, J., Sweetnam, P. M. and Neale, J. H. (1994) Interactions between N-acetylaspartyl-glutamate and AMPA, kainate, and NMDA binding sites. J. Neurochem., 63(5), 1714–1719.

Wroblewska B., Wroblewski J T., Saab O H., Neale J H. (1993) N-acetylaspartylglutamate inhibits forskolin-stimulated cyclic AMP levels via a metabotropic glutamate receptor in cultured cerebellar granule cells. J. Neurochem., 63(3), 943–948.

Wroblewska, B., Wroblewqski, J. T, Pshenichkin, S., Surin, A., Sullivan, S. E. and Neale, J. H. (1997) N-acetylas-partylglutamate selectively activates mGluR3 receptors in transfected cells. J. Neurochem., 69, 174–181.

TABLE 1

|          | NALAAD-I | NALAAD-L | NALAAD-II | NALAAD-IV |
|----------|----------|----------|-----------|-----------|
| NAALAD-I | 100      | 54       | 81        | 21        |
| NAALAD-L | 35       | 100      | 54        | 17        |
| NAALAD-II| 67       | 37       | 100       | 21        |
| NAALAD-IV| 10       | 9        | 11        | 100       |

Comparison of the predicted protein sequences for NAALAD-ase I, L, II and IV. The sequences were compared two by two using the alignment program BESTFIT (GCG package). The obtained values for % IDENTITY (upper part of the table) and % similarly (lower part of the table) are shown.

LIST OF USED ABBREVIATIONS

| | |
|---|---|
| BLAST | basic local alignment search tool |
| bp | base pairs |
| CMV | cytomegalovirus |
| DMEM | defined minimal essential medium |
| EST | expressed sequence tag |
| FISH | fluorescent in situ hybridisation |
| GAPDH | glyceraldehyde-3-phosphate dehydrogenase |
| I100 | ileal 100 kDa protein |
| IPTG | isopropyl-β-D-thiogalactoside |
| MEM | minimal essential medium |
| NAALAD-ase | N-acetylated alpha-linked acidic dipeptidase |
| NAAG | N-acetyl-L-aspartyl-L-(3,4)-glutamate |
| ORF | open reading frame |
| PBS | phosphate buffered saline |
| PCR | polymerase chain reaction |
| PSM | prostate specific marker |
| QA | quisqualate |
| RACE | rapid amplification of cDNA ends |
| RT-PCR | reverse transactiption polymerase chain reaction |
| SDM | site directed mutagenesis |
| SPA | scintillation proximity assay |
| SSC | sodium chloride sodium citrate |
| TAE | Tris acetate EDTA |
| X-Gal | 5-bromo-4-chloro-3-indolyl-B-D-galactopyranoside |

The invention claimed is:

1. An isolated human NAALAD-ase L protein having the amino acid sequence set forth in SEQ ID NO:35.

2. An isolated human NAALAD-ase L protein having an amino acid sequence selected from the group of amino acid sequences consisting of SEQ ID NO:61, SEQ ID NO:63, SEQ ID NO:65, SEQ ID NO:67 and SEQ ID NO:69.

* * * * *